United States Patent
Richardson

(10) Patent No.: US 9,399,062 B2
(45) Date of Patent: Jul. 26, 2016

(54) PVRL4 (NECTIN4) IS A RECEPTOR FOR MEASLES VIRUS

(75) Inventor: Christopher D. Richardson, Halifax (CA)

(73) Assignee: Christopher D. Richardson, Halifax, Nova Scotia (CA)

(*) Notice: Subject to any disclaimer, the term of this patent is extended or adjusted under 35 U.S.C. 154(b) by 0 days.

(21) Appl. No.: 13/980,392

(22) PCT Filed: Jan. 17, 2012

(86) PCT No.: PCT/IB2012/000183
§ 371 (c)(1),
(2), (4) Date: Jul. 18, 2013

(87) PCT Pub. No.: WO2012/098465
PCT Pub. Date: Jul. 26, 2012

(65) Prior Publication Data
US 2013/0295114 A1    Nov. 7, 2013

Related U.S. Application Data

(60) Provisional application No. 61/433,679, filed on Jan. 18, 2011.

(51) Int. Cl.
| | | |
|---|---|---|
| A61K 39/165 | (2006.01) | |
| A01N 63/00 | (2006.01) | |
| C12N 7/00 | (2006.01) | |
| A61K 39/42 | (2006.01) | |
| A61K 31/713 | (2006.01) | |
| A61K 35/76 | (2015.01) | |
| G01N 33/574 | (2006.01) | |

(Continued)

(52) U.S. Cl.
CPC ............. *A61K 39/42* (2013.01); *A61K 31/713* (2013.01); *A61K 35/76* (2013.01); *A61K 35/768* (2013.01); *C12Q 1/6886* (2013.01); *G01N 33/574* (2013.01); *C12N 2760/18432* (2013.01); *C12Q 2600/106* (2013.01); *C12Q 2600/156* (2013.01); *G01N 2333/12* (2013.01); *G01N 2333/70503* (2013.01)

(58) Field of Classification Search
None
See application file for complete search history.

(56) References Cited

U.S. PATENT DOCUMENTS

| | | | |
|---|---|---|---|
| 6,896,881 B1 * | 5/2005 | Russell et al. | ............... 424/93.2 |
| 7,670,598 B2 | 3/2010 | Russell et al. | |

(Continued)

FOREIGN PATENT DOCUMENTS

| | | | |
|---|---|---|---|
| WO | WO 0223994 A1 * | 3/2002 | |
| WO | WO 2010/067487 A1 | 6/2010 | |

OTHER PUBLICATIONS

Suter et al., "In Vitro Canine Distemper Virus Infection of Canine Lymphoid Cells: A Prelude to Oncolytic Therapy for Lymphoma," Clin. Cancer Res. 11: 1579-1587 (2005).*

(Continued)

*Primary Examiner* — Benjamin P Blumel
*Assistant Examiner* — M. Franco Salvoza
(74) *Attorney, Agent, or Firm* — Kilpatrick Townsend & Stockton LLP

(57) ABSTRACT

PVRL4 is a tumor marker that is highly expressed on the surfaces of many carcinomas. Disclosed herein are compositions and methods that provide impetus for using measles virus as an oncolytic agent against PVRL4+ carcinomas and use of PVRL4-binding agents to interfere with viral infection.

16 Claims, 21 Drawing Sheets

(51) Int. Cl.
*A61K 35/768* (2015.01)
*C12Q 1/68* (2006.01)

(56) References Cited

U.S. PATENT DOCUMENTS

2003/0044893 A1* 3/2003 Baum et al. ............... 435/69.1
2011/0171219 A1* 7/2011 Merchant ................. 424/134.1

OTHER PUBLICATIONS

Galanis, "Therapeutic Potential of Oncolytic Measles Virus: Promises and Challenges," Nature vol. 88, No. 5: 620-625 (2010).*
Colf et al., "Structure of the measles virus hemagglutinin," Nature Structural and Molecular Biology, vol. 14, No. 12: 1227-1228 (2007).*
Ariad, S., et al., "Measles virus: association with cancer," Clinical & Cellular Immunology, Dec. 19, 2011, pp. 1-5, vol. S5, No. 002.
Barton, E.S., et al., "Junction adhesion molecule is a receptor for reovirus," Cell, 2001, vol. 104, pp. 441-451.
Bartz, R., et al., "Differential receptor usage by measles virus strains," Journal of General Virology, 1998, vol. 79 (Pt 5), pp. 1015-1025.
Bartz, R., et al., "Mapping amino acids of the measles virus hemagglutinin responsible for receptor (CD46) Downregulation," Virology, 1996, vol. 224, pp. 334-337.
Blake, F.G., et al., "Studies on Measles : I. Susceptibility of Monkeys to the Virus of Measles," J. Exp. Med., 1921, vol. 33, pp. 385-412.
Blechacz, B., et al., "Measles virus as an oncolytic vector platform," Current Gene Therapy, 2008, vol. 8, pp. 162-175.
Bluming, A.Z., et al., "Regression of Burkitt's lymphoma in association with measles infection," Lancet, 1971, vol. 2, pp. 105-106.
Bonaparte, M.I., et al., "Ephrin-B2 ligand is a functional receptor for Hendra virus and Nipah virus," Proc. Natl. Acad. Sci. USA, 2005, vol. 102, pp. 10652-10657.
Buckland, R., et al., "Is CD46 the cellular receptor for measles virus?" Virus Research, 1997, vol. 48, pp. 1-9.
Burnstein, T., et al., "The Development of a Neurotropic Strain of Measles Virus in Hamsters and Mice," Journal of Infectious Disease, 1964, vol. 114, pp. 265-272.
Coyne, C.B., et al., "Coxsackievirus entry across epithelial tight junctions requires occludin and the small GTPases Rab34 and Rab5," Cell Host Microbe, 2007, vol. 2, pp. 181-192.
Craighead, J.E., "Rubeola (Measles)," Pathology and pathogenesis of human viral disease, 2000, pp. 397-410.
Derycke, M.S., et al., "Nectin 4 overexpression in ovarian cancer tissues and serum: potential role as a serum biomarker," American Journal for Clinical Pathology, 2010, vol. 134, pp. 835-845.
De Swart, R.L., "Measles studies in the macaque model," Current Topics in Microbiology and Immunology, 2009, vol. 330, pp. 55-72.
De Swart, R.L., et al., "Predominant infection of CD150+ lymphocytes and dendritic cells during measles virus infection of macaques," PLoS Pathogens, 2007, vol. 3, Issue 11, e178, pp. 1771-1781.
Dorig, R., et al., "The human CD46 molecule is a receptor for measles virus (Edmonston strain)," Cell, Oct. 22, 1993, vol. 75, No. 2, pp. 295-305.
Enders, J.F., et al., "Development of attenuated measles-virus vaccines," A summary of recent investigation, American Journal of Diseases of Children, 1962, vol. 103, pp. 335-340.
Erlenhoefer, C., et al., "CD150 (SLAM) is a receptor for measles virus but is not involved in viral contact-mediated proliferation inhibition," Journal of General Virology, 2001, vol. 75, pp. 4499-4505.
Fabre-Lafay, S., et al., "Nectin-4, a new serological breast cancer marker, is a substrate for tumor necrosis factor-alpha-converting enzyme (TACE)/ADAM-17," J Biol Chem., 2005, vol. 280, pp. 19543-19550.
Fabre-Lafay, S., et al., "Nectin-4 is a new histological and serological tumor associated marker for breast Cancer," BMC Cancer, 2007, vol. 7, pp. 73-89.
Geraghty, R.J., et al., "Entry of alphaherpesviruses mediated by poliovirus receptor-related protein 1 and poliovirus receptor," Science, 1998, vol. 280, pp. 1618-1620.
Griffin, D.E., et al., "Age dependence of viral expression: comparative pathogenesis of two rodent-adapted strains of measles virus in mice," Infection and Immunity, 1974, vol. 9, pp. 690-695.
Griffin, D.E., "Measles Virus," Fields Virology, 2007, pp. 1551-1585. New York: Lippincott, Williams, and Wilkins.
Griffin, D.E., "Measles Virus," Fields' Virology, 2001, New York: Lippincott, Williams, and Wilkins. pp. 1401-1442.
Hashiguchi, T, et al., "Structure of the measles virus hemagglutinin bound to its cellular receptor SLAM," Nature Structural & Molecular Biology, 2011, vol. 18, pp. 135-141.
Hashimoto, K., et al., "SLAM (CD150)-independent measles virus entry as revealed by recombinant virus expressing green fluorescent protein," Journal of Virology, 2002, vol. 76, pp. 6743-6749.
Hsu, E.C., et al. "A single amino acid change in the hemagglutinin protein of measles virus determines its ability to bind CD46 and reveals another receptor on marmoset B cells," Journal of General Virology, 1998, vol. 72, pp. 2905-2916.
Hsu, E.C., et al., "Artificial mutations and natural variations in the CD46 molecules from human and monkey cells define regions important for measles virus binding," Journal of Virology, 1997, vol. 71, pp. 6144-6154.
Hsu, E., et al., "CDw150(SLAM) is a receptor for a lymphotropic strain of measles virus and may account for the immosuppressive properties of this virus," Virology, Jan. 5, 2001, vol. 279, No. 1, pp. 9-21.
Hsu, E.C., et al., "Use of sites-pecific mutagenesis and monoclonal antibodies to map regions of CD46 that interact with measles virus H protein," Virology, 1999, vol. 258, pp. 314-326.
Kemper, C., et al., "Measles virus and CD46," Current Topics in Microbiology and Immunology, 2009, vol. 329, pp. 31-57.
Kobune, F., et al., "Marmoset lymphoblastoid cells as a sensitive host for isolation of measles virus," Journal of General Virology, 1990, vol. 64, pp. 700-705.
Kobune, F., et al., "Nonhuman primate models of measles," Lab. Anim. Sci., 1996, vol. 46, pp. 315-320.
Lecouturier, V., et al., "Identification of two amino acids in the hemagglutinin glycoprotein of measles virus (MV) that govern hemadsorption, HeLa cell fusion, and CD46 downregulation: phenotypic markers that differentiate vaccine and wild-type MV strains," Journal of General Virology, Jul. 1996, vol. 70, No. 7, pp. 4200-4204.
Lemon, K., et al., "Early target cells of measles virus after aerosol infection of non-human primates," PLoS Pathogens, 2011, vol. 7, e1001263, pp. 1-10.
Leonard, V.H., et al., "Measles virus blind to its epithelial cell receptor remains virulent in rhesus monkeys but cannot cross the airway epithelium and is not shed," The Journal of Clinical Investigation, 2008, vol. 118, pp. 2448-2458.
Liebert, U.G., et al., "Measles virus infections in rodents," Current Topics in Microbiology and Immunology, 1995, vol. 191, pp. 149-166.
Lopez, M., et al., "Nectin2alpha (PRR2alpha or HveB) and nectin2delta are low-efficiency mediators for entry of herpes simplex virus mutants carrying the Leu25Pro substitution in glycoprotein D," Journal of Virology, 2000, vol. 74, pp. 1267-1274.
Ludlow, M., et al., "Wild-type measles virus infection of primary epithelial cells occurs via the basolateral surface without syncytium formation or release of infectious virus," Journal of General Virology, 2010, vol. 91, pp. 971-979.
Maisner, A., et al., "Polarized budding of measles virus is not determined by viral surface glycoproteins," Journal of Virology, 1998, vol. 72, pp. 5276-5278.
McChesney, M.B., et al., "Experimental measles. I. Pathogenesis in the normal and the immunized host," Virology, 1997, vol. 233, pp. 74-84.
Mendelsohn, C.L., et al., "Cellular receptor for poliovirus: molecular cloning, nucleotide sequence, and expression of a new member of the immunoglobulin superfamily," Cell, 1989, vol. 56, pp. 855-865.
Meng, W., et al., Adherens junction: molecular architecture and regulation, Cold Spring Harbor Perspectives in Biology, 2009, vol. 1, a002899, pp. 1-13.

(56) References Cited

OTHER PUBLICATIONS

Moss, W.J., "Measles control and the prospect of eradication," Current Topics in Microbiology and Immunology, 2009, vol. 330, pp. 173-189.
Mota, H.C., "Infantile Hodgkin's disease: remission after measles" British Medical Journal, 1973, vol. 2, p. 421.
Muhlebach, M.D., et al., "Adherens junction protein nectin-4 is the epithelial receptor for measles virus," Nature, 2011, pp. 530-533, vol. 480, No. 7378.
Naniche, D., et al., "Human membrane cofactor protein (CD46) acts as a cellular receptor for measles virus," Journal of General Virology, 1993, vol. 67, pp. 6025-6032.
Naniche, D., et al., Measles virus haemagglutinin induces down-regulation of gp57/67, a molecule involved in virus binding. Journal of General Virology, 1993, vol. 74 ( Pt 6), pp. 1073-1079.
Navaratnarajah, C.K., et al., "Measles virus glycoprotein complex assembly, receptor attachment, and cell entry," Current Topics in Microbiology and Immunology, 2009, vol. 329, pp. 59-76.
Navaratnarajah, C.K., et al., "The heads of the measles virus attachment protein move to transmit the fusion-triggering signal," Nature Structural & Molecular Biology, 2011, vol. 18, pp. 128-134.
Noyce, R.S., et al., "Tumor cell marker PVRL4 (nectin 4) is an epithelial cell receptor for measles virus," PLOS Pathogens, Aug. 2011, pp. 1-24, vol. 7, No. 8.
Ploss, A., et al., "Human occludin is a hepatitis C virus entry factor required for infection of mouse cells," Nature, 2009, vol. 457, pp. 882-886.
Reymond, N., et al., "Nectin4/PRR4, a new afadin-associated member of the nectin family that trans-interacts with nectin1/PRR1 through V domain interaction," The Journal of Biological Chemistry, 2001, vol. 276, pp. 43205-43215.
Richardson, C.D., et al., "Specific inhibition of paramyxovirus and myxovirus replication by oligopeptides with amino acid sequences similar to those at the N-termini of the F1 or HA2 viral polypeptides," Virology, 1980, vol. 105, pp. 205-222.
Riley, R.C., et al., "Cutting edge: inhibiting measles virus infection but promoting reproduction: an explanation for splicing and tissue-specific expression of CD46," Journal of Immunology, 2002, vol. 169, pp. 5405-5409.
Russell, S.J., et al., "Measles virus for cancer therapy," Current Topics in Microbiology and Immunology, 2009, vol. 330, pp. 213-241.
Sakaguchi, M., et al., "Growth of measles virus in epithelial and lymphoid tissues of cynomolgus monkeys," Microbiol. Immunol., 1986, vol. 30, pp. 1067-1073.
Schneider-Schaulies, J., "Differential downregulation of CD46 by measles virus strains," Journal of Virology, 1995, vol. 69, pp. 7257-7259.
Schwartzberg, P.L., et al., "SLAM receptors and SAP influence lymphocyte interactions, development and function," Nature Reviews Immunology, 2009, vol. 9, pp. 39-46.
Shibahara, K., et al., "Increased binding activity of measles virus to monkey red blood cells after long-term passage in Vero cell cultures," Journal of General Virology, 1994, vol. 75 ( Pt 12), pp. 3511-3516.
Shirogane, Y., et al., "Epithelialmesenchymal transition abolishes the susceptibility of polarized epithelial cell lines to measles virus," J. Biol. Chem., 2010, vol. 285, pp. 20882-20890.
Sinn, P.L., et al., "Measles virus preferentially transduces the basolateral surface of well-differentiated human airway epithelia," Journal of Virology, 2002, vol. 76, pp. 2403-2409.
Tahara, M., et al., "Measles virus infects both polarized epithelial and immune cells by using distinctive receptor-binding sites on its hemagglutinin," Journal of Virology, 2008, vol. 82, pp. 4630-4637.
Tahara, M., et al., "Multiple amino acid substitutions in hemagglutinin are necessary for wild-type measles virus to acquire the ability to use receptor CD46 efficiently," Journal of General Virology, 2007, vol. 81, pp. 2564-2572.
Takano, A., et al., "Identification of nectin-4 oncoprotein as a diagnostic and therapeutic target for lung cancer," Cancer Research, 2009, vol. 69, pp. 6694-6703.
Takeda, M., et al., "A human lung carcinoma cell line supports efficient measles virus growth and syncytium formation via a SLAM- and CD46-independent mechanism," Journal of Virology, 2007, vol. 81, pp. 12091-12096.
Takeda, M., "Measles virus breaks through epithelial cell barriers to achieve transmission," The Journal of Clinical Investigation, 2008, vol. 118, No. 7, pp. 2386-2389.
Takeuchi, K., et al., "Wild-type measles virus induces large syncytium formation in primary human small airway epithelial cells by a SLAM(CD150)-independent mechanism," Virus Research, 2003, vol. 94, pp. 11-16.
Tanaka, K., et al., "The measles virus hemagglutinin downregulates the cellular receptor SLAM (CD150)," Archives of Virology, 2002, vol. 147, pp. 195-203.
Taqi, A.M., et al., "Regression of Hodgkin's disease after measles," Lancet, 1981, vol. 1, p. 1112.
Tatsuo, H., et al., "SLAM (CDw150) is a cellular receptor for measles virus," Nature, 2000, vol. 406, pp. 893-897.
Taylor, J.M., et al., "Alternative entry receptors for herpes simplex virus and their roles in disease," Cell Host Microbe., 2007, vol. 2, pp. 19-28.
Vongpunsawad, S., et al., "Selectively receptor-blind measles viruses: Identification of residues necessary for SLAM- or CD46-induced fusion and their localization on a new hemagglutinin structural model," Journal of Virology, vol. 78, pp. 302-313.
Von Messling, V., et al., "Tropism illuminated: lymphocyte-based pathways blazed by lethal morbillivirus through the host immune system," Proc Natl Acad Sci USA, 2004, vol. 101, pp. 14216-14221.
Welstead, G.G., et al., "Mechanism of CD150 (SLAM) down regulation from the host cell surface by measles virus hemagglutinin protein," Journal of Virology, 2004, vol. 78, pp. 9666-9674.
Yanagi, Y., et al., "Measles virus receptors," Current Topics in Microbiology and Immunology, 2009, vol. 329, pp. 13-30.
Yu, Z., et al., "Nectin-1 expression by squamous cell carcinoma is a predictor of herpes oncolytic sensitivity," Mol. Ther., 2007, vol. 15, pp. 103-113.
Zhu, Y.D., et al., "Experimental measles. II. Infection and immunity in the rhesus macaque," Virology, 1997, vol. 233, pp. 85-92.
Zygiert, Z., "Hodgkin's disease: remissions after measles," Lancet, 1971, vol. 1, p. 593.
PCT International Search Report and Written Opinion for PCT/IB2012/000183, May 10, 2012, 11 Pages.
Gen Bank Accession No. NM_030916, "*Homo sapiens* poliovirus receptor-related 4 (PVRL4), mRNA," NCBI, Nov. 2, 2013, 5 pages, [online] [retrieved on Dec. 11, 2013] Retrieved from the internet <URL:http://www.ncbi.nlm.nih.gov/nuccore/NM_030916>.
Gen Bank Accession No. AF426163, "*Homo sapiens* nectin 4 mRNA, complete cds," NCBI, Nov. 13, 2001, 3 pages, [online] [retrieved on Dec. 11, 2013] Retrieved from the internet <URL:http://www.ncbi.nlm.nih.gov/nuccore/AF426163>.

\* cited by examiner

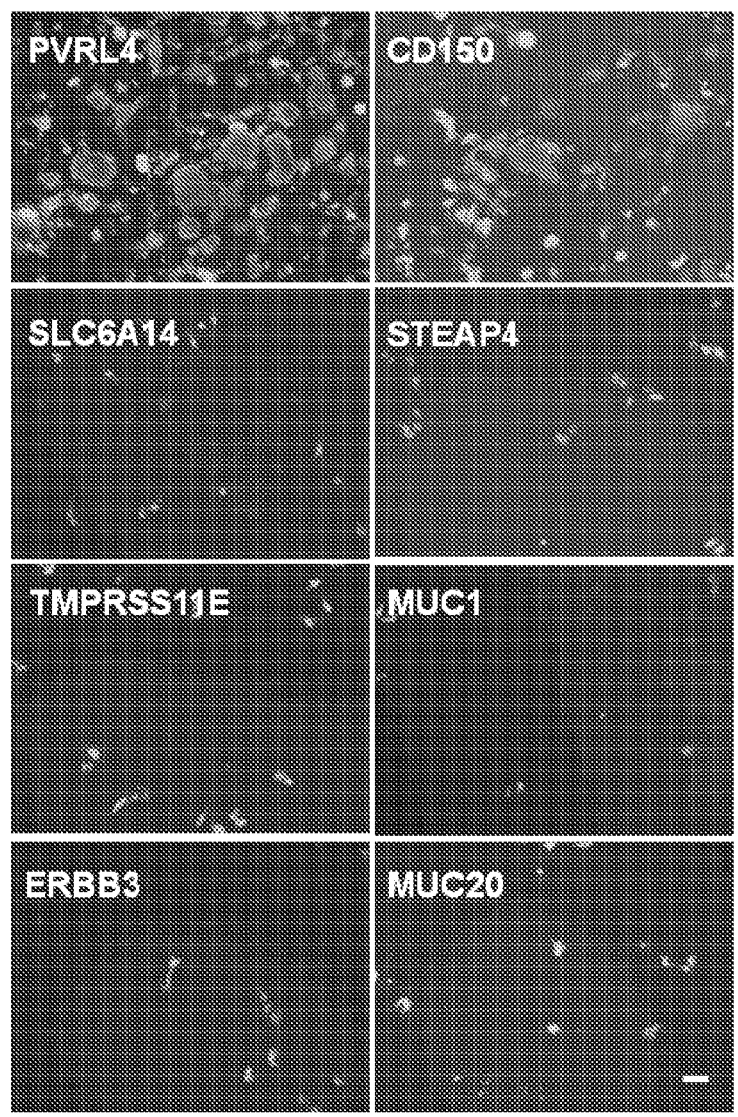
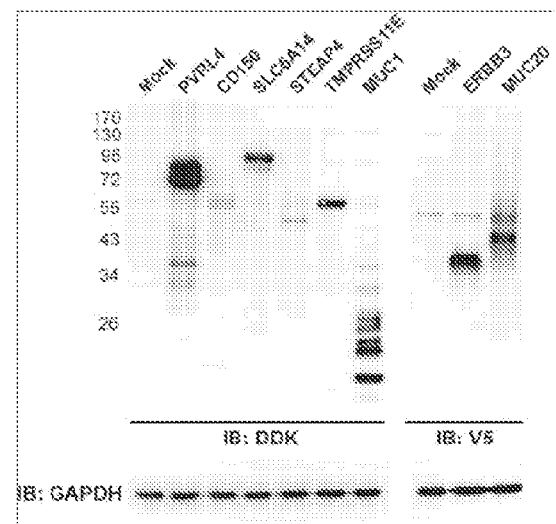
Fig. 2

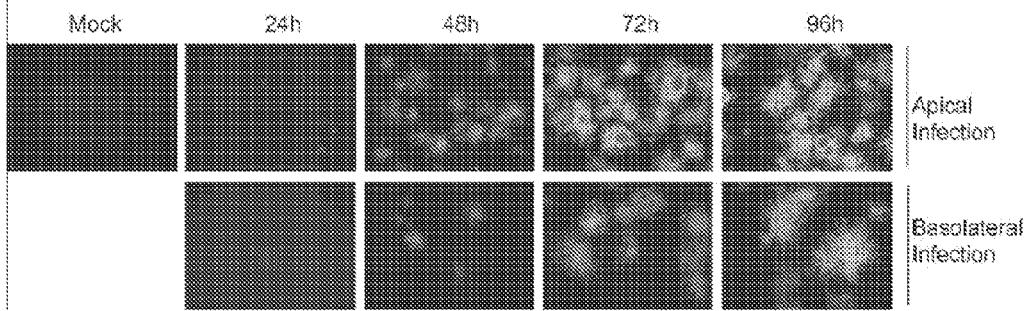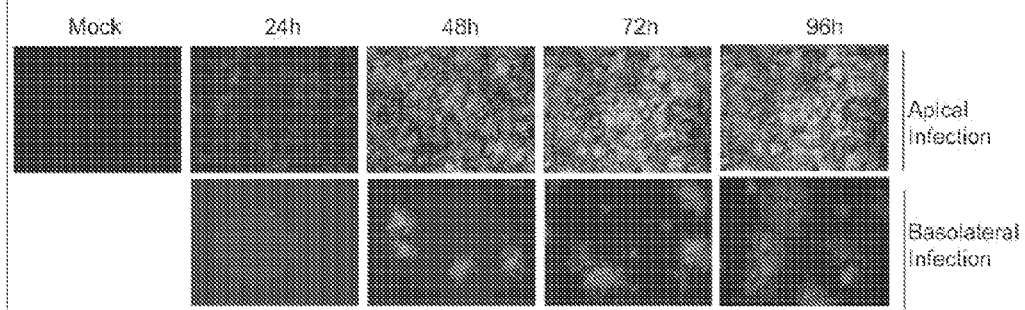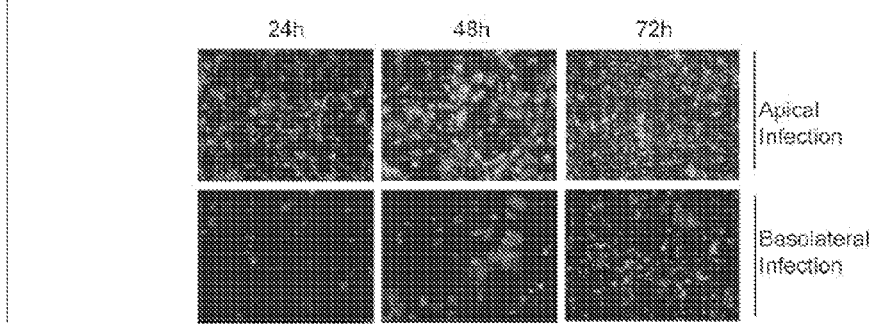
Fig. 5

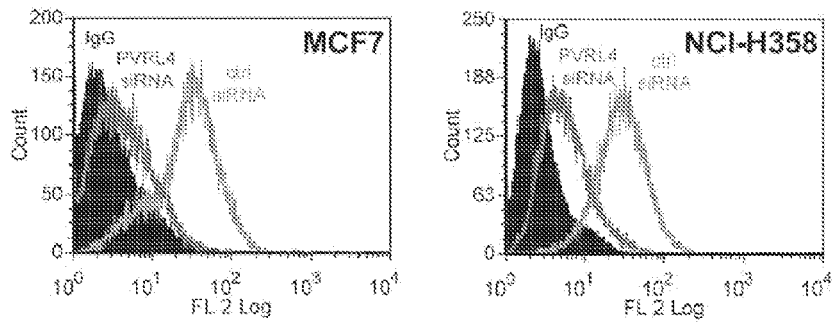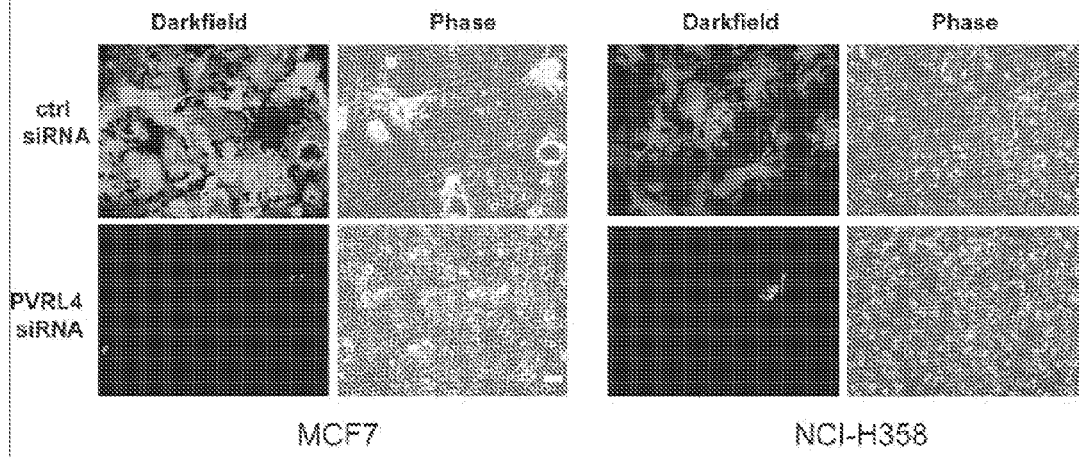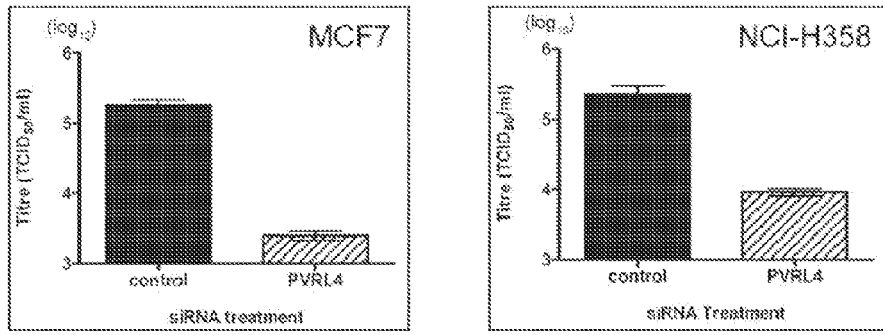
Fig. 7

Fig. 15

| | | |
|---|---|---|
| Human PVRL4.pro | MPLSLGAEMAGPEAWLLLLLLLASFTGRCPAGELETSDVVTVVLGQDAKLPCFYRGDSGE | 60 |
| Pongo PVRL4.pro | MPLSLGAEMAGPEAWLLLLLLLASFTGRCPAGELETSDVVTVVLGQDAKLPCFYRGDSGE | 60 |
| Canine PVRL4.pro | MPLSLGAEMAGPE.LLLLLLLASFTGRCP.GELETSD.VTVVLGQDAKLPCFYRGD.GE | 59 |
| Rat PVRL4.pro | MPLSLGAEMAGPEAWLLLL.L.ASFTGP..AGELETSD.VTVVLGQDAKLPCFYRGD.GE | 59 |
| Mouse PVRL4.pro | MPLSLGAEMAGPEAWL.LLL.ASFTG...AGELETSDVVTVVLGQDAKLPCFYRGD.GE | 59 |
| | | |
| Human PVRL4.pro | QVGQVAWARVDAGEGAQELALLHSKYGLHVSPAYEGRVEQPPPPRNPLDGSVLLRNAVQA | 120 |
| Pongo PVRL4.pro | QVGQVAWARVDAGEGAQELALLHSKYGLHVSPAYEGRVEQPPPPRNPLDGSVLLRNAVQA | 120 |
| Canine PVRL4.pro | QVGQVAWARVDAGEGA.ELALLHSKYGLHVS.AYEGRVEQPPPPR.PLDG.VLLRNAVQA | 119 |
| Rat PVRL4.pro | QVGQVAWARVD..EG..ELALLHSKYGLHVSPAYE.RVEQPPPPR.PLDGS.LLRNAVQA | 119 |
| Mouse PVRL4.pro | QVGQVAWARVD..EG..ELALLHSKYGLHV.PAYE.RVEQPPPPR.PLDG..LLRNAVQA | 119 |
| | | |
| Human PVRL4.pro | DEGEYECRVSTFPAGSFQARLRLRVLVPPLPSLNFGPALEEGQGLTLAASCTAEGSPAPS | 180 |
| Pongo PVRL4.pro | DEGEYECRVSTFPAGSFQARLRLRVLVPPLPSLNFGPALEEGQGLTLAASCTAEGSPAPS | 180 |
| Canine PVRL4.pro | DEGEYECRVSTFPAGSFQARLRLRVLVPPLPSLNFGPALEEGQGLTLAASCTAEGSPAPS | 179 |
| Rat PVRL4.pro | DEGEYECRYSTFPAGSFQAR.RLRVLVPPLPSLNFGP.EEGQGLTLAASCTAEGSPAPS | 179 |
| Mouse PVRL4.pro | DEGEYECRYSTFPAGSFQAR.RLRVLVPPLPSLNFGP.EEGQGLTLAASCTAEGSPAPS | 179 |
| | | |
| Human PVRL4.pro | VTWDTEVKGTTSSRSFKHSRSAAVTSEFHLVPSRSMNGQPLTCVVSHPGLLQDQRITHIL | 240 |
| Pongo PVRL4.pro | VTWDTEVKGTTSSRSFKHSRSAAVTSEFHLVPSRSMNGQPLTCVVSHPGLLQDQRITHIL | 240 |
| Canine PVRL4.pro | VTWDTEVKGT.SSRSFKHSRSAAVTSEFHLVPSRSMNGQPLTCVVSHPGLLQDQRITH.L | 239 |
| Rat PVRL4.pro | VTWDTEVKGT.A.RSFKHSRSAAVTSEFHLVPSRSMNGQPLTCVVSHPGLLQDQRITH.L | 239 |
| Mouse PVRL4.pro | VTWDTEVKGT.SSRSF.H.RSAAVTSEFHLVPSRSMNGQPLTCVVSHPGLLQD.RITH.L | 239 |
| | | |
| Human PVRL4.pro | HVSFLAEASVRGLEDQNLVHIGREGAMLKCLSEGQPPPSYNWTRLDGPLPSGVRVDGDTL | 300 |
| Pongo PVRL4.pro | HVSFLAEASVRGLEDQNLVH.GREGAMLKCLSEGQPPPSYNWTRLDGPLPSG.VDGDTL | 300 |
| Canine PVRL4.pro | .V.FLAEASVRGLEDQ.L.V..GREGA.LKCLSEG.PPPSYNWTRLDGPLPSGVRV.GDTL | 299 |
| Rat PVRL4.pro | .V.FLAEASVRGLEDQNLVH.GREGA.LKCLSEGQPPP.YNWTRLDGPLPSGVRVKGDTL | 299 |
| Mouse PVRL4.pro | .V.FLAEASVRGLEDQNLV..GREGA.LKCLSEGQPPP.YNWTRLDGPLPSGVRV.GDTL | 299 |
| | | |
| Human PVRL4.pro | GFPPLTTEHSGIYVCHVSNEFSSRDSQVTVDVLDPQEDSGKQVDLVSASVYYVGVIAALL | 360 |
| Pongo PVRL4.pro | GFPPLTTEHSGIYVCHVSNEFSSRDSQVTVDVLDPQEDSGKQVDLVSASVYYVGVIAALL | 360 |
| Canine PVRL4.pro | GFPPLT.EHSG.YVCHVSNE.SRDSQVTVDVLDPC..GKQVDLVSASVYYVGVIAALL | 358 |
| Rat PVRL4.pro | GFPPLTTEHSG.YVCHVSNE.SSR.SQVTV.VLDP.ED.GKQVDLVSASVYYVGVIAALL | 358 |
| Mouse PVRL4.pro | GFPPLTTEHSG.YVCHVSNE.SSRDSQVTV.VLDP.ED.GKQVDLVSASV..VGVIAALL | 358 |
| | | |
| Human PVRL4.pro | FCLLVVVVVLMSRYHRRKAQQMTQKYEEELTLTRENSIRRLHSHHTDPRSQPEESVGLRA | 420 |
| Pongo PVRL4.pro | FCLLVVVVVLMSRYHRRKAQQMTQKYEEELTLTRENSIRRLHSHHTDPRSQPEESVGLRA | 420 |
| Canine PVRL4.pro | FCLLVVVVVLMSRYHRRKAQQMTQKYEEELTLTRENSIRRLHSHH.DPRSQPEESVGLRA | 418 |
| Rat PVRL4.pro | FCLLVVVVVL.SRYHRRKAQQMTQKYEEELTLTRENSIRRLHSHH.DPRSQPEESVGLRA | 418 |
| Mouse PVRL4.pro | FCLLVVVVVL.SRYHRRKAQQMTQKYEEELTLTRENSIRRLHSHH.DPRSQPEESVGLRA | 418 |
| | | |
| Human PVRL4.pro | EGHPDSLKDNSSCSVMSEEPEGRSYSTLTTVREIETQTELLSPGSGRAEEEEDQDEGIKQ | 480 |
| Pongo PVRL4.pro | EGHPDSLKDNSSCSVMSEEPEGRSYSTLTTVREIETQTELLSPGSGRAEEEEDQDEGIKQ | 479 |
| Canine PVRL4.pro | EGHPDSLKDNSSCSVMSEEPEGRSYSTLTTVREIETQTELLSPGSGRAEEEED.DEGIKQ | 479 |
| Rat PVRL4.pro | EGHPDSLKDNSSCSVMSEEPEGRSYSTLTTVREIETQTELLSPGSGR.EEEEDQDEGIKQ | 478 |
| Mouse PVRL4.pro | EGHPDSLKDNSSCSVMSEEPEGRSYSTLTTVREIETQTELLSPGSGR.EE..DQDEGIKQ | 478 |
| | | |
| Human PVRL4.pro | AMNHFVQENGTLRAKPTGNGIYINQRGHLV | 510 |
| Pongo PVRL4.pro | AMNHFVQENGTLRAKPTGNGIYINQRGHLV | 509 |
| Canine PVRL4.pro | AMNHFVQENGTLRAKPTGNGIYINQRGHLV | 509 |
| Rat PVRL4.pro | AMNHFVQENGTLRAKPTGNGIYINQRGHLV | 508 |
| Mouse PVRL4.pro | AMNHFVQENGTLRAKPTGNGIYINQRGHLV | 508 |

Fig. 17

PVRL4 (NECTIN4) IS A RECEPTOR FOR MEASLES VIRUS

CROSS REFERENCE TO RELATED APPLICATIONS

This application claims the benefit of U.S. Provisional Application No. 61/433,679, filed Jan. 18, 2011, which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Jan. 12, 2015, is named 97510-921417 (000300US)_SL.txt and is 36,161 bytes in size. Please insert the accompanying paper copy of the Sequence Listing, page numbers 1 to 18, at the end of the application.

BACKGROUND

In spite of the success of an attenuated measles virus (MV) vaccine in the modern world [1] measles virus (MV) is still a major killer of children in developing countries [2]. MV strikes an estimated 20 million children a year and killed around 164,000 individuals in 2008 according to the World Health Organization. MV causes an acute disease characterized by fever, photophobia, coughing, running nose, nausea, and a macular red rash over most of the body. In rare instances, persistent MV infections can occur in the brain and lead to encephalitis. Humans and monkeys are hosts for MV [3,4,5,6,7] while most rodents are not normally infected by the virus [8,9,10]. The recent discovery that attenuated strains of MV possess oncolytic properties and can be used to destroy tumor cells, has kindled an interest in this virus as a gene therapy agent [11,12].

Measles virions contain a negative strand RNA genome from which viral mRNA's are transcribed to encode a nucleocapsid protein (NP), a phosphoprotein (P), virulence factors (C and V), matrix protein (M), membrane fusion protein (F), the hemagglutinin/receptor binding protein (H), and an RNA polymerase (L) [13]. Surrounding the nucleocapsid is a membrane which contains the two viral glycoproteins, H and F. The H protein is required for viral attachment to the host cell receptor, while F mediates membrane fusion and entry at the host plasma membrane and is also responsible for syncytia (multi-nucleated cell) formation.

Interaction of the H protein of MV with a cellular attachment factor is the initial event of infection. The binding of H to the host cell receptor triggers and activates the F protein to induce fusion between virus and host cell membranes [14,15,16]. The search for MV cellular receptors initially began with vaccine/laboratory strains and progressed to more relevant receptors used by wild type MV (wtMV) isolates [17]. Human membrane cofactor protein (MCP/CD46) is a receptor for the Edmonston laboratory/vaccine strain of MV [18,19]. CD46 is a complement regulatory protein that is expressed on most cell types in the human body, with the exception of red blood cells (although it is on monkey erythrocytes) [20]. Natural isolates of wtMV can be adapted to grow in Vero monkey kidney cells and this is accompanied by mutations in the H protein that convey the CD46 receptor binding phenotype [21,22,23]. Strains of wtMV are routinely isolated in marmoset B95-8 cells, a B cell line immortalized with Epstein-Barr virus, which allows the virus to grow without the need for adaptation [24]. These isolates cannot use CD46 as a receptor [22,25]. Our laboratory and others hypothesized that another lymphotropic receptor could be used by wild type isolates of MV [22,26,27]. Signaling lymphocyte activation molecule (SLAM) or CD150 was identified to be a lymphotropic receptor for both clinical isolates and vaccine strains of MV [28,29,30]. SLAM/CD150 is a signaling molecule that is expressed on activated B, T, monocyte, and dendritic cells [31].

Recent evidence indicates that CD150$^+$ alveolar macrophages, dendritic cells, and lymphocytes are the initial targets for measles virus infections in macaques [32,33,34,35]. However, wild type MV, in autopsied human patients and some experimentally infected monkeys, has been shown to infect the epithelial cells of the trachea, bronchial tubes, lungs, oral cavity, pharynx, esophagus, intestines, liver, and bladder [36, 37]. These epithelial cells do not express SLAM/CD150, but the infected cells do shed virus [37,38,39]. Epithelial cells may be important later on in infection and for the spread of MV by aerosol droplets. Wild type MV does not readily infect most common laboratory epithelial, endothelial, or fibroblast cell lines. In addition, cryo-preserved primary human small airway epithelial cells (SAEC) grown in serum free epithelial cell growth medium are not normally susceptible to wtMV, but can be made susceptible by culturing them in 2% fetal calf serum [39]. These cells do not express CD150/SLAM and the wtMV cannot use CD46/MCP, suggesting that there is another receptor on epithelial cells [39]. Other investigators have been searching for an elusive receptor on polarized epithelial and cancer cell lines [41,44,45,46].

Herein it is shown that wild type measles virus infects primary airway epithelial cells grown in fetal calf serum and many adenocarcinoma cell lines of the lung, breast, and colon. A microarray analysis of permissive versus non-permissive cell lines showed that transcripts for many adherens junction and tight junction proteins were up-regulated in virus susceptible cells. However, the integrity of these junctions was not a prerequisite for infection. Non-permissive cell lines could be infected following transfection with a CD150/SLAM expression vector, indicating that they were replication competent. Analysis of the microarray data, filtered for membrane protein genes, produced a short list of 11 candidate receptors. Of these only human PVRL4 (Nectin 4), a tumor cell marker found on breast, lung, and ovarian carcinomas, rendered cells permissive to measles virus infections. Antibodies directed against PVRL4 or PVRL4 siRNA's abolished wtMV infection.

SUMMARY

Disclosed herein is a method for reducing the size of a tumor in a mammal having a tumor, comprising: determining that the tumor expresses poliovirus receptor-related 4 (PVRL4; Nectin 4); and administering a measles virus or a related canine distemper virus to the mammal under conditions wherein the size of the tumor is reduced.

Also disclosed herein is a method of treating a tumor in a patient having the tumor, comprising determining that the tumor expresses PVRL4; and administering a therapeutically effective dose of a measles virus to the patient so as to reduce the number of tumor cells in the patient.

Also disclosed herein is a method of treating a tumor in a patient having the tumor, comprising determining that the tumor expresses PVRL4; administering a therapeutically effective dose of a measles virus to the patient so as to reduce the number of tumor cells in the patient, wherein said tumor cells are part of a tumor; and monitoring a reduction of the size of the tumor.

In some aspects, the PVRL4 expression level is determined to be increased compared to the PVRL4 expression level of a control sample, wherein the virus is a measles virus and is injected directly into the tumor, wherein the mammal is a human, and wherein the tumor is an adenocarcinoma. In some aspects, the PVRL4 expression level is determined to be increased compared to the PVRL4 expression level of a control sample. In some aspects, the virus is injected directly into the tumor.

In some aspects, the virus is provided in a formulation comprising an excipient. In some aspects, the virus is provided in a formulation comprising an excipient, and wherein the virus formulation is provided continuously to the mammal. In some aspects, the virus is provided in a formulation comprising an excipient, and wherein the virus formulation is provided in pulses to the mammal.

In some aspects, the virus is administered systemically to the mammal. In some aspects, the virus is administered at a dose greater than about $10^3$ plaque forming units (pfus), about $10^5$ pfus, about $10^6$ pfus, about $10^7$ pfus, or about $10^8$ pfus.

In some aspects, the virus is provided in a composition further comprising attenuated mumps virus and attenuated rubella virus. In some aspects, the virus is provided in a composition further comprising attenuated rubella virus. In some aspects, the tumor is selected from the group consisting of an adenocarcinoma tumor, a melanoma tumor, a carcinoma tumor, a glioma tumor, and a myeloma tumor. In some aspects, the virus is provided within a vaccine formulation.

In some aspects, the virus is a related canine distemper virus, a canine distemper virus, a related *morbillivirus*, a *morbillivirus*, a phocine distemper *morbillivirus*, a peste des petits ruminants virus (PPRV); a goat virus, or a virus comprising an H protein that comprises a PVRL4 binding site.

In some aspects, the virus delivers protein H. In some aspects, the virus delivers wild-type protein H. In some aspects, the virus is selected from the group consisting of the Edmonston Zagreb measles strain, the Edmonston-Enders strain, the Moraten strain, and the Moraten Berna strain. In some aspects, the virus is administered intravenously. In some aspects, the virus is cytolytic. In some aspects, the virus causes cell death through syncytia and/or apoptosis. In some aspects, the virus induces an immune response against the tumor. In some aspects, the virus induces an immune response against the tumor, and wherein the immune response is directed against one or more virus antigens.

Also disclosed herein is a method of infecting a cell with a virus, comprising determining that the cell expresses PVRL4 and contacting the cell with the virus, wherein the virus is a measles virus or a related canine distemper virus. In some aspects, the cell is a cancer cell. In some aspects, the method is performed in vitro. In some aspects, PVRL4 expression is determined by a nucleotide-based assay or an antibody-based assay.

Also disclosed herein is a method of infecting a PVRL4 expressing cell with a virus, comprising obtaining a cell predetermined to expresses PVRL4; and contacting the cell with the virus, wherein the virus is a measles virus or a related canine distemper virus. In some aspects, the cell is a cancer cell. In some aspects, the method is performed in vitro. In some aspects, PVRL4 expression is determined by a nucleotide-based assay or an antibody-based assay. In some aspects, the cell is predetermined to express PVRL4 by a third party.

Also disclosed herein is a method for infecting a PVRL4 expressing cell with a virus, comprising contacting the cell with a measles virus or a related canine distemper virus under conditions wherein the cell is infected by the virus, wherein the cell has been predetermined to express PVRL4. In some aspects, the cell is a cancer cell. In some aspects, the method is performed in vitro. In some aspects, PVRL4 expression is determined by a nucleotide-based assay or an antibody-based assay. In some aspects, the cell is predetermined to express PVRL4 by a third party.

Also disclosed herein is a method for reducing the size of a tumor in a subject having a tumor, comprising administering a measles virus or a related canine distemper virus to the subject under conditions wherein the size of the tumor is reduced, wherein the subject's tumor has been predetermined to express PVRL4. In some aspects, PVRL4 expression is determined by a nucleotide-based assay or an antibody-based assay. In some aspects, the subject is predetermined to express PVRL4 by a third party.

Also disclosed herein is a method for infecting a PVRL4 expressing cell in a subject in need thereof, comprising administering a measles virus or a related canine distemper virus to the subject under conditions wherein the cell is infected by the virus, wherein the subject has been predetermined to have one or more cells expressing PVRL4. In some aspects, PVRL4 expression is determined by a nucleotide-based assay or an antibody-based assay. In some aspects, the subject is predetermined to express PVRL4 by a third party.

Also disclosed herein is a method for identifying a subject in need of measles virus treatment, comprising: obtaining a first dataset associated with a sample obtained from the subject, wherein the first dataset comprises quantitative expression data for PVRL4; and analyzing the first dataset to determine the expression level of PVRL4, wherein the expression level of PVRL4 positively correlates with an increased likelihood the subject is in need of measles virus treatment.

In some aspects, the first dataset further comprises quantitative expression data for at least two, three, four, five, six, seven, eight, nine, ten, eleven, twelve, thirteen, fourteen, fifteen, sixteen, seventeen, eighteen, nineteen, twenty or more markers. In some aspects, the analysis further comprises comparing the first dataset to a second dataset associated with a control sample, wherein the second dataset comprises quantitative expression data for a control marker, and wherein a statistically significant difference between expression of PVRL4 and expression of the control marker indicates an increased likelihood the subject is in need of measles virus treatment. In some aspects, the control sample is associated with a control subject or with a control population. In some aspects, expression of PVRL4 is significantly increased compared to expression of the control marker. In some aspects, the subject has cancer. In some aspects, the sample is a tumor sample. In some aspects, the control sample is associated with a control subject or a control population characterized by absence of cancer.

In some aspects, the method is implemented on one or more computers. In some aspects, the first dataset is obtained stored on a storage memory. In some aspects, obtaining the first dataset associated with the sample comprises obtaining the sample and processing the sample to experimentally determine the first dataset. In some aspects, obtaining the first dataset associated with the sample comprises receiving the first dataset directly or indirectly from a third party that has processed the sample to experimentally determine the first dataset. In some aspects, the quantitative expression data is obtained from a nucleotide-based assay. In some aspects, the quantitative expression data is obtained from an RT-PCR assay, a sequencing-based assay, or a microarray assay. In some aspects, the quantitative expression data is obtained from an antibody-based assay. In some aspects, the subject is a human subject.

Also disclosed herein is a method for identifying whether a cell can be infected with a measles virus, comprising: obtaining a first dataset associated with a sample obtained from the cell, wherein the first dataset comprises quantitative expression data for PVRL4; and analyzing the first dataset to determine the expression level of PVRL4, wherein the expression level of PVRL4 positively correlates with an increased likelihood the cell can be infected by measles virus.

In some aspects, the cell is obtained from a subject. In some aspects, the first dataset further comprises quantitative expression data for at least two, three, four, five, six, seven, eight, nine, ten, eleven, twelve, thirteen, fourteen, fifteen, sixteen, seventeen, eighteen, nineteen, twenty or more markers.

In some aspects, the analysis further comprises comparing the first dataset to a second dataset associated with a control sample, wherein the second dataset comprises quantitative expression data for a control marker, and wherein a statistically significant difference between expression of PVRL4 and expression of the control marker indicates an increased likelihood the cell can be infected by measles virus. In some aspects, the control sample is associated with a control subject, control cell, or with a control population. In some aspects, expression of PVRL4 is significantly increased compared to expression of the control marker. In some aspects, the cell is a cancer cell. In some aspects, the sample is a tumor sample. In some aspects, the control sample is associated with a control subject or a control population characterized by absence of cancer.

In some aspects, the method is implemented on one or more computers. In some aspects, the first dataset is obtained stored on a storage memory. In some aspects, obtaining the first dataset associated with the sample comprises obtaining the sample and processing the sample to experimentally determine the first dataset. In some aspects, obtaining the first dataset associated with the sample comprises receiving the first dataset directly or indirectly from a third party that has processed the sample to experimentally determine the first dataset. In some aspects, the quantitative expression data is obtained from a nucleotide-based assay. In some aspects, the quantitative expression data is obtained from an RT-PCR assay, a sequencing-based assay, or a microarray assay. In some aspects, the quantitative expression data is obtained from an antibody-based assay. In some aspects, the cell is a human adenocarcinoma cell.

Also disclosed herein is a method for determining whether a subject is in need of measles virus treatment, comprising: obtaining a sample from the subject, wherein the sample comprises PVRL4; contacting the sample with a reagent; generating a complex between the reagent and PVRL4; detecting the complex to obtain a first dataset associated with the sample, wherein the first dataset comprises quantitative expression data for PVRL4; and analyzing the first dataset to determine the expression level of PVRL4, wherein the expression level of PVRL4 positively correlates with an increased likelihood the subject is in need of measles virus treatment.

Also disclosed herein is a computer-implemented method for identifying a subject in need of measles virus treatment, comprising: storing, in a storage memory, a first dataset associated with a sample obtained from the subject, wherein the first dataset comprises quantitative expression data for PVRL4; and analyzing, by a computer processor, the first dataset to determine the expression level of PVRL4, wherein the expression level of PVRL4 positively correlates with an increased likelihood the subject is in need of measles virus treatment.

Also disclosed herein is a system for determining whether a subject is in need of measles virus treatment, the system comprising: a storage memory for storing a first dataset associated with a sample obtained from the subject, wherein the first dataset comprises quantitative expression data for PVRL4; and a processor communicatively coupled to the storage memory for analyzing the first dataset to determine the expression level of PVRL4, wherein the expression level of PVRL4 positively correlates with an increased likelihood the subject is in need of measles virus treatment.

Also disclosed herein is a computer-readable storage medium storing computer-executable program code, the program code comprising: program code for storing a first dataset associated with a sample obtained from a subject, wherein the first dataset comprises quantitative expression data for PVRL4; and program code for analyzing the first dataset by comparing the first dataset to a control dataset to determine the expression level of PVRL4, wherein the expression level of PVRL4 positively correlates with an increased likelihood the subject is in need of measles virus treatment.

Also disclosed herein is a kit for use in determining whether a subject is in need of measles virus treatment, comprising: a set of reagents comprising a plurality of reagents for determining from a sample obtained from the subject quantitative expression data for PVRL4; and instructions for using the plurality of reagents to determine quantitative expression data from the sample and analyzing the first dataset to determine the expression level of PVRL4, wherein the expression level of PVRL4 positively correlates with an increased likelihood the subject is in need of measles virus treatment. In some aspects, the instructions further comprise instructions for conducting a nucleotide-based assay or an antibody-based assay.

Also disclosed herein is a kit for use in determining whether a subject is in need of measles virus treatment, comprising: a set of reagents consisting essentially of a plurality of reagents for determining from a sample obtained from the subject quantitative expression data for PVRL4; and instructions for using the plurality of reagents to determine quantitative expression data for PVRL4 from the sample. In some aspects, the instructions further comprise instructions for conducting a nucleotide-based assay or an antibody-based assay.

Also disclosed herein is a method for identifying whether a cell can be infected with a measles virus, comprising: obtaining a sample from the cell, wherein the sample comprises PVRL4; contacting the sample with a reagent; generating a complex between the reagent and PVRL4; detecting the complex to obtain a first dataset associated with the sample, wherein the first dataset comprises quantitative expression data for PVRL4; and analyzing the first dataset to determine the expression level of PVRL4, wherein the expression level of PVRL4 positively correlates with an increased likelihood the cell can be infected with measles virus.

Also disclosed herein is a computer-implemented method identifying whether a cell can be infected with a measles virus, comprising: storing, in a storage memory, a first dataset associated with a sample obtained from the cell, wherein the first dataset comprises quantitative expression data for PVRL4; and analyzing, by a computer processor, the first dataset to determine the expression level of PVRL4, wherein the expression level of PVRL4 positively correlates with an increased likelihood the cell can be infected with measles virus.

Also disclosed herein is a system for identifying whether a cell can be infected with a measles virus, the system comprising: a storage memory for storing a first dataset associated with a sample obtained from the cell, wherein the first dataset comprises quantitative expression data for PVRL4; and a processor communicatively coupled to the storage memory for analyzing the first dataset to determine the expression level of PVRL4, wherein the expression level of PVRL4 positively correlates with an increased likelihood the cell can be infected with measles virus.

Also disclosed herein is a computer-readable storage medium storing computer-executable program code, the program code comprising: program code for storing a first dataset associated with a sample obtained from a cell, wherein the first dataset comprises quantitative expression data for PVRL4; and program code for analyzing the first dataset by comparing the first dataset to a control dataset to determine the expression level of PVRL4, wherein the expression level of PVRL4 positively correlates with an increased likelihood the cell can be infected with measles virus.

Also disclosed herein is a kit for use in identifying whether a cell can be infected with a measles virus, comprising: a set of reagents comprising a plurality of reagents for determining from a sample obtained from the cell quantitative expression data for PVRL4; and instructions for using the plurality of reagents to determine quantitative expression data from the sample and analyzing the first dataset to determine the expression level of PVRL4, wherein the expression level of PVRL4 positively correlates with an increased likelihood the cell can be infected with measles virus.

Also disclosed herein is a method of interfering with a measles virus infection in a subject in need thereof, comprising administering a PVRL4 binding agent to the subject, wherein administration of the agent to the subject results in interference with the measles virus infection process in the subject. In some aspects, the agent is a PVRL4 specific antibody. In some aspects, the agent is a PVRL4 specific double stranded RNA (dsRNA), such as an siRNA.

Also disclosed herein is a method of treating a subject having a measles virus infection, comprising administering a PVRL4 binding agent to the subject, wherein administration of the agent to the subject blocks measles virus infection. In some aspects, the agent is a PVRL4 specific antibody. In some aspects, the agent is a PVRL4 specific double stranded RNA (dsRNA), such as an siRNA.

Also disclosed herein is a method of interfering with a measles virus infection of a PVRL4 expressing cell, comprising contacting the cell with a PVRL4 binding agent, wherein the contacting results in interference with the measles virus infection process. In some aspects, the agent is a PVRL4 specific antibody. In some aspects, the agent is a PVRL4 specific double stranded RNA (dsRNA), such as an siRNA.

Also disclosed herein is a method for identifying a compound which binds to PVRL4 comprising: a) incubating components comprising the compound and PVRL4 under conditions sufficient to allow the components to interact; and b) measuring the binding of the compound to PVRL4. In some aspects, the method further comprises (c) contacting the components of (a) with measles virus, wherein PVRL4 is expressed in a cell; and (d) measuring the ability of the compound to block viral infection of the cell. In some aspects, PVRL4 is PVRL4 protein. In some aspects, PVRL4 is PVRL4 mRNA.

Also disclosed herein is a method for identifying a compound which interferes with measles virus infection comprising: a) incubating components comprising the compound and a PVRL4 expressing cell under conditions sufficient to allow the components to interact; (b) contacting the components of (a) with measles virus; and (c) measuring the ability of the compound to block viral infection of the cell.

Also disclosed herein is a method for identifying a compound which blocks measles virus infection, comprising: incubating components comprising the compound with a PVRL4 positive cell under conditions sufficient to allow the components to interact with the PVRL4 positive cell; contacting the components and the PVRL4 positive cells with measles virus or a measles virus infected cell; and measuring the ability of the compound to block viral infection of the PVRL4 positive cell.

BRIEF DESCRIPTION OF THE SEVERAL VIEWS OF THE DRAWINGS

These and other features, aspects, and advantages will become better understood with regard to the following description, and accompanying drawings, where:

FIG. 2. PVRL4 (Nectin 4) can function as an entry factor for IC323-EGFP wtMV. COS-1 cells were transfected with expression plasmids containing the coding sequences for candidate membrane protein receptors. After 36 hrs the cells were infected with IC323-EGFP wtMV. Virus specific fluorescence was observed between 24-48 hrs infection at 100× magnification using a Leica inverted microscope. Both PVRL4 (Nectin 4) and the positive control CD150/SLAM were capable of converting the non-susceptible COS-1 cells to a virus susceptible phenotype that produced syncytia. Other candidate receptor proteins including SLC6A14, STEAP4, TMPRSS11E, MUC1, ERBB3, and MUC20 were ineffective in producing infections, and yielded only isolated background single-cell infections that did not produce syncytia. Whole cell protein lysates were separated by SDS-PAGE followed by Western Immunoblot using Flag (IB: DDK) and V5 (IB: V5) antibodies to detect expression of these candidate receptors. GAPDH was used as a loading control. Scale bar=100 µm. See also FIGS. 13 and 14.

FIG. 5. MV infects polarized adenocarinoma cells via either the apical or basolateral surfaces. Wild type IC323 MV infects (A) MCF7 (breast), (B) NCI-H358 (lung) adenocarcinoma and (C) CHO-PVRL4 cell lines via the apical and basolateral surface in Transwell filter assays. Cells were cultivated in Transwell permeable filter supports at a density of $7.0 \times 10^5$ cells per Transwell filter (24 mm diameter) for 4 days (MCF7 & NCI-H358) or 2 days (CHO-PVRL4). Cells were then infected from either the apical or basolateral side with IC323-EGFP wtMV. At various times post infection fluorescent images were captured. Scale bar=500 µm.

FIG. 7. siRNA specific for human PVRL4 inhibits wtMV infections. MCF7 and NCI-H358 cells were transfected with a scrambled oligonucleotide control (ctrl siRNA) or a siRNA pool specific for PVRL4 (PVRL4 siRNA). The transfected cells were incubated with IC323-EGFP wtMV and images were captured 48 hr post infection. (A) PVRL4 surface expression was detected with a phycoerythrin conjugated PVRL4 antibody following gene knockdown with control siRNA (far right line) or PVRL4 siRNA (middle line). (B) PVRL4 siRNA-treated MCF7 and NCI-H358 cells showed less GFP expression compared to ctrl siRNA-treated cells. (C) PVRL4 knockdown results in a decrease in wtMV titres in MCF7 and NCI-H358 cells. Forty-eight hours post infection, cells were harvested and $TCID_{50}$ virus titrations were performed on Vero-SLAM cells. Data are the means from three independent experiments, and error bars represent the SEM. Scale bar=100 µm.

FIG. 15. Comparison of protein sequences for human PVRL1, PVRL2, PVRL3, and PVRL4 (SEQ ID NOS 1-4, respectively). Sequences were aligned using the Clustal method from the DNAStar Lasergene analysis software. Shaded residues represent amino acids that are identical to the consensus sequence shared by the 4 proteins. PVRL4 exhibits 38% identity with the consensus. Sequences were obtained from the NCBI GeneBank. [PVRL1NM_002855.4; PVRL2 NM_002856.2; PVRL3 NM_015480,1; PVRL4 NM_030916.2]. See also FIG. 3.

FIG. 17. Comparison of protein sequences for human, orangutan (pongo), canine, rat, and mouse PVRL4 (Nectin 4) (SEQ ID NOS 4-8, respectively). Sequences were aligned using the Clustal method from the DNAStar Lasergene analysis software. Shaded residues represent differences from the human sequence. Human and orangutan sequences were almost 100% identical. Mouse and rat sequences were 92% identical to that of humans. The canine PVRL4 sequence was 95% identical to the human sequence. Sequences were obtained from the NCBI GeneBank. [Human NM_030916.2; Orangutan(Pongo) XM_002809905.1; Cow NM_001024494.1; Dog XM_847277.1; Rat NM_001109076.1; Mouse NM_027893.3]. See also FIG. 9.

DETAILED DESCRIPTION

Figure 1:
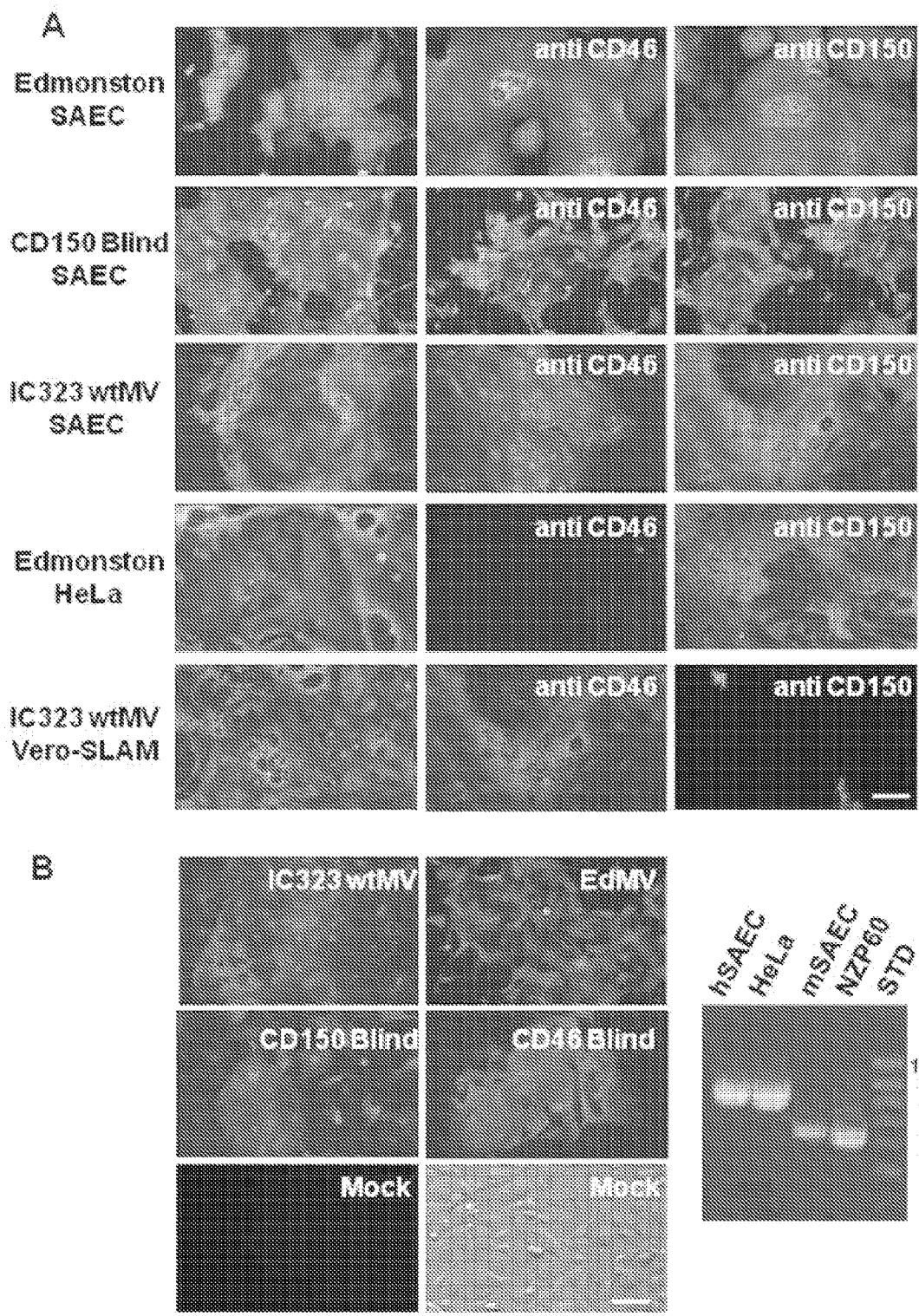
FIG. 1. A new receptor for MV is present on smooth airway epithelial cells (SAEC). (A) Human SAEC were incubated with receptor neutralizing antibodies against CD46 (M75 and B97) or CD150 (IPO-3 and A12) and challenged with the Edmonston vaccine, CD150 Blind, or IC323 wild type strains of MV. Each virus strain contained the EGFP reporter gene. In virus control experiments antibodies against CD46 inhibited infection by Edmonston MV in HeLa cells while antibodies against CD150 blocked infection of Vero-CD150/SLAM by wild type IC323 MV. (B) Marmoset SAEC contain a deletion of the SCR1 domain of CD46 and do not express CD150/SLAM. The panel on the right shows a diagnostic PCR spanning the SCR1 domain revealed by agarose gel electorphoresis in the presence of ethidium bromide, that confirms the deletion in marmoset SAEC. However, the marmoset SAEC could be infected with either the Edmonston or IC323 strains of MV. Virus containing H protein that was mutated in either its CD150 binding site (CD150 Blind) or its CD46 binding site (CD46 Blind) also replicated in the marmoset SAEC. Scale bar=100 µm.

Terms used in the claims and specification are defined as set forth below unless otherwise specified.

As used herein, the term "ameliorating" refers to any therapeutically beneficial result in the treatment of a disease state, e.g., a cancerous disease state, including prophylaxis, lessening in the severity or progression, remission, or cure thereof.

As used herein, the term "in situ" refers to processes that occur in a living cell growing separate from a living organism, e.g., growing in tissue culture.

As used herein, the term "in vivo" refers to processes that occur in a living organism.

As used herein, the term "mammal" as used herein includes both humans and non-humans and include but is not limited to humans, non-human primates, canines, felines, murines, bovines, equines, and porcines.

As used herein, the term "measles virus" is a paramyxovirus of the genus *Morbillivirus*. Morbilliviruses, like other paramyxoviruses, are generally known to be enveloped, single-stranded, negative-sense RNA viruses. In some aspects, a measles virus can include other related viruses, e.g., a canine distemper virus. In some aspects, a measles virus includes a virus engineered to express a measles protein that interacts with PVRL4. In some aspects, a measles virus includes a virus engineered to express a measles virus wild-type H protein or engineered to express a virus H protein blind to CD46.

As defined herein, the term "attenuated" means a virus which is immunologically related to the wild type measles virus (i.e., the virulent virus) but which is not itself pathogenic and does not produce a "classical measles disease," and is not a wild type virus. An attenuated measles virus is replication-competent, in that it is capable of infecting and replicating in a host cell without additional viral functions supplied by, for example, a helper virus or a plasmid expression construct encoding such additional functions.

As used herein and when used in the context of viral infection of a cell, the terms "block", "interfere", "inhibit" refer to a reduction in the ability of a virus to infect a cell as compared to a control. For example, if a PVRL4-binding agent interferes with viral infection of a cell this can mean that the ability of a virus (such as a measles virus) to infect a cell contacted with the agent is reduce relative to a control cell that was not contacted with the agent or that was instead contacted with a control agent, such as a non-specific antibody.

As used herein, the terms "wild-type" or "wild-type virus" refer to the characteristics of a measles virus as it is found in nature which is pathogenic.

As used herein, a "pathogenic measles virus" is one which produces classical measles disease.

As defined herein, "classical measles disease" is a syndrome comprising fever, coryza, cough, conjunctivitis, followed by the appearance of a maculopaular rash (Koplik spots) which occurs upon infection with a wild type measles virus in an individual who is not immune to the virus.

As used herein, the terms "patient" or "subject" refers to an organism to which viruses can be administered. Preferably, a patient is a mammal, e.g., a human, primate or a rodent. The term "subject" also encompasses a cell, tissue, or organism, human or non-human, whether in vivo, ex vivo, or in vitro, male or female.

As used herein, the term "biological fluid" refers to any extracellular bodily fluid, including but not limited to blood, urine, saliva, interstitial fluid, lymph, and cerebrospinal fluid.

As used herein, the term "administering directly to a group of cancer cells" or "administering directly to a tumor" refers to injecting or implanting a source of measles virus either in proximity to (within 1-2 cm) of, or within a tumor.

As used herein, the term "administering systemically" refers to exposure of the cells of an organism to a measles virus via the circulatory system of the patient, such as by intravenous injection or the use of a medical access device, such as a catheter.

As defined herein, "plaque forming units" or "pfus" refers to areas of destroyed cells in a cell culture infected with a virus.

As defined herein, "primary isolation of measles virus" refers to isolation and culture of a measles virus from an infected patient in order to develop an attenuated strain.

As used herein, the term "recombinant virus" or "modified virus" refers to a virus or viral polypeptide which is altered by genetic engineering, by modification or manipulation of the genetic material encoding that polypeptide, or found in the virus such that it is not identical to the naturally occurring virus or polypeptide.

As used herein, the term "detectable" refers to a property of a polypeptide that allows one to determine the presence and/or amount of the polypeptide in a biological sample. The meaning of the term "detectable" is intended to encompass detection of activities, for example, enzyme activity or fluorescence activity possessed by the polypeptide, in addition to detection of the polypeptide by other means, for example, immunoassay or mass spectroscopy.

As used herein, "measles virus growth" refers to growth or replication of a measles virus measured by viral propagation after successive rounds of infection and replication occurring in a host organism, as measured by virus titer, or by detection of a marker polypeptide, or as measured by a reduction in tumor size.

As used herein, "reduction in size in a group of cancer cells" or "reduction in size of a tumor" refers to any decrease in the size of a group of cancer cells or a tumor following administration of a measles virus relative to the size of the group of cancer cells or tumor prior to administration of the virus. A group of cancer cells or tumor may be considered to be reduced in size or regressed if it is at least about 10% smaller, 25%, 50%, up to 100%, or having no cancer cells or tumor remaining. Size is measured either directly or in vivo (i.e., by measurement of the group of cancer cells or a tumor which is directly accessible to physical measurement, such as by calipers) or by examination of the size of an image of the tumor produced, for example, by X-ray or magnetic resonance imaging or by computerized tomography, or from the assessment of other optical data (e.g., spectral data).

As defined herein, "reduction in number of cancer cells" refers at least a 10% reduction in the number of cancer cells. For a tumor, reduction in number can be measured as a reduction in size or weight of a tumor, or a reduction in the amount of a tumor specific antigen of at least 10%. For a group of cancer cells, such as a group of leukemia cells, a reduction in number can be determined by measuring the absolute number of leukemia cells in the circulation of a patient, or a reduction in the amount of a cancer cell-specific antigen of at least 10%.

As defined herein, "regression of a group of cancer cells" or "regression of a tumor" refers to a decrease in the size of a group of cancer cells/tumor as described above, and/or as a decrease in the levels of a cancer cell antigen in the patient.

As defined herein, "limiting the growth of a group of cancer cells" or "limiting the growth of a tumor" refers to decreasing the rate of growth of the cancer cells/tumor. This is measurable as an absence of any detectable change in size or weight of the cancer cells/tumor or a decrease in the rate of increase in the size of a group of cancer cells or a tumor.

As used herein, the term "tumor" is a group of cancer cells which grows at an anatomical site outside of the blood stream and requires the formation of requires the formation of small blood vessels and capillaries to supply nutrients to the growing tumor mass.

As used herein, the term "selecting syncytia" refers to the process of physically isolating or harvesting syncytia from a monolayer culture infected with an attenuated measles virus in order to further propagate the particular form of the virus contained within a particular syncytium.

As used herein, the term "expanding" refers to the process whereby a particular virus is propagated in host cells in order to increase the available number of copies of that particular virus, preferably by at least 2-fold, more preferably by 5-10-fold, or even by as much as 50-100-fold relative to unexpanded cells.

The terms "marker" or "biomarker" encompass, without limitation, miRNAs, lipids, lipoproteins, proteins, cytokines, chemokines, growth factors, polypeptides, nucleic acids, RNA, DNA, genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants. In one aspect, a marker is poliovirus receptor-related 4 (PVRL4). PVRL4 is also known as Nectin 4, PRR4, and LNIR. A RefSeq ID of PVRL4 is NM_030916. An accession number of PVRL4 is AF426163.

As used herein, the term "cancer specific marker" or "tumor specific marker" is an antigen which is preferentially or exclusively expressed on cancerous cells, and is not found, or is found in lower amounts in non-cancer cells.

The term "sample" can include an RNA, a single cell or multiple cells or fragments of cells or an aliquot of body fluid, taken from a subject, by means including venipuncture, excretion, swabbing, ejaculation, massage, biopsy, needle aspirate, lavage sample, scraping, surgical incision, or intervention or other means known in the art.

The term "expression data" refers to a value that represents a direct, indirect, or comparative measurement of the level of expression of a nucleotide (e.g., RNA or DNA) or polypeptide. For example, "expression data" can refer to a value that represents a direct, indirect, or comparative measurement of the RNA expression level of PVRL4.

The term "obtaining a dataset associated with a sample" or "obtaining a first dataset associated with a sample" encompasses obtaining a set of data determined from at least one sample. Obtaining a dataset encompasses obtaining a sample, and processing the sample to experimentally determine the data. The phrase also encompasses receiving a set of expression data directly or indirectly, e.g., from a third party that has processed the sample to experimentally determine the dataset. Additionally, the phrase encompasses mining data from at least one database or at least one publication or a combination of databases and publications. A dataset can be obtained by one of skill in the art via a variety of known ways including accessing a dataset stored on a storage memory.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (see the worldwide web at: ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Attenuated Measles

In one aspect, an attenuated strain of virus is grown in culture to provide an effective dose which will limit and/or cause regression of a group of cancer cells such as a tumor. Attenuated strains of viruses are obtained by serial passage of the virus in cell culture (e.g., in non-human cells), until a virus is identified which is immunogenic but not pathogenic. While wild type virus will cause fatal infection in marmosets, vaccine strains do not. In humans, infection with wild type viral strains is not generally fatal but is associated with classic measles disease. Classic measles disease includes a latent period of 10-14 days, followed by a syndrome of fever, coryza, cough, and conjunctivitis, followed by the appearance of a maculopapular rash and Koplik's spots (small, red, irregularly shaped spots with blue-white centers found inside the mouth). The onset of the rash coincides with the appearance of an immune response and the initiation of virus clearance. In contrast, individuals receiving an attenuated measles virus vaccine do not display classical measles symptoms. Attenuation is associated with decreased viral replication (as measured in vivo by inability to cause measles in monkeys), diminished viremia, and failure to induce cytopathological effects in tissues (e.g., cell-cell fusion, multinucleated cells). However, these biological changes have not been mapped to any single genetic change in the virus genome.

In an aspect, an attenuated strain of measles virus which has been clinically tested as a vaccine for measles infection is used to provide an effective dose which will limit and/or cause regression of a group of cancer cells, such as a tumor. The Moraten attenuated form of the virus has been used world-wide as a vaccine and has an excellent safety record (Hilleman, et al., J. Am. Med. Assoc. 206: 587-590, 1968). Accordingly, in one aspect, the Moraten strain is used to provide an effective dose. The Moraten vaccine is commercially available from Merck and is provided lyophilized in a vial which when reconstituted to 0.5 ml comprises $10^3$ pfu/ml. A vaccine against the Moraten Berna strain is available from the Swiss Serum Vaccine Institute Berne.

In a further aspect, the Edmonston-B vaccine strain of measles virus is used (MV-Edm) (Enders and Peebles, Proc. Soc. Exp. Biol. Med. 86: 277-286, 1954). MV-Edm grows efficiently in tumor cells but its growth is severely restricted in primary cultures of human peripheral blood mononuclear cells, normal dermal fibroblasts, and vascular smooth muscle cells. A form of the Enders attenuated Edmonston strain is available commercially from Merck (Attenuvax™). Other attenuated measles virus strains are also encompassed, such as Leningrad-16, and Moscow-5 strains (Sinitsyna, et al., Res. Virol. 141(5): 517-31, 1990), Schwarz strain (Fourrier, et al., Pediatrie 24(1): 97-8, 1969), 9301B strain (Takeda, et al. J. VIROL. 72/11: 8690-8696), the AIK-C strain (Takehara, et al., Virus Res 26 (2): 167-75, 1992 November), and those described in Schneider-Shaulies, et al., PNAS 92(2): 3943-7, 1995, the entireties of which are incorporated by reference herein. Other measles viruses are generally known in the art and described in more detail below in the Examples section.

In a further aspect, the measles virus is provided in a composition comprising a mixture of attenuated oncolytic viruses. In one aspect, the mumps measles and rubella vaccine (MMR) is used. The MMR vaccine was introduced into the United States in 1972 and into the United Kingdom in 1998. Commercially available preparations of the MMR vaccine is obtainable from Merck, Pasterur Merieux Connaught, or SmithKline Beecham, and also contain the Moraten strain of attenuated measles virus at a minimum titer of $10^3$ PFU/ml. In still a further aspect, the measles virus is provided in a composition comprising Edmonston Zagreb measles strain (an attenuated strain obtained from the Edmonston-enders stain) and the Wistar RA 27/3 strain of rubella (Swiss Serum Vaccine Institute Berne). It should be apparent to those of skill in the art that any clinically tested measles vaccine is acceptable for use.

In one aspect, an effective dose of an attenuated measles virus is produced by infecting a primary cell or a continuous cell line with a starting innoculum of an stock comprising an attenuated Moraten strain of measles virus (or an innoculum of an MMR stock) or the MV-Edm strain or any of the other strains described above and expanding the virus after serial passage. Cells or cell lines include, but are not limited to, monkey kidney or testes cells or monkey cell lines (e.g., Vero, KB, CV-1, BSC-1, and the like). Viral replication in cells is observed as cell-cell fusion and syncytia formation.

The attenuated measles virus can be expanded until a desired dose concentration is obtained in standard cell culture media (e.g., DMEM or RPMI-1640 supplemented with 5-10% fetal bovine serum at 37 C in 5% $CO_2$). In one aspect, the therapeutically effective dose concentration is about $10^3$ to $10^{12}$ pfu. In another aspect, the concentration is about $10^5$ to $10^8$ pfu. Viral titer is assayed by inoculating cells (e.g., Vero cells) in culture dishes (e.g., such as 35 mm dishes). After 2-3 hours of viral adsorption, the inoculum is removed and cells are overlaid with a mixture of cell culture medium and agarose or methylcellulose (e.g., 2 ml DMEM containing 5% FCS and 1% SeaPlaque agarose). After about 3 to about 5 days, cultures are fixed with 1 ml of 10% trifluoroacetic acid for about 1 hour, then UV cross-linked for 30 minutes. After removal of the agarose overlay, cell monolayers are stained with crystal violet and plaques are counted to determine viral titer. Virus is harvested from cell syncytia by scraping cells from the dishes, subjecting them to freeze/thawing (e.g., approximately two rounds), and centrifuging. The cleared supernatants represent "plaque purified" virus.

Viral stocks can be produced by infection of cell monolayers (e.g., adsorption for about 1.5 hours at 37 C), followed by scraping of infected cells into a suitable medium (e.g., Opti-MEM, Gibco-BRL) and freeze/thaw lysis (e.g., 2 rounds). Viral stocks are aliquoted, frozen and stored at −70 C to −80 C and can be stored at concentrations higher than the therapeutically effective dose. In one aspect, the viral stock is stored in a stabilizing solution. Stabilizing solutions are known in the art and include, for example, sugars (e.g., trehalose, dextrose, glucose), amino acids, glycerol, gelatin, monosodium glutamate, $Ca^{2+}$ and $Mg^{2+}$. Suitable stabilizing solutions are described in U.S. Pat. Nos. 4,985,244, and 4,500,512, the entireties of which are incorporated by reference herein.

In another aspect, an attenuated measles virus strain is generated from a primary measles strain. In this aspect, a primary measles virus is isolated by inoculating a cell line with peripheral blood leukocytes or respiratory secretions from a patient. Suitable cells and cell lines include, but are not limited to, primary human cells (e.g., blood, lung, conjunctiva, kidney, intestine, amnion, skin, muscle, thymic stroma, foreskin, and uterus), human cell lines (e.g., Wi-38, MRC-5, Hep-2, HeLa, A549), primary monkey cells (e.g., kidneys, and testes), and monkey cell lines (e.g., Vero, KB, CV-1, and BSC-1), and the Epstein-Barr virus-transformed marmoset B lymphocyte cell line (B95-8).

Cells can be passaged until propagation of wild-type virus and production of cytopathic effects can be detected in tissue culture, such as cell-cell fusion and syncytia formation. In one aspect, viral stocks are prepared using a low multiplicity of infection to avoid the accumulation of defective particles. Plaques become visible after about 3 to 5 days of culture, and the virus is allowed to continue to replicate until a desired concentration is reached. Viral titers are determined as described above.

Once a primary measles virus is isolated in culture, it can be serially passaged in a non-human cell line. The Edmonston strain was produced by Enders as a result of successive series of passages through human kidney tissue culture, human amnion tissue culture, embryonated eggs and chick embryo tissue culture. Clones of measles virus obtained in the last culture passage and suspensions of viruses are obtained and purified by centrifugation or filtration to completely remove any culture cells. Attenuated virus suspensions with desired properties are selected (e.g., high infectivity, high immunogenicity, and low pathogenicity).

The infectivity of an attenuated virus suspension is determined by determining a dilution of virus that produces cytopathic effects (cell-cell fusion and syncytia formation observed microscopically) in at least 50% of cultured cells (e.g., 5 out of 10 test tubes comprising 5 ml cultures of Vero cell sheets). In one aspect, an attenuated virus suspension is selected which causes cytopathic effects in 50% of infected Vero cells at least a $10^3$-fold dilution (i.e., having a $TCID_{50}$ of 3) (see "Review of Medical Microbiology", 13th ed., pp. 344-345, Lange Medical Publications, 1976).

The immunogenicity of an attenuated virus suspension is determined by evaluating seroconversion in monkeys after injection with the virus. Seroconversion is measured by determining the levels of antibody before and after immunization (% of increase in the amount of a specific antibody). In one aspect, an attenuated vaccine produces about 70% to 100% seroconversion approximately 2 months after injection.

Low pathogenicity and decreased replication efficiency is determined by evaluating the appearance of classic measles symptoms in monkeys (see, e.g., Kobune, et al., Lab Anim. Sci. 46 (3): 315-20, 1996). In one aspect, an attenuated measles virus suspension is selected which does not produce classical measles in monkeys (e.g., within a month). Although measles can be viewed as a continuum of symptoms (fever, coryza, cough, and conjunctivitis, followed by the appearance of a rash and Koplik's spots), symptoms that are generally the same as the adverse effects observed with the Attenuvax™ vaccine are not considered "measles," in this aspect of the experiment. Thus symptoms such as moderate to high fever lasting 1-2 days, a rash lasting 1-2 days, cough and rhinitis, and/or erythma multiforme (skin rash) would not cause a monkey to be identified as having measles. In one aspect, the classification of a monkey as having measles is dependent on the appearance of Koplik's spots.

In additional aspects, properties such as thermosensitivity can be selected (see, e.g., U.S. Pat. Nos. 4,211,843, 4,071,618 and 3,133,861, the entirety of which is incorporated by reference herein). Non-human cell lines include, but are not limited to chick embryos, quail embryos, duck embryos, and dog and bovine kidney cells.

In still a further aspect, recombinant measles viruses comprising genetic modifications are derived from wild type measles virus to generate attenuated viruses, e.g., viruses having high immunogenicity (as measured by 70-100% seroconversion) and no pathogenicity (e.g., not producing classical measles symptoms, as discussed above). In one aspect, genetic modifications are introduced through random mutagenesis of a plasmid comprising the sequence of a wild type measles virus. Sequences of wild type isolates are disclosed in U.S. Pat. No. 5,578,448, the entirety of which is enclosed herein by reference.

In another aspect, particular cistrons in the measles virus genome are targeted to modify genes whose expression is associated with attenuation (Schneider-Shaulies, et al. PNAS 92(2): 3943-7, 1995; Takeda, et al. J. Virol. 1998 72/11 (8690-8696)). Thus, in one aspect, a recombinant measles virus strain is generated comprising a single point mutation or multiple non-contiguous point mutations in any of an H protein, a V protein, a C protein, and combinations thereof. In still a further aspect, natural variants of the wild type or attenuated measles viruses are identified (e.g., such as from cultures of virus from infected patients) which have at least one point mutation in their genome. In some aspects, a measles virus can be a recombinant measles virus that maintains PVRL4 (Nectin 4) binding ability but is engineered to be blind for CD150/SLAM and CD46/MCP. See Leonard et al. (2008) J. Clin. Invest. 118: 2448-58 and Hashiguch et al. (2011) Nat. Struc. Mol. Biol. 18: 135-41.

Methods of Treating PVRL4-Associated Disease Using Measles Virus

Dosage, Administration and Pharmaceutical Formulation

Measles virus, when used to immunize against measles, is typically injected in a single $10^3$ dose subcutaneously or intramuscularly. The MMR vaccine is typically administered twice at the same dose, and is also administered subcutaneously or intramuscularly.

In some aspects, measles virus can be used to treat a PVRL4-associated disease. PVRL4-associated disease can include various cancers, such as those described herein. In some aspects, tumors can be monitored for expression of PVRL4 to determine if MV treatment is feasible. For example, adenocarcinomas can be monitored for expression of PVRL4 to determine if MV treatment is feasible.

In one aspect, measles virus is injected either directly into a group of cancer cells (e.g., a tumor) or is delivered intravenously to cancer cells. Types of cancer cells susceptible to treatment with measles or MMR include neuronal cells, glial cells, myelomonocytic cells, adenocarcinomas, and the like. Types of cancer treatable by the methods disclosed herein, include, but are not limited to, myeloma, melanoma, glioma, and breast carcinoma. In one aspect of the invention, the measles virus is used to limit or cause regression of lymphomas. In still a further aspect, the measles virus is used to limit or cause the regression of cancer cells in a patient with Non-Hodgkin's Lymphoma. In one aspect, direct delivery into one type of cancer cells (e.g., a lymphoma) is used to reduce or limit the growth of a different type of cancer (e.g., a carcinoma). Other types of cancer treatable via the methods disclosed herein are described in more detail below.

In one aspect, the measles virus is administered to the patient in a biologically compatible solution or a pharmaceutically acceptable delivery vehicle, by administration either directly into a group of cancer cells (e.g., intratumorally) or systemically (e.g., intravenously). Suitable pharmaceutical formulations, in part, depend upon the use or the route of entry, for example transdermal, or by injection. Such forms should not prevent the composition or formulation from reaching a target cell (i.e., a cell to which the virus is desired to be delivered to) or exerting its effect. For example, pharmacological compositions injected into the blood stream should be soluble.

While dosages administered will vary from patient to patient (e.g., depending upon the size of a tumor), a "therapeutically effective dose" can be determined by setting as a lower limit, the concentration of virus proven to be safe as a vaccine (e.g., $10^3$ pfu) and escalating to higher doses of up to, e.g., $10^{12}$ pfu, while monitoring for a reduction in cancer cell growth along with the presence of any deleterious side effects. A therapeutically effective dose can be that dose which provides at least a 10% reduction in the number of cancer cells or in tumor size and can be detected in the circulation by detection of an antigen and correlation of the antigen to the presence of the cancer cell. Escalating dose studies are routine in the art (see, e.g., Nies and Spielberg, "Principles of Therapeutics," In Goodman & Gilman's The Pharmacological Basis of Therapeutics, eds. Hardman, et al., McGraw-Hill, NY, 1996, pp 43-62).

In some aspects, a composition comprising an attenuated measles virus is delivered in a therapeutically effective dose in the range of from about $10^3$ pfu to about $10^{12}$ pfu. In one aspect, the dose range is $10^5$ to $10^7$ pfu. In one aspect, the dose range can be less than or equal to $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ pfu or more. In some aspects, the therapeutically effective dose is provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same, or further modified virus) can be administered by the same route as initially used or by another route. A therapeutically effective dose can be delivered in several discrete doses (e.g., days or weeks apart) and in one aspect, one to about twelve doses are provided. Alternatively, a therapeutically effective dose of measles virus is delivered by a sustained release formulation.

Devices for providing sustained release formulations are known in the art, and generally include a polymeric excipient (e.g., a swellable or non-swellable gel, or collagen) which is implanted at a site of drug delivery, and from which drug is gradually dispensed over time as a continuous or pulsed dose (see, e.g., U.S. Pat. Nos. 5,980,508, 5,001,692, and 5,137,727, the entireties of which are incorporated by reference herein). In one aspect, a therapeutically effective dose of measles virus is provided within a polymeric excipient and the excipient/virus composition is implanted at a site of cancer cells (e.g., in proximity to, or within a tumor). In this aspect, the action of body fluids gradually dissolves the excipient and continuously releases the effective dose of measles virus over a period of time. In another aspect, a sustained release device which comprises a series of alternating active and spacer layers is implanted at a site of cancer cells. In this aspect, each active layer of the device comprises a dose of virus embedded in excipient, while each spacer layer comprises only excipient or low concentrations of virus (i.e., lower than the effective dose). As each successive layer of the device dissolves, pulsed doses of measles virus are delivered. The size/formulation of the spacer layers determines the time interval between doses and is optimized according to the therapeutic regimen being used.

Direct administration can be performed according to any of a number of methods routinely practiced in the art. In one aspect, a tumor which is palpable through the skin (e.g., such as a lymphoma) is injected directly with measles virus through the skin (e.g., using ultrasound guidance). In another aspect, direct administration occurs via a catheter line or other medical access device and is used in conjunction with an imaging system (see, e.g., U.S. Pat. Nos. 6,095,976; 6,026,316; and 5,713,858) to localize a group of cancer cells. In this aspect, an implantable dosing device is placed in proximity to the group of cancer cells using a guidewire inserted into the medical access device. In still another aspect, an effective dose is directly administered to a group of cancer cells visible in an exposed surgical field.

In another aspect, the measles virus is delivered systemically. In one aspect, the attenuated measles virus is delivered intravenously via injection or via an intravenous delivery device designed for administration of multiple doses of a medicament. Such devices include, but are not limited to, winged infusion needles, peripheral intravenous catheters, midline catheters, peripherally inserted central catheters (PICC), and surgically placed catheters or ports (see, e.g., U.S. Pat. No. 6,012,034). Peripheral intravenous catheters and winged infusion needles are inserted into a small peripheral vein in the lower arms and hands. With peripheral intravenous catheters, the entry site must be changed every few days or as required. Peripheral intravenous catheters are often used for short-term therapy and can also be used until a long-term access device can be inserted.

The course of therapy can be monitored by evaluating changes in clinical symptoms (known in the art for each particular type of cancer) or by direct monitoring of the size of a group of cancer cells or tumor. Viral therapy using measles viruses is effective if tumor size and/or clinical symptoms are reduced following administration of virus. In one aspect, the method effects at least a 10% reduction in the size of a group of cancer cells within a given time period, such as one to four weeks. In further aspects, the method effects reductions of 25%, 50% 75% and up to about 100%.

Reduction in size in a group of cancer cells or tumor cells is measured, as discussed above, either directly, using calipers, or by using imaging techniques (e.g., X-ray, magnetic resonance imaging, or computerized tomography) or from the assessment of non-imaging optical data (e.g., spectral data). Reduction in the levels of a cancer specific antigen in a patient can alternatively, or additionally, be monitored. Cancer specific antigens include, but are not limited to carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4. In this aspect, an effective dose of attenuated measles virus is that which produces a reduction in levels of cancer specific antigens of at least 10%.

In a further aspect, cytotoxic lymphocyte (CTL) responses to the tumor are measured to identify an increased tumor specific immune response after treatment. In this aspect, a patient's T-cells are isolated and frozen both prior to administration of the measles virus and after treatment, when a group of cancer cells/tumor is biopsied. CTL responses are measured using methods routinely used in the art (e.g., U.S. Pat. No. 6,083,751 and Herin et al., Int. J. Cancer, 39:390-396 (1987)). In still a further aspect, a biopsy of a patient's cancer cells/tumor before and after injection is monitored to determine alterations in the histology of the cancer cells/tumor such as cell-cell fusion and lysis. In this aspect, an effective dose is one which causes at least one cell to have >20 nuclei. Any, or all, of these assays may be used to monitor the effectiveness of measles vaccine.

In some aspects, the vaccines are administered to patients who are not immunocompromised as determined by assessing immunoglobulin levels, absolute lymphocyte count, CD4:CD8 ratio and DTH and who also have a pre-existing measles virus immunity. Throughout the treatment, patients are monitored for the existence of any classical measles symptoms, and dosages are titrated accordingly, to minimize the presence of such symptoms.

Genetic Engineering of Measles Virus

Therapeutic effects of measles virus can be increased via genetic engineering through insertion of therapeutic nucleotides such as genes, siRNA, and/or miRNA. In one aspect, a strain of measles virus is genetically modified to provide an oncolytic virus. In an aspect, a recombinant attenuated virus is modified by the insertion of a gene, siRNA, or miRNA.

In one aspect, a nucleotide of interest (e.g., a gene, siRNA, or miRNA) is inserted into a plasmid comprising the sequence of a measles virus genome but lacking cistrons encoding the membrane glycoproteins or the viral polymerase using standard cloning techniques well known in the art. Recombinant measles viruses can be isolated (i.e., rescued) by co-transfecting a helper cell line with the mutagenized plasmid and a plasmid expressing the measles virus L polymerase. The L protein is expressed transiently, rather than stably, since high levels of L expression can impair the rescue of virus, while transient expression allows titration of the L protein as needed (Radecke, et al., 1995, the entirety of which is incorporated herein by reference). The helper cell line comprises cells (e.g., human embryonic kidney cells) stably expressing the wild type MV N and P measles proteins, i.e., providing the remaining functions of necessary for the virus to infect and replicate. The construction of an exemplary helper cell line (e.g., 293-3-6 cells) is described in Radecke, et al., 1995, supra.

After a suitable period of time following transfection (e.g., two days), cells are expanded into larger culture dishes (e.g., 90 mm dishes) and cultured (e.g., for another two days) before scraping and adsorption to cell monolayers. Infected Vero cells are monitored for syncytia formation, and syncytia are picked and propagated further, until a desired concentration is obtained (e.g., $10^3$-$10^8$ pfu). Viral stocks are produced as described above.

Methods of Identifying Subjects in Need of Measles Virus Administration

In some aspects, a method is described for identifying a subject in need of measles virus administration. In one aspect, the method includes obtaining a first dataset associated with a sample obtained from the subject, wherein the first dataset comprises quantitative expression data for PVRL4. In another aspect, the method includes analyzing the first dataset to determine the expression level of PVRL4, wherein the expression level of PVRL4 positively correlates with an increased likelihood that the subject will benefit from measles virus treatment. In some aspects the analysis further comprises comparing the first dataset to a second dataset associated with a control sample, wherein the second dataset comprises quantitative expression data for a control marker, and wherein a statistically significant difference between expression of PVRL4 and expression of the control marker indicates an increased likelihood that the subject will benefit from measles virus treatment. In some aspects, the control sample is associated with a control subject or with a control population. In some aspects, expression of PVRL4 is significantly increased compared to expression of the control marker.

The quantity of PVRL4 can be indicated as a value. A value can be one or more numerical values resulting from evaluation of a sample under a condition. The values can be obtained, for example, by experimentally obtaining measures from a sample by an assay performed in a laboratory, or alternatively, obtaining a dataset from a service provider such as a laboratory, or from a database or a server on which the dataset has been stored, e.g., on a storage memory.

In an aspect, the quantity of PVRL4 can be one or more numerical values associated with RNA expression levels and/or protein expression levels, e.g., resulting from evaluation of a sample under a condition.

In an aspect, PVRL4's associated value can be included in a dataset associated with a sample obtained from a subject. A dataset can include the marker expression value of two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s).

In another aspect, the invention includes obtaining a sample associated with a subject, where the sample includes one or more markers such as PVRL4. The sample can be obtained by the subject or by a third party, e.g., a medical professional. Examples of medical professionals include physicians, emergency medical technicians, nurses, first responders, psychologists, medical physics personnel, nurse practitioners, surgeons, dentists, and any other obvious medical professional as would be known to one skilled in the art. A sample can include RNA or protein. A sample can also include one or more cells. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe. The bodily fluid can then be tested to determine the value of one or more markers using an assay, such as an assay described in the Examples section below. The value of the one or more markers can then be evaluated by the same party that performed the assay using the methods disclosed herein or sent to a third party for evaluation using the methods disclosed herein.

Assays

Examples of assays for one or more markers such as PVRL4 include sequencing assays, microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, immunoprecipitation, and the assays described in the Examples section below. The information from the assay can be quantitative and sent to a computer system. The information can also be qualitative, such as observing patterns or fluorescence, which can be translated into a quantitative measure by a user or automatically by a reader or computer system. In an aspect, the subject can also provide information other than assay information to a computer system, such as race, height, weight, age, gender, eye color, hair color, family medical history and any other information that may be useful to a user, such as a clinical factor described herein.

Informative PVRL4 Markers

In addition to the specific, exemplary markers identified in this application by name, accession number, or sequence, included within the scope of the invention are all variant sequences having at least 50, 60, 70, 80, 81, 82, 83, 84, 85, 86, 87, 88, 89, 90, 91, 92, 93, 94, 95, 96, 97, 98, or 99% or greater identity to the exemplified marker sequences. The percentage of sequence identity may be determined using algorithms well known to those of ordinary skill in the art, including, e.g., BLASTn, and BLASTp, as described in Stephen F. Altschul et al., J. Mol. Biol. 215:403-410 (1990) and available at the National Center for Biotechnology Information website maintained by the National Institutes of Health.

Computer Implementation

In one aspect, a computer comprises at least one processor coupled to a chipset. Also coupled to the chipset are a memory, a storage device, a keyboard, a graphics adapter, a pointing device, and a network adapter. A display is coupled to the graphics adapter. In one aspect, the functionality of the chipset is provided by a memory controller hub and an I/O controller hub. In another aspect, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one aspect, program modules are stored on the storage device, loaded into the memory, and executed by the processor.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

Aspects of the entities described herein can include other and/or different modules than the ones described here. In addition, the functionality attributed to the modules can be performed by other or different modules in other aspects. Moreover, this description occasionally omits the term "module" for purposes of clarity and convenience.

Antibodies which Bind to PVRL4

Also disclosed herein are antibodies that bind PVRL4 that block viral infection of a cell, such as measles virus infection. Such antibodies can represent research and diagnostic tools in the study of virus infection and the development of more effective anti-measles therapeutics. In addition, pharmaceutical compositions comprising antibodies against PVRL4 can represent effective anti-virus therapeutics.

In some aspects, an antibody suitable for blocking viral infection is specific for at least one portion of an extracellular region of the PVRL4 polypeptide. For example, one of skill in the art can use the extracellular amino acids of PVRL4 to generate appropriate antibodies for interfering with measles infection of a cell. Alternatively, one of skill in the art can use whole cells expressing PVRL4 as an immunogen for generation of anti-PVRL4 antibodies which either block virus infection or interfere with the entry of the virus into a cell. Anti-PVRL4 antibodies can have any or all of these functions. Antibodies can include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in IMMUNOCHEMICAL PROTOCOLS (Manson, ed.), pages 1-5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, Nature 256: 495 (1975); Coligan et al., sections 2.5.1-2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., Purification of Immunoglobulin G (IgG), in METHODS IN MOLECULAR BIOLOGY, VOL. 10, pages 79-104 (Humana Press 1992).

Methods of in vitro and in vivo multiplication of monoclonal antibodies is well-known to those skilled in the art. Multiplication in vitro may be carried out in suitable culture media, such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethyl-pentadecane) prior to injection. After one to three weeks, the desired monoclonal antibody is recovered from the body fluid of the animal.

Therapeutic applications for antibodies disclosed herein are contemplated. For example, antibodies can also be derived from subhuman primate antibody. General techniques for raising therapeutically useful antibodies in baboons can be found, for example, in Goldenberg et al., International Patent Publication WO 91/11465 (1991) and Losman et al., Int. J. Cancer 46:310 (1990), which are hereby incorporated by reference.

Alternatively, a therapeutically useful anti-PVRL4 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, by Jones et al., Nature 321: 522 (1986); Riechmann et al, Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993), which are hereby incorporated by reference.

Antibodies also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies may be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994); Lonberg et al., Nature 368:856 (1994); and Taylor et al., Int. Immunol. 6:579 (1994), which are hereby incorporated by reference.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., Arch. Biochem. Biophys. 89:230 (1960); Porter, Biochem. J. 73:119 (1959); Edelman et al., METHODS IN ENZYMOLOGY, VOL. 1, page 422 (Academic Press 1967); and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of VH and VL chains. This association may be noncovalent, as described in Inbar et al., Proc. Nat'l Acad Sci. USA 69:2659 (1972). Alternatively, the variable chains can be linked by an intermolecular disulfide bond or cross-linked by chemicals such as glutaraldehyde. See, e.g., Sandhu, supra.

In some aspects, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., Science 242:423426 (1988); Ladner et al., U.S. Pat. No. 4,946,778; Pack et al., Bio/Technology 11: 1271-77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

Variants of PVRL4

The term "PVRL4 variant" as used herein means a molecule that simulates at least part of the structure of PVRL4 and interferes with the infection of cells by virus.

In some aspects, peptides and peptide derivatives that have fewer amino acid residues than PVRL4 and block viral infection of a target cell, such as measles virus infection. Such peptides and peptide derivatives can represent research and diagnostic tools in the study of viral infection and the development of more effective anti-virus therapeutics. In some aspects, peptide fragments of PVRL4 include those which correspond to the regions of PVRL4 that are exposed on the cell surface.

In some aspects, peptides and peptide derivatives of naturally-occurring PVRL4 include PVRL4 mutants and chemically synthesized derivatives of PVRL4 that block viral infection of a target cell. For example, changes in the amino acid sequence of PVRL4 are contemplated. PVRL4 can be altered by changing the DNA encoding the protein. In some aspects, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine;

serine to threonine; threonine to serine; tryptophan to tyrosine; tyrosine to tryptophan or phenylalanine; valine to isoleucine or leucine.

Variants comprise analogs, homologs, muteins and mimetics of PVRL4 that retain the ability to block viral infection. Peptides of the PVRL4 refer to portions of the amino acid sequence of PVRL4 that also retain this ability. The variants can be generated directly from PVRL4 itself by chemical modification, by proteolytic enzyme digestion, or by combinations thereof. Additionally, genetic engineering techniques, as well as methods of synthesizing polypeptides directly from amino acid residues, can be employed.

Peptides can be synthesized by such commonly used methods as t-BOC or FMOC protection of alpha-amino groups. Both methods involve stepwise syntheses whereby a single amino acid is added at each step starting from the C terminus of the peptide (See, Coligan, et al., Current Protocols in Immunology, Wiley Interscience, 1991, Unit 9). Peptides can also be synthesized by the well known solid phase peptide synthesis methods described Merrifield, J. Am. Chem. Soc., 85:2149, 1962), and Stewart and Young, Solid Phase Peptides Synthesis, (Freeman, San Francisco, 1969, pp. 27-62), using a copoly(styrene-divinylb enzene) containing 0.1-1.0 mMol amines/g polymer. On completion of chemical synthesis, the peptides can be deprotected and cleaved from the polymer by treatment with liquid HF-10% anisole for about ¼-1 hours at 0.degree. C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Alternatively, peptides can be produced by recombinant methods as described below.

The term "substantially purified" as used herein refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify PVRL4 peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Non-peptide compounds that mimic the binding and function of PVRL4 ("mimetics") can be produced by the approach outlined in Saragovi et al., Science 253: 792-95 (1991). Mimetics are molecules which mimic elements of protein secondary structure. See, for example, Johnson et al., "Peptide Turn Mimetics," in BIOTECHNOLOGY AND PHARMACY, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions.

Longer peptides can be produced by the "native chemical" ligation technique which links together peptides (Dawson, et al., Science, 266:776, 1994). Variants can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990-93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

PVRL4-Binding Agents

In yet another aspect, the invention relates to PVRL4-binding agents that, e.g., block viral infection of a cell, such as measles virus infection. As used herein the term "PVRL4-binding agent" refers to an agent that physically binds to a region of PVRL4 protein, PVRL4 mRNA, or PVRL4 gene. Such agents can represent research and diagnostic tools in the study of viral infection and the development of more effective anti-virus therapeutics. In addition, pharmaceutical compositions comprising PVRL4-binding agents can represent effective anti-virus therapeutics. Examples of PVRL4-binding agents are a small interfering RNA (siRNA) and an antibody. Thus, PVRL4-binding agents can include agents that bind to PVRL4 protein and agents that bind to PVRL4 nucleotides such as mRNA. Examples of PVRL4-specific siRNA and antibodies are described in the Examples section below. Other PVRL4-binding agents can include antisense oligonucleotides, small molecules, peptides, and ribozymes. Other examples of PVRL4-binding agents are described herein.

Screen for PVRL4 Binding Agents and Compositions

In another aspect, also provided is a method for identifying a composition which binds to PVRL4 and/or blocks viral infection of a cell. The method includes incubating components comprising the composition and PVRL4 under conditions sufficient to allow the components to interact and measuring the binding of the composition to PVRL4. Compositions that bind to PVRL4 include peptides, peptidomimetics, polypeptides, chemical compounds and biologic agents as described above.

Incubating includes conditions which allow contact between the test composition and PVRL4. Contacting includes in solution and in solid phase. The test ligand(s)/composition may optionally be a combinatorial library for screening a plurality of compositions. Compositions identified in the method can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229-237, 1988).

To determine if a composition can functionally complex with the receptor protein, induction of the exogenous gene is monitored by monitoring changes in the protein levels of the protein encoded for by the exogenous gene, for example. When a composition(s) is found that can induce transcription of the exogenous gene, it is concluded that this composition(s) can bind to the receptor protein coded for by the nucleic acid encoding the initial sample test composition(s).

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method are combinatorial chemistry methods for identifying compounds (e.g., chemical compounds) that bind to PVRL4. Ligands/compositions that bind to PVRL4 can be assayed in standard cell assays to determine whether the composition inhibits, interferes with, or blocks viral infection of a cell. Screening methods also include inhibition of ligand binding to PVRL4 (e.g., via use of radiolabeled ligand). Thus, the screening method is also useful for identifying variants, binding or blocking agents, etc., which functionally, if not physically (e.g., sterically) act as antagonists or agonists, as desired.

Pharmaceutical Compositions

Methods for treatment of PVRL4-associated diseases, such as cancer, are also encompassed by the invention. Said methods of the invention include administering a therapeutically effective amount of measles virus. The measles virus can be formulated in pharmaceutical compositions. These compositions can comprise, in addition to one or more of the measles viruses, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

The invention also includes various pharmaceutical compositions that block viral infection of a cell. The pharmaceutical compositions are prepared by bringing an antibody against PVRL4, a peptide or peptide derivative of PVRL4, a PVRL4 mimetic, or a PVRL4-binding agent into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV, 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, nucleic acid, virus, vector, small molecule or other pharmaceutically useful compound that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Diagnostic Applications and Kits

In some embodiments, a PVRL4-binding agent can be used as a diagnostic tool. The PVRL4-binding agent can be used to assay the amount of PVRL4 present in a sample and/or subject. The PVRL4-binding agent can be used to detect the presence or absence of PVRL4 in a sample and/or subject.

In some embodiments, a PVRL4-binding agent disclosed herein can be used or provided in an assay kit and/or method for the detection of PVRL4 in mammalian tissues or cells in order to screen/diagnose for a disease or disorder associated with PVRL4 such as cancer. The kit can comprise a PVRL4-binding agent and means for indicating the binding of the agent with PVRL4, if present, and optionally PVRL4 levels. Various means for indicating the presence of an agent can be used. For example, fluorophores, other molecular probes, labels, or enzymes can be linked to the agent and the presence of the agent can be observed in a variety of ways. The method for screening for such disorders can involve the use of the kit, or simply the use of one of the disclosed agents and the determination of whether the agent binds to PVRL4 in a sample. As will be appreciated by one of skill in the art, high or elevated levels of PVRL4 will generally result in larger amounts of the agent binding to PVRL4 in the sample. Thus, degree of binding can be used to determine how much PVRL4 is in a sample. Subjects or samples with an amount of PVRL4 that is greater than a predetermined amount (e.g., an amount or range that a person without a PVRL4 related disorder would have) can be characterized as having a PVRL4 associated disorder.

In some aspects, a kit for detecting a PVRL4 expressing cell can include a PVRL4-binding agent in an amount effective to detect PVRL4 expression. In some aspects, a kit can include an agent suitable for detecting the binding between the PVRL4-binding agent and PVRL4. In some aspects, a kit can include instructions for using the PVRL4-binding agent to determine the likelihood that a cell can be infected by a measles virus. In some aspects, a kit can include instructions for using the PVRL4-binding agent to determine the likelihood that a subject will benefit from treatment with a measles virus. In some aspects, a kit can include a container containing the PVRL4-binding agent in a formulation and instructions for use. In some aspects, the formulation is present in a vial or an injectable syringe. In some aspects, the PVRL4-binding agent is bound to an array. In some aspects, the kit is used in an ELISA assay or a PCR assay. In some aspects, immunoassays and kits are described in U.S. Pat. Pub. 20120009196, herein incorporated by reference.

EXAMPLES

Below are examples of specific aspects for carrying out the invention. The examples are offered for illustrative purposes only, and are not intended to limit the scope of the invention in any way. Efforts have been made to ensure accuracy with respect to numbers used (e.g., amounts, temperatures, etc.), but some experimental error and deviation should, of course, be allowed for.

The practice of the invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Materials and Methods

Antibodies

M75 and B97 monoclonal antibodies, which neutralize CD46 binding to MV, were obtained from Seikugaku (Tokyo, Japan) and Dr. J. Schneider-Schaullies (Wurzburg, Germany), respectively. IPO-3 and A12 monoclonal antibodies, which inhibit CD150 binding to MV, were purchased from AbCam (Cambridge, Mass.). PE-conjugated mouse anti-human CD150/SLAM (clone A12) and PE-conjugated mouse IgG1 kappa isotype control (clone MOPC-21) were from BD Biosciences. Unconjugated mouse anti-human nectin-4 (MAB2659), PE-conjugated mouse anti-human nectin-4 monoclonal (FAB2659P), PE-conjugated mouse IgG2B isotype control (IC0041P), goat polyclonal anti-human PVRL4 (AF2659), and control goat (AB-108-C) antibodies came from R&D Systems (Minneapolis, Minn.). Monoclonal mouse anti-V5 (Sigma, clone V5-10) was used to detect V5 tagged proteins synthesized from the pcDNA3.2 DEST/V5 expression vector. The anti-Flag antibody (Sigma) was used to detect DYKDDDDK tagged proteins expressed from the pCMV6 entry vector.

Cell Culture and Virus Infections

Human primary small airway epithelial cells (SAEC) were obtained from Lonza Walkersville Inc., (Walkersville, Md.). Marmoset SAEC were prepared by the custom service division of Lonza Walkersville Inc. Vero, B95a, OMK, HeLa, LoVo, Huh7, HepG2, Hep3B, and CHOpgsA745 cells, were purchased from the American Type Culture Collection (Manassas, Va.). NCI-H125, NCI-H157, NCI-H460, SBC-3, NCI-H661, NCI-H520, RVH6847, NCI-226, MGH-7, MGH-24, and NCI-H358 cells came from Dr. Ming-Sound Tsao (Ontario Cancer Institute, Toronto, Canada). MDA-MB-468, MDA-MB-231, MCF7, T47D, HT-29, T84, HCT116, HS766T, DLD-1, and MDCK cells were acquired from Drs. David Hoskin and Craig McCormick (Dalhousie University, Halifax, Canada). The Edmonston vaccine/laboratory strain of MV was originally obtained from Dr. Erling Norrby (Karolinska Institute, Stockholm, Sweden). The recombinant Ichinoise-B 323 (IC323) wild type isolate expressing EGFP reporter gene (IC323-EGFP wtMV) and a recombinant Edmonston MV containing a WTF H protein (in place of the H protein of the vaccine strain), Edmonston-EGFP MV, SLAM blind-EGFP and CD46 blind-EGFP recombinant viruses were obtained from Dr. Roberto Cattaneo [33,52]. The Montefiore 89 strain of M (wildtype) was obtained from Ilya Spigland and Amy Fox (Montefiore Medical Center, Bronx, N.Y.).

CD46 Diagnostic RT-PCR and Agarose Gel Electrophoresis

Total RNA was extracted from HeLa, marmoset kidney NZP60, and marmoset SAEC using TRIzol® (Invitrogen). First strand cDNA was prepared with a SuperScript III® kit (Invitrogen). PCR was performed with conserved diagnostic CD46 primers spanning the SCR1 coding region of cDNA from the different cell types [5' oligo: gccgccgcgagtgtcccttccttc; 3' oligo: cactttggaactgggggatcccaag]. PCR amplification was done using PFUultra® II fusion HS polymerase (Stratagene). A 50 µl reaction volume was initially heated for 2 min at 95°, processed through 30 cycles of sequential temperatures of 95° (30 sec), 58° (30 sec), 72° (30 sec) and finally incubated for 10 min at 72°, using an Applied Biosystems Geneamp 9600 PCR machine. Samples were stored at 4°, prior to electrophoresis at 120 V on 0.9% agarose gels containing ethidium bromide. The PCR product derived from full length human CD46 cDNA was 834 bp and that from marmoset CD46 cDNA was 645 bp, as predicted from the sequences in the NCBI genebank (NM_002389.4 and U87917).

Microarray Analysis

Primary SAEC (Lonza) were cultured in a 6-well culture plate in DMEM with and without 2% FCS for 22 hrs. Cell lines were grown in 75 cm² T-flasks containing DMEM and 10% FCS. Extraction of total RNA was performed using a Qiagen RNeasy Kit (Qiagen). Analysis for mRNA transcripts was performed using the Affymetrix Human Gene ST 1.0 Array at The Centre for Applied Genomics located at The Hospital for Sick Children in Toronto, Canada. cDNA's from SAEC, susceptible (MCF7, MDA-MB-468, T-47D, NCI-H125, NCI-H358, and MGH-24) and non-susceptible (A549, MDA-MB-231) cell lines were biotin labeled, hybridized to the microarray chip, washed, and stained with streptavidin-PE. Normalized probe set data was analyzed with the Affymetrix Expression Console 1.1 software. Microarray data was deposited in the NCBI GEO database (accession #GSE26636).

Total RNA was extracted from SAEC and adenocarcinoma cell lines using the Qiagen RNeasy kit. The quality and quantity of RNA was assessed by both A260/A280 values and using an Agilent RNA BioAnalyzer. Microarray analysis was performed at the Applied Genomics Centre associated with the Toronto Hospital for Sick Children by Xiolin Wang. The Applied Genomics Centre is an accredited Affymetrix Service Provider. cDNA (5.5 µg in 220 µl) was transcribed and biotin end-labeled using the Affymetrix IVT kit. The fragmented probe was hybridized to the Human Gene 1.0 ST Array cartridge and washed using the FS450_0007 protocol, and stained with streptavidin-PE. The GeneChip was scanned with an Affymetrix GeneChip Scanner 3000. Chip data was analyzed by GCOS 1.4 and archived on DVD discs as GCOS DTT Files which included raw intensity CEL files and normalized CHP files. Microarray data was evaluated for Quality Control by the Applied Genomics Centre and transmitted to our laboratory. Data was further analyzed with Affymetrix Expression Console 1.1 software using the hugene-1_0st v.1 na30.hg19 annotation file. Normalized probe set intensity values on a scale of 0 (no signal) to 14 (strongest signal) were converted to a text file and exported to Microsoft Excel 2003 for further analysis. Negative and positive control data was discarded and the Probe Set's were filtered using the Excel filter function for the GO cellular component term "membrane", and this data was retained. Gene up-regulation was calculated by applying the formula [(SAEC with FCS)−(SAEC without FCS)]/(SAEC without FCS) to the normalized microarray intensity values and expressing up-regulation as a percentage. Gene up-regulation in permissive vs. non-permissive cells lines was obtained by applying the formula [(permissive)−(non-permissive)]/(non-permissive) to the microarray intensity values and expressing up-regulation as a percentage. Average gene up-regulation was determined for breast cancer (MCF7, MDA-MB-468, and T47D), lung cancer (MGH-24, NCI-H125, and NCI-H358) and SAEC cell lines (Data not shown). Membrane protein genes which were up-regulated >20% were compared between permissive breast cell lines and permissive lung cell lines, and then with serum activated permissive SAEC using the Excel function [=(ISERROR(MATCH(A1,$C$1:$C$N,0)),"",A1)], where A contains the Gene Names in the cell type (eg. Breast) compared to the Gene Names (C) in another cell type (eg. Lung). N represents the number of entries in the list being compared. Up-regulated gene products that were common between the different permissive cell lines are tabulated in FIG. 2.

Plasmid Transfection of Candidate Epithelial Receptors

A human plasma membrane open reading frame gene collection (HS5016) was obtained from Open Biosystems (Huntsville, Ala.). The genes contained within pDONR223 entry vectors were introduced into the Gateway pcDNA3.2/V5-Dest mammalian expression plasmid through recombination using the LR Clonase II system (Invitrogen). These genes contained a V5 tag. Genes which were not contained in the Open Biosystems Membrane Protein collection were purchased from Origene Systems (Rockville, Md.) and contained a DDK (Flag) tag. Expression plasmids were introduced into non-susceptible cells using Lipofectamine 2000 (Invitrogen) according to the manufacturer. Empty vector (pcDNA3.2-V5/Dest or pCMV6 DEST) as well as EGFP and SLAM expressing plasmids were included as controls. At 36-48 hrs post transfection, cells were inoculated with IC323-EGFP wtMV in Opti-MEM media (Invitrogen) at an m.o.i. of 10 for 2 hrs at 37° C. The inoculums were replaced with Dulbecco's minimum essential media containing 2% fetal calf serum. After 48 hrs, infected cells were visualized by phase contrast and fluorescence microscopy.

To assess protein expression of the candidate receptors, cell monolayers were lysed in radioimmunoprecipitation (RIPA) buffer (50 mm Tris-HCl, pH 7.4, 1% NP-40, 0.25% sodium deoxycholate, 150 mM sodium chloride, 1 mM ethylenediaminetetraacetic acid, 1 mM sodium fluoride, 1 mM sodium orthovanadate, 1 mM phenylmethylsulfonyl fluoride, 2 mM dithiothreitol, 1× protease inhibitor cocktail [Roche]) for 15 min on ice. The lysate was centrifuged at 13,000×g for 15 min at 4° C., and protein quantification was performed with the Bradford assay kit (Thermo Scientific). SDS-PAGE and Western immunoblotting was carried out using antibodies against DDK and V5 to detect expression of the candidate membrane receptors.

Flow Cytometry

Cells were grown to confluence in 10 cm$^2$ dishes, washed twice in cold PBS, and harvested in non-enzymatic cell dissociation buffer (Sigma). 250,000 cells were blocked with 2.5 µg of normal human IgG (R&D Systems) for 10 minutes on ice followed by the addition of 10 µl of either PE-conjugated PVRL4 (R&D Systems FAB2659P) or PE-conjugated mouse IgG2B isotype control (R&D Systems IC0041P) antibodies for 45 min on ice. Cells were washed twice in PBS containing 1% BSA, 5 mM EDTA, and 0.1% sodium azide and then fixed in 1% paraformaldehyde. Samples were run on a Cyan ADP Flow Cytometer (Beckman Coulter) and data were processed using FCS Express (De Novo Software). Unconjugated SLAM and mouse anti-human PVRL4 antibodies were used in the receptor down regulation experiments. Secondary antibodies conjugated to Alexa Fluor 647 were used to detect surface expression of SLAM and PVRL4 using the FL8 channel on the Cyan ADP Flow Cytometer.

Infection of the Basolateral and Apical Epithelial Cell Surface with MV

MCF7, NCI-H358, and CHO-PVRL4 cells were seeded onto Transwell permeable filter supports (Corning Inc., 0.4 µm pore size, 24 mm diameter) at a density of 7.0×10$^5$ cells per well for 4 days (MCF7 & NCI-H358) or 2 days (CHO-PVRL4). Polarization of MCF7 cells was verified by measuring transepithelial electrical resistance (TEER) with a Millipore-ERS Voltohmmeter equipped with STX electrodes (Millipore, Billerica Mass.). An impedence of greater than 500 Ω-cm$^2$ indicated that a cell line was polarized. To infect the apical surface, 10 PFU/cell of IC323-EGFP wtMV was added to the upper chamber of the transwell filter and allowed to adsorb for 2 h. To infect the basolateral surface, filter inserts were inverted and the virus was adsorbed for 2 h. The virus innoculum was subsequently removed from the apical or basolateral surface and the membranes were treated with citrate buffer to inactivate any non-internalized virus. The transwell filters were then returned to their normal orientation. Infected cells were viewed by fluorescence and phase contrast microscopy using a Leica DMI4000B inverted microscope (Leica Microsystems).

Confocal Microscopy

Cells grown on poly-D-lysine (Sigma) coated coverslips were fixed in 4% paraformaldehyde (10 min) and permeabilzed with 0.1% Triton X-100 in PBS (10 min). PVRL4 was detected by incubating the cells with goat anti-human PVRL4 (R&D Systems AF2659) at 7.5 µg/ml in PBS containing 5% FCS for 45 min at room temperature. Cells were subsequently stained with fluorophore-conjugated secondary antibodies for 30 min at room temperature. Nuclear DNA was stained (20 min) with TO-PRO-3 stain (Invitrogen). Cells were mounted with fluorescent mounting medium and images were acquired with ZEN 2008 imaging software on a Zeiss LSM 510 upright laser scanning confocal microscope. Images were captured with a 100× Plan APOCHRMOAT (1.4 NA) objective lens and processed using ZEN 2009 light and Adobe Photoshop CS3 using only linear adjustments.

Surface Biotinylation

Levels of PVRL4 on the cell surface of MCF7 cells were determined by surface biotinylation. Cells were seeded onto transwell filters (0.4 μm pore size, 24 mm diameter) at a density of $5.0 \times 10^5$ cells per filter. Five days post seeding, cells were washed either the apical or basolateral side of the membrane was incubated for 1 hour with PBS containing 2 mM S-NHS-biotin (Thermo Scientific) at 4° C., while 0.1M glycine was added to the opposite side of the membrane. After washing with 0.1M glycine, filter membranes were cut and cells were lysed in RIPA buffer Cell lysates were clarified by centrifugation at 21 000×g and biotinyalted surface proteins were immunoprecipitated with agarose-conjugated NeutrAvidin (Thermo Scientific). Following SDS-PAGE and immunoblotting onto polyvinylidene fluoride (PVDF) (Millipore), proteins were detected with goat anti-human PVRL4 antibodies (R&D Systems). Secondary antibodies were conjugated to horseradish peroxidase and visualized by chemiluminescence. Thirty micrograms of total whole cell lysate was run and blotted with anti-human PVRL4 antibodies and anti-GAPDH antibodies to control for protein loading.

siRNA Inhibition siRNA duplexes against human PVRL4 were purchased from Dharmacon using a predesigned ON-TARGET plus SMARTpool siRNA (L-004301-00-0005). Non-targeting siRNA was used as a negative control (D-001810-10-05). MCF7 and NCI-H358 cells were plated at 30-40% confluence in 35-mm dishes a day before siRNA transfection. One hundred picomoles of siRNA were mixed with 5 μl of Lipofectamine 2000 (Invitrogen) in 500 μl Opti-MEM (Invitrogen) and added to cells in 500 μl Opti-MEM. Cells were transfected at 0 hrs and 10 hrs and incubated an additional 16 hrs. At 26 hrs, Opti-MEM was replaced with DMEM containing 5% FCS and cells were allowed to grow for an additional 48 h, and at 74 hrs into the experiment, cells were again transfected with siRNA and incubated another 18 hrs. At 92 hrs into the experiment, cells were inoculated with IC323-EGFP wtMV at an m.o.i of 5 for 2 hrs. Following adsorption of virus, cells were treated with citrate buffer to remove non-internalized virus, washed 3 times with PBS, incubated with DMEM containing 5% FCS at 37° C. for an additional 36 hrs, and viewed by fluorescence and phase contrast microscopy and then harvested to determine MV titres.

Virus Titration

MV-infected cell monolayers were harvested in media and subjected to one freeze-thaw cycle to release virus particles. $TCID_{50}$ titres were determined by 50% end-point titration on Vero/hSLAM cells according to the Spearman-Kärber method. Plaque assays using SeaPlaque agarose overlays were performed as previously described [76].

MV Binding Assay

CHOpgsA745 cells that stably expressed PVRL4 were generated from the pCMV6 AC-PVRL4 expression vector which contained a neomycin$^R$ selection marker. Cells were pre-treated with 15 μg/ml of either blocking PVRL4 antibody (R&D Systems AF2659) or an isotype control antibody (R&D Systems AB-108-C) for 30 minutes at 4° C. To assess the binding capacity of MV to PVRL4, CHO-PVRL4 cells were incubated with either 10 or 25 PFU/cell of MV-IC323 for 90 minutes on ice in the presence of isotype (gIgG) or blocking PVRL4 (gPVRL4) antibodies. Cells were washed three times with PBS containing 1% bovine serum albumin, 5 mM EDTA, and 0.1% sodium azide, and incubated with an anti-MV hemagglutinin antibody (Millipore MAB8905) on ice for 60 minutes. The cells were washed prior to incubation with an alexa fluor 488-conjugated goat anti-mouse antibody for 45 minutes on ice. Cells were again washed to remove any unbound antibodies, fixed in 1% paraformaldehyde, and run on a Cyan ADP Flow Cytometer (Beckman Coulter). Data were processed using FCS Express (De Novo Software). To determine the percentage of cells that had MV bound to their surface, a marker was drawn on the histogram so that the percentage of MV-bound cells in the mock sample was 1%. All samples were compared to mock. Data were graphed using GraphPad 4.0 software.

PVRL4 Down Regulation Following IC323-EGFP wtMV Infection

B95a and MCF7 cells were seeded in 6-well plates at a density of $1.5 \times 10^6$ and $7.0 \times 10^5$ cells per well, respectively. Cells were allowed to grow for 24 h and then infected with IC323-EGFP wtMV at 10 PFU/cell for 1.5 h. The virus innoculum was replaced with DMEM containing 5% FCS and 100 μM of the fusion inhibitory peptide, ZDfFG (Sigma C9405) to prevent syncytia formation. Forty-eight hours post infection, cells were harvested in non-enzymatic cell dissociation buffer (Sigma) and stained for SLAM expression using SLAM antibody (BD Biosciences) or PVRL4 expression as described above. Samples were run on a Cyan ADP Flow Cytometer (Beckman Coulter) and data processed using FCS Express (De Novo Software).

Immune Histochemistry Protocol for Staining PVRL4 in Human Tissue Sections

Formalin fixed paraffin embedded tissue was sliced at a 4 μm thickness with a microtome and dried in a 60° C. oven overnight. Sections were dewaxed in xylene and rehydrated through graded concentrations of alcohol to water. Endogenous peroxidase was blocked with 3% hydrogen peroxide. Heat induced epitope retrieval in 10 mM citrate buffer, pH 6.0 was performed in a Milestone T/T Mega microwave oven. After blocking for endogenous biotin using Vector's biotin blocking kit, sections were incubated in primary antibody (anti-Nectin-4, R&D Systems, goat polyclonal, 1:1000 dilution) for 16 hours at room temperature in a humidified chamber. After washing the sections in PBS, secondary incubations were carried out with biotin-anti-goat IgG (Vector Laboratories), followed by incubation with streptavidin-HRP (ID Laboratories) for 30 min. Antibody binding was revealed by treating the sections with DAB substrate (Dako North America, Inc) for 5 min. Samples were counterstained with Mayer's haematoxylin and mounted in Permount.

Example 1

Wild Type MV Infects Serum Activated SAEC Independently of CD46 (MCP) and CD150 (SLAM)

Human primary SAEC were previously shown to support wtMV replication and produce syncytia when grown in the presence of 2% fetal calf serum but not in serum free media. These cells did not express CD150 (SLAM) [39]. These results were confirmed and it was further demonstrated that infections with a recombinant wtMV engineered to express EGFP (IC323-EGFP wtMV) were independent of CD46 (MCP) and CD150 (SLAM) expression. Infections with IC323-EGFP wtMV were unaffected by the presence of monoclonal antibodies directed against CD46 and CD150, that were previously shown to neutralize MV infections [44, 51] (FIG. 1A). SLAM blind virus, which contains mutations in the H protein that prevents CD150 recognition, along with an EGFP reporter gene [52], also infected these cells. Marmoset cell lines do not express the critical SCR1 virus binding domain of CD46 [53,54]. Deletion of SCR1 in the marmoset SAEC was confirmed by diagnostic RT-PCR of CD46 mRNA using conserved primer sequences (FIG. 1B). However, marmoset SAEC were still susceptible to IC323-EGFP wtMV (FIG. 1B). The cells could also be infected with Edmonston-EGFP, SLAM blind and CD46 blind recombinant MV's [52] (FIG. 1B). These results provide further support for the existence of a unique MV epithelial cell receptor.

Example 2

Figure 12:
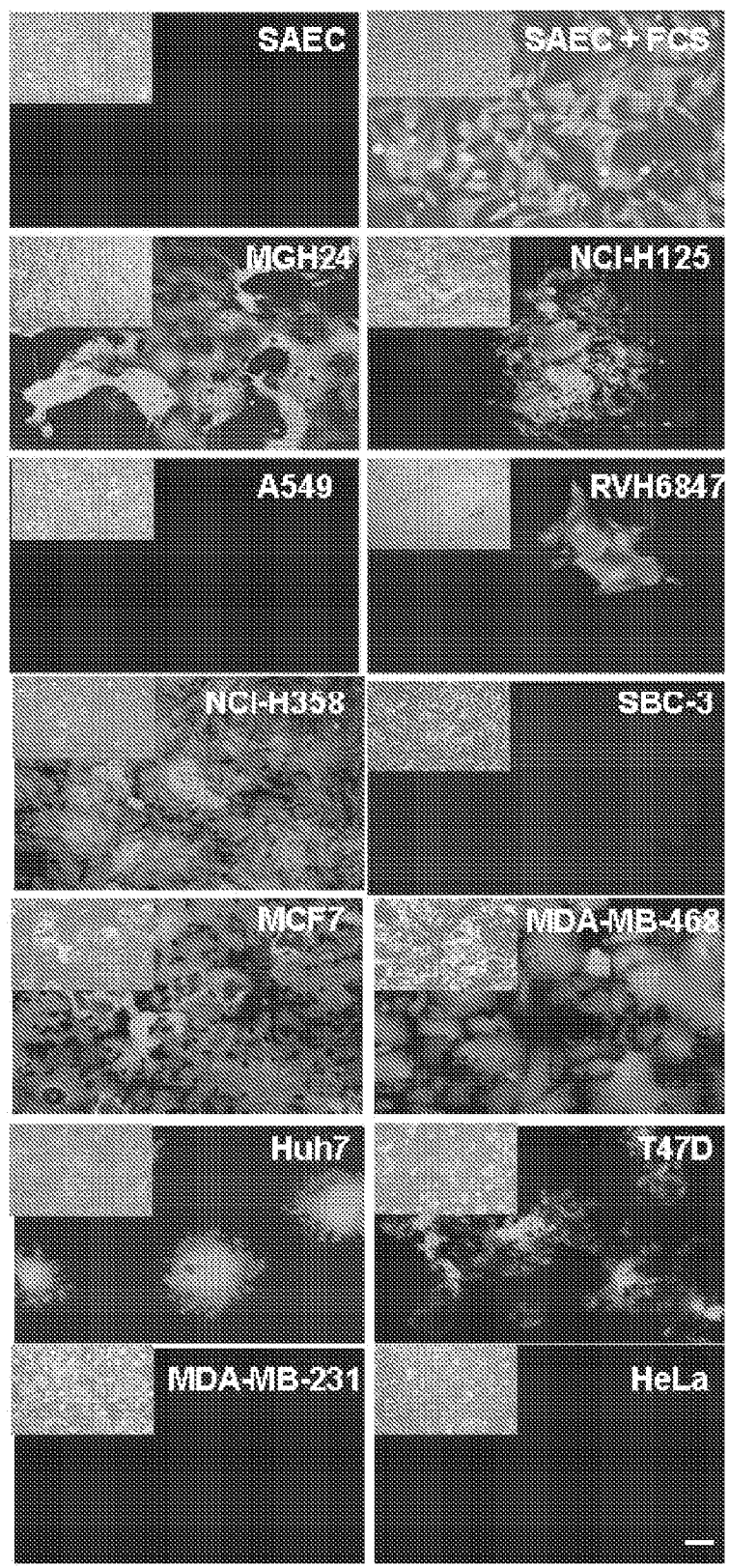
FIG. 12. Human SAEC grown in 10% fetal calf serum and many adenocarcinoma cell lines are susceptible to infection by IC323-EGFP wtMV. MGH24 (lung), NCI-H358 (lung), RVH6847 (lung), MCF7 (breast), MDA-MB-468 (breast), T47D (breast), Huh7 (liver) adenocarcinoma cell lines and SAEC (with serum) were visibly infected with the IC323-EGFP wtMV virus after 48 hrs incubation. SAEC (serum free), A549 (lung adenocarinoma), SBC-3 (small cell lung carcinoma), MDA-MB-231 (breast adencarcinoma), and HeLa (cervical carcinoma) were non-permissive for wtMV infections. Scale bar=100 μm. See also Table 1.
Figure 13:
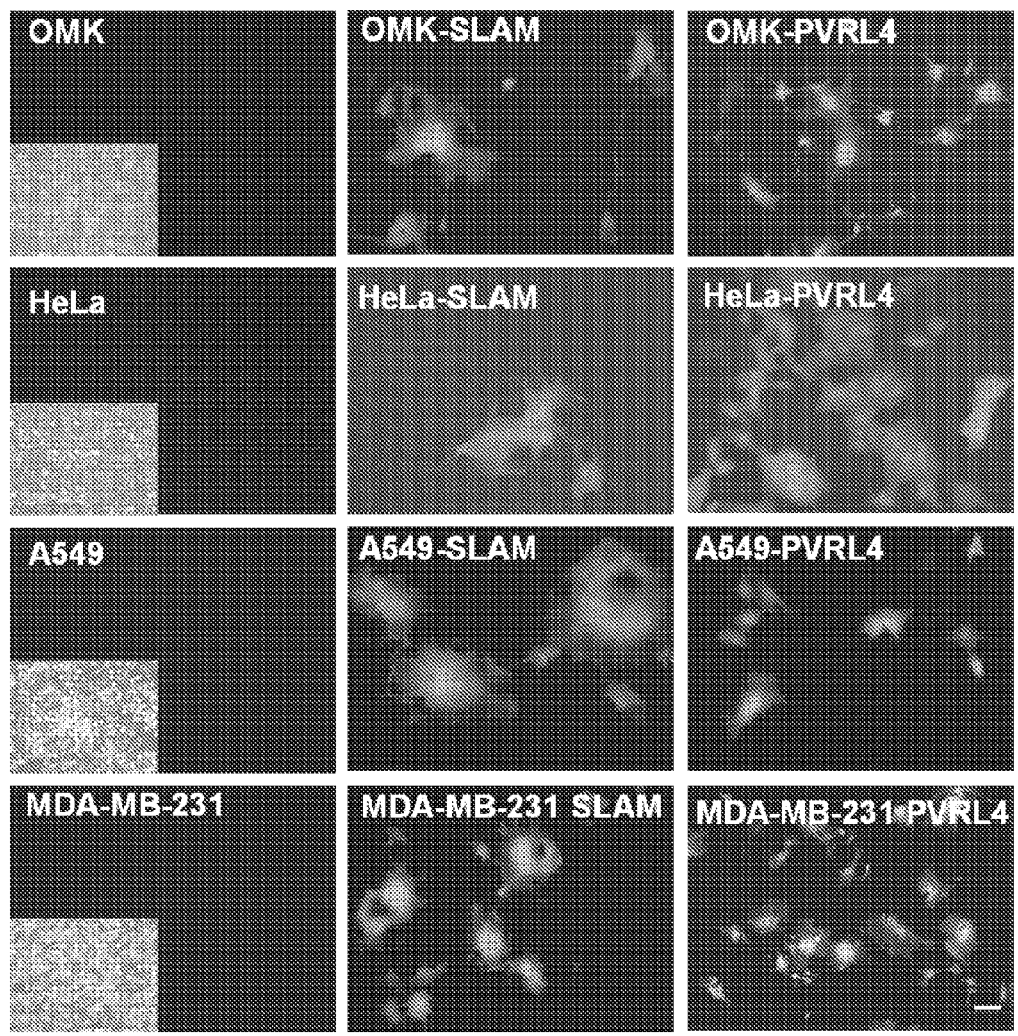
FIG. 13. PVRL4 (Nectin 4) and CD150 (SLAM) expression renders cells susceptible to IC323-EGFP wtMV. Non-permissive OMK, HeLa, A549, and MDA-MB-231 cells were transfected with expression plasmids expressing either CD150/SLAM or PVRL4 (Nectin 4) and incubated for 36 hrs. The transfected cells were infected with IC323-EGFP wtMV (m.o.i. 10) and incubated a further 48 hrs. Scale bar=100 μm. See also FIG. 3.

Wild Type MV Infects Adenocarcinoma Cells Derived from Lung, Breast, and Colon Tumors Since adenocarcinomas are defined as tumors which are derived from glandular epithelial cells, we decided to test the susceptibility of a number of different tumor cell lines to infection with IC323-EGFP wtMV. Infectivity assays were performed on 12 lung, 4 breast, 6 colon, 3 liver, 1 pancreatic, 1 cervix and 5 kidney cell lines. The relative infectivity in the different cell lines was assessed qualitatively, as the percentage of fluorescent cells due to virus-mediated EGFP expression (Table 1). Most adenocarcinomas were susceptible to IC323-EGFP MV infection, and the exceptions were A549 (lung), MDA-MB-231 (breast), HCT116 (colon), HepG2 (liver), HS766T (pancreas), and HeLa (cervix) cells, which were non-susceptible to the virus (FIG. 12). Large cell and small cell carcinoma cell lines from the lung also did not support infection. To determine whether the non-susceptible property of negative cell lines was due to the absence of a particular receptor, non-susceptible cell lines were transfected with a cDNA expression plasmid for the lymphotropic receptor CD150/SLAM. Expression of CD150 rendered A549, MDA-MB-231, HeLa, Vero, and OMK cells susceptible to IC323-EGFP wtMV, indicating that the cells were competent for MV replication, but lacked the entry protein(s) for viral infection (FIG. 13).

Example 3

Microarray Analysis Reveals that PVRL4 (Nectin 4) is a Receptor for MV

Figure 14:
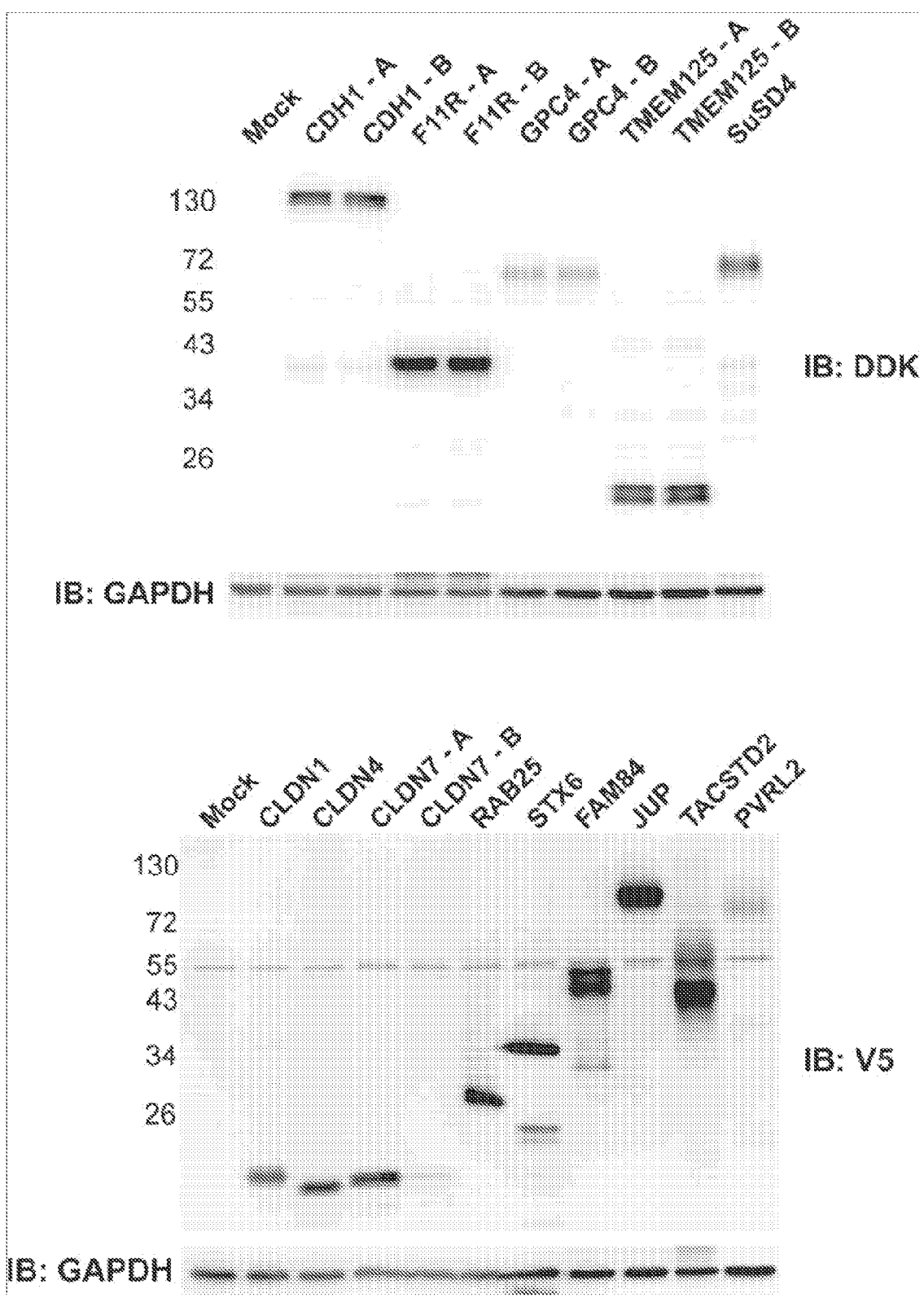
FIG. 14. Expression of (A) DDK- and (B) V5-tagged candidate receptors in COS-1 cells. COS-1 cells were transfected with expression plasmids containing the coding sequences for candidate membrane protein receptors. After 36 hrs the cells were lysed and 10 μg of whole cell lysate was separated by SDS-PAGE followed by Western immunoblot. Horseradish peroxidase-conjugated Flag antibodies (IB: DDK) or V5 antibodies (IB: V5) were incubated with the membranes and developed with enhanced chemiluminescence. (A) Duplicate expression clones of CDH1, F11R, GPC4, TMEM125, and a single clone of SUSD4 were transfected into COS-1 cells and analyzed with DDK(Flag) antibodies. These clones were purchased from Origene Systems. (B) Expression clones for CLDN1, CLDN4, CLDN7, RAB25, STX6, FAM84, JUP, TACSTD2, and PVRL2 were prepared from the Open Biosystems Plasma Membrane Donor Library using Gateway Cloning technology and LR Clonase II (see Materials and Methods). The resulting clones contained a V5 tag sequence fused to the coding sequence of a particular gene to produce a recombinant protein with a V5 tag at its carboxyl terminus. See FIG. 2 and Table 2.
Figure 16:
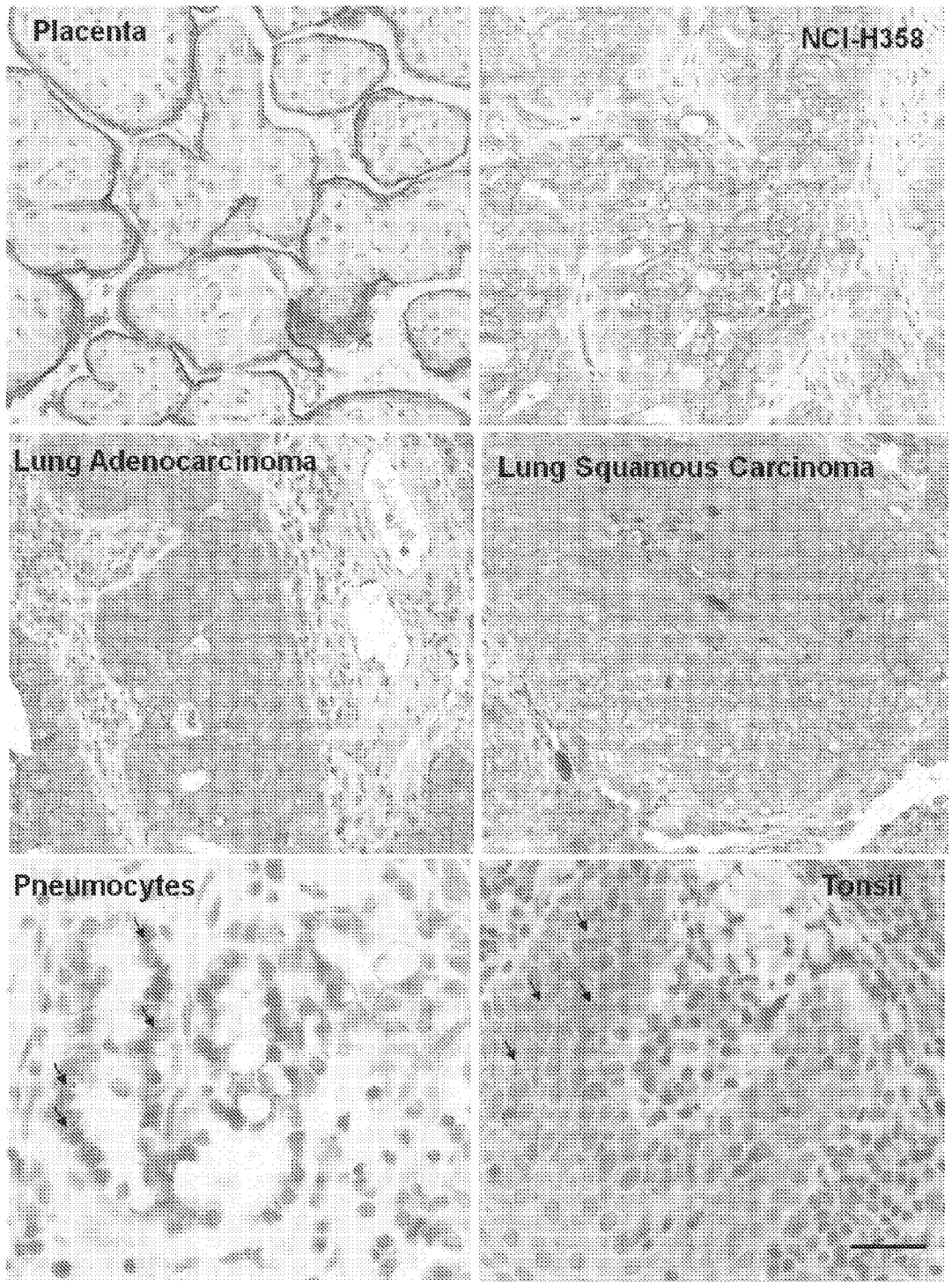
FIG. 16. Immune histological analysis of PVRL4 in human tissues. Formalin fixed paraffin embedded tissue slices from placenta, NCI-H358 xenografts grown in mice, lung adenocarcinoma, lung squamous carcinoma, reactive pneumocytes from the lung, and tonsil tissue were incubated with goat anti-PVRL4 antibody (1:1000) directed against a specific peptide sequence. Antibody binding was detected by incubating the tissue sections with biotin-anti-goat IgG, horse-radish peroxidase (HRP)-streptavidin, and diaminobenzidine (DAB) substrate. Labeled PVRL4 protein located in adherens junctions stained brown. Representative lighter staining structures in the pneumocytes and tonsils are indicated with arrows. Scale bar=100 μm. See also FIG. 6.

Microarray analysis and a comparison between susceptible and non-susceptible cells were previously used to identify the cellular receptor for Nipah virus [55]. In our case the mRNA transcripts from cells that were susceptible to wtMV infection were compared to those from non-susceptible cells using the Affymetrix Human Gene ST 1.0 Array. RNA was prepared from breast adenocarcinoma (MCF7, MD-MB-468, T47D, MD-MB-231), lung adenocarinoma (NCI-H358, MGH24, NCI-H125, A549), and SAEC (with and without serum treatment) cell lines. Following the analysis it was apparent that many of the up-regulated membrane proteins were associated with the tight junctions and adherens junctions found in polarized epithelial cells (Data not shown). Recently another laboratory reported that loss of tight junctions, during an epithelial-mesenchymal cell transition induced by the transcription repressor SNAIL, blocked receptor-dependent infections by wtMV [45]. The percentage up-regulation of gene expression for membrane proteins in susceptible cells compared to non-susceptible cells was calculated for breast, lung, and SAEC categories of cell lines (Data not shown). These values were ordered and only gene products which were up-regulated greater than 20% were considered in our analysis. Evaluation of potential receptors was conducted in 2 phases. Gene products that were up-regulated in susceptible breast adenocarcinomas were first compared to those up-regulated in susceptible lung adenocarcinomas. To investigate whether this subset of candidate receptor genes from the initial microarray screens might act as an epithelial receptor for wtMV, we cloned these genes from a cDNA library of membrane proteins from Open Biosystems (Huntsville, Ala.) or purchased the genes not represented in this library from Origene Systems (Rockville, Md.). We chose to introduce the expression plasmids into COS-1 monkey kidney cells due to their high transfection efficiency. Expression of the individual candidate receptor genes were verified by Western immunoblot analysis for the V5 peptide tag that was fused to the carboxy terminus of each membrane protein from the Open Biosystems vectors or the Myc-DDK(Flag) tag from the Origene vectors (FIG. 2, FIG. 14). At 36 hours post-transfection, COS-1 cells were inoculated with wtMV-EGFP and infections were monitored between 24-72 hours p.i. Over 48 membrane protein genes that were the most highly up-regulated in both breast and lung adenocarinoma cells were originally tested without success (indicated with * in Table 2). Subsequently, in the next phase of testing the up-regulated genes common to both breast and lung adenocarcinomas were compared to those in serum activated SAEC cells. The results are presented in Table 2, and 11 common gene products were over-expressed in all 3 tissue types. These candidate receptor genes included SLC6A14, STEAP4, TMPRSS11E, MUC1, ERBB3, PVRL4, MUC15, PCDH1, ANO1, MUC20, and CLDN7. Of these, 10 were tested (indicated with ** in Table 2) and it became immediately evident that PVRL4 could act as a receptor and facilitate infection (FIG. 2). (Both PVRL4 (Nectin 4) and the CD150/SLAM positive control yielded infections that were characterized by syncytia formation with typical MV cytopathology. A background of single infected COS-1 cells which did not fuse and form syncytia was also evident. Infections in these cells did not progress and could be due to another route of entry such as macropinocytosis. These single infected cells were previously reported in MV infected CHO and Vero monkey kidney cells and occurred at frequency of 2-3 logs below that of SLAM-dependent infections [44]. This background could not be eliminated with siRNAs directed against PVRL4 (data not shown). Expression of exogenous PVRL4 in other non-susceptible cell lines (OMK, HeLa, A549, and MDA-MB-231) also rendered them susceptible to IC323-EGFP wtMV infection (FIG. 13).

Example 4

Figure 15:
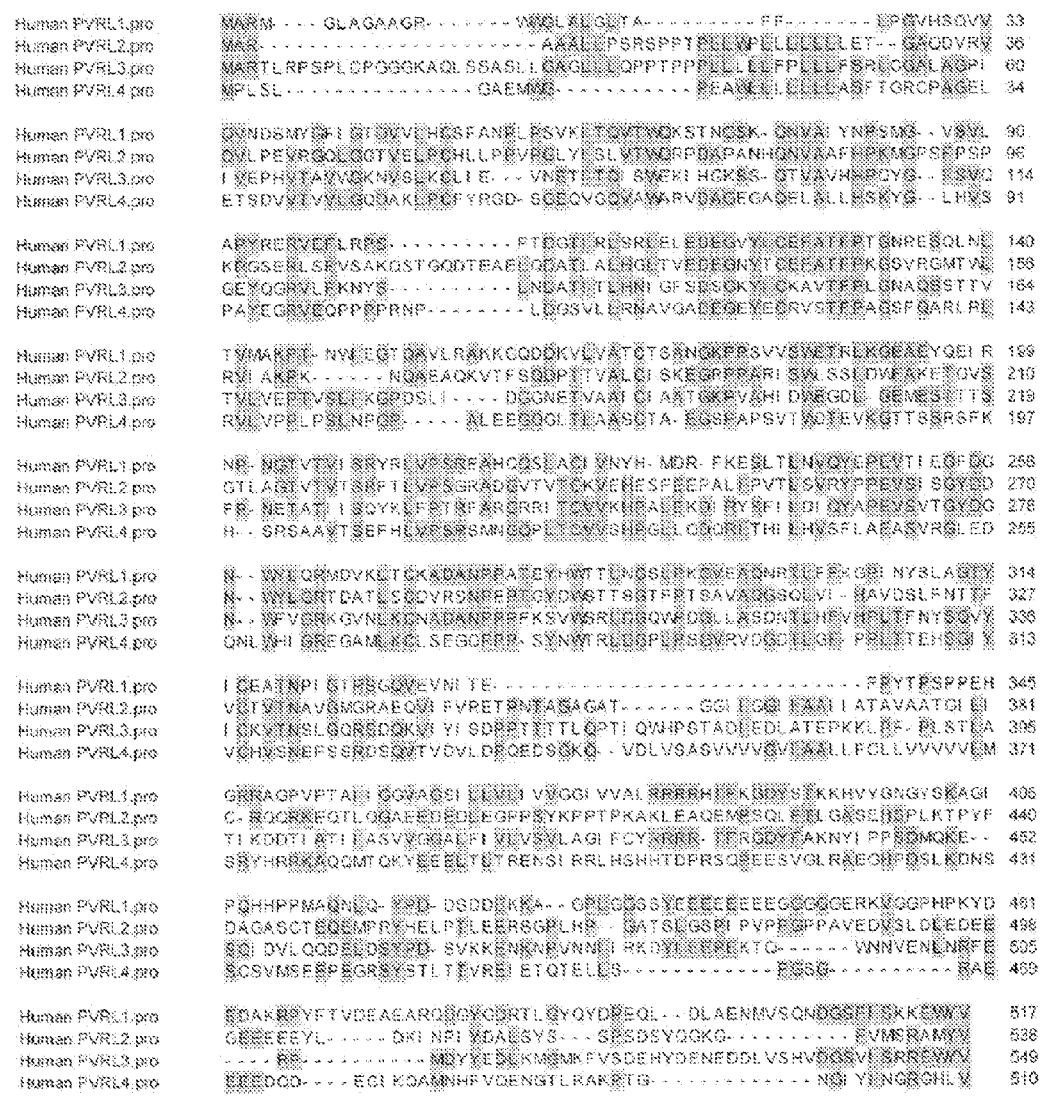

Related Proteins (PVR, PVRL1, PVRL2, PVRL2) Cannot Function as a Receptor for MV PVR, PVRL1, PVRL2, and PVRL3 are nectin proteins that are closely related in structure and sequence to PVRL4 (FIG. 15). The proteins PVR, PVRL1, and PVRL2 have previously been shown to function as receptors for polio (PVR) and herpes simplex (PVRL1, PVRL2) viruses. We tested the ability of PVR, PVRL1, PVRL2, and PVRL3 to function as receptors for MV following transfection into COS-1 cells. Fluorescence microscopy of non-permeabilized cells that over-expressed PVRL1, PVRL2, PVRL3, and PVRL4 confirmed cell surface expression of these proteins (data not shown). Only PVRL4 was capable of converting the non-susceptible cells to a wtMV susceptible phenotype (FIG. 3A).

Figure 3:
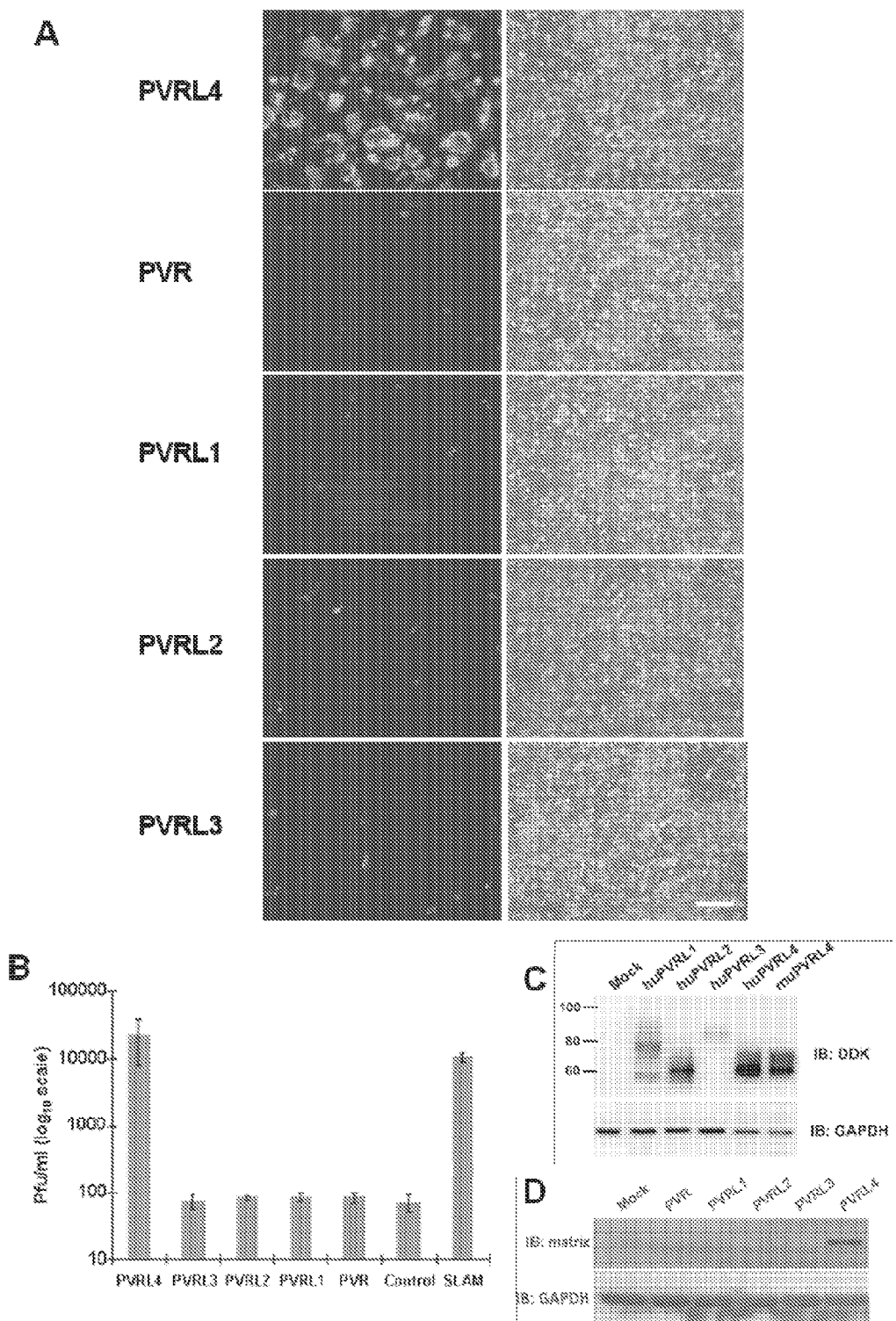
FIG. 3. Nectins closely related to PVRL4 cannot function as receptors for wtMV. COS-1 cells were transfected with expression vectors encoding DDK-tagged versions of PVR, PVRL1, PVRL2, PVRL3, and PVRL4. Control cells were transfected with empty plasmid. After 36 hrs, the transfected cells were infected with IC323-EGFP wtMV and incubated a further 48 hrs. (A) Cells were viewed by fluorescence and phase contrast microscopy. Scale bar=200 µm. (B) Virus released from the infected cells was quantified by plaque assay. Data are expressed as the mean of three independent experiments, with error bars showing the SEM. (C) Total cell expression of the transfected proteins was evaluated by Western immunoblots using antibodies directed against the DDK (Flag). (D) Viral proteins were synthesized in PVRL4 transfected cells following MV infection as shown by Western immunoblot using an antibody specific for the viral matrix (M) protein.

Infected cells expressing PVRL4 produced virus particles based upon plaque assays (FIG. 3B). Expression of the various nectin proteins was confirmed by SDS PAGE followed by immunoblot analysis using antibodies directed against the DDK tag (FIG. 3C). Cells containing PVRL4 but not the other nectins also synthesized MV proteins as shown by an immunoblot for viral matrix (M) protein (FIG. 3D).

Example 5

Figure 4:
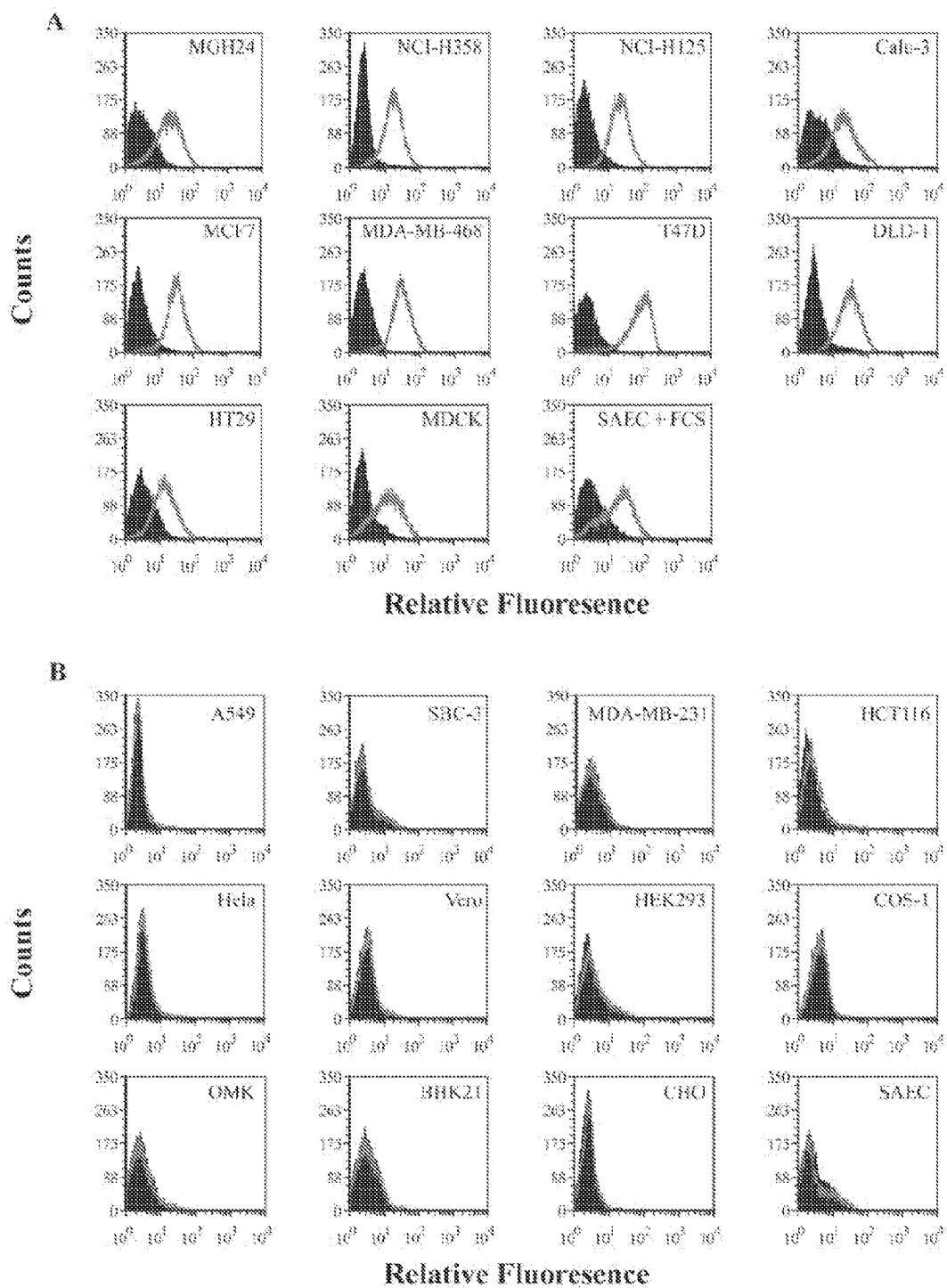
FIG. 4. Flow cytometry analysis reveals PVRL4 (Nectin 4) surface expression on cells susceptible for wild type MV infections. (A) Susceptible cell lines were incubated with a phycoerythrin-conjugated mouse monoclonal antibody that was specific for human PVRL4 (unfilled line histogram) or a PE-conjugated mouse IgG2a control antibody (shaded histogram). Cells were washed and analyzed with a Beckman-Coulter ADP Cyan flow cytometer. The Y-axis represents cell counts and the X-axis represents fluorescence intensity. (B) Non-susceptible cell lines were analyzed as described for Panel A.
Figure 6:
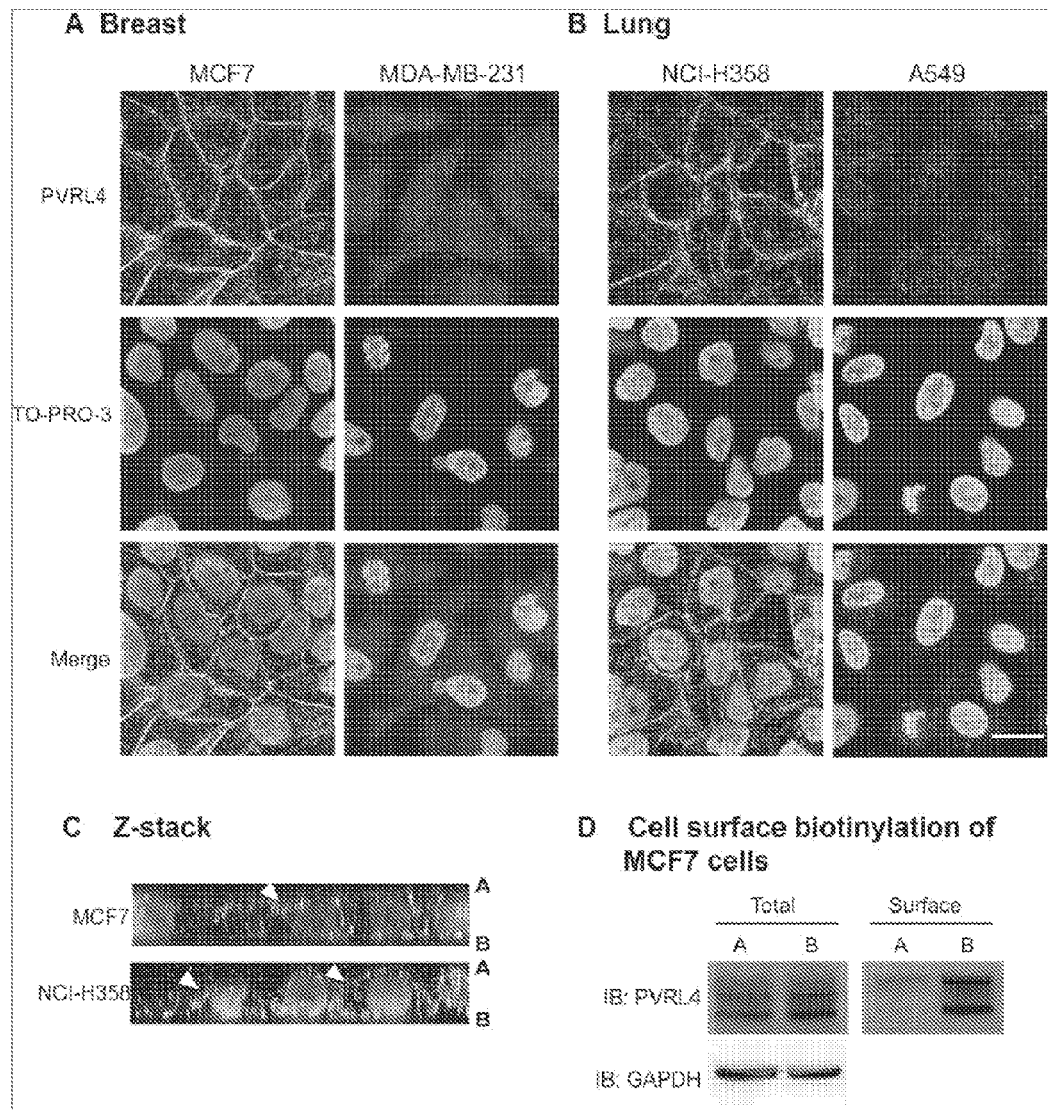
FIG. 6. PVRL4 is localized to both the apical and basolateral surfaces in MCF7 and NCI-H358 cancer cells. (A) Breast (MCF7 and MDA-MB-231) and (B) lung (NCI-H358 and A549) cancer cell lines were grown to confluence on glass coverslips and then fixed with paraformaldehye, permeabilzed, and stained with goat-anti human PVRL4 antibodies (top of A and B; PVRL4). Nuclei were visualized with TO-PRO-3 nuclear stain (Middle of A and B; TO-PRO-3). Images were captured on a Zeiss upright confocal microscope and analyzed using Zen 2008 image capture software (Zeiss). Scale bar=20 µm. (C) Z-sections of MCF7 and NCI-H358 cells stained with PVRL4 (lines) and TO-PRO-3 (circles). PVRL4 is localized to both the apical [A] and basolateral [B] surfaces of these cells. White arrowheads indicate the apical expression of PVRL4. (D) Surface biotinylation of MCF7 cells. MCF7 cells were grown for 96 h on transwell filters (24 mm diameter). The cells were incubated with NHS-biotin from either the apical (lanes A) or basolateral (lanes B) side. After lysis, surface proteins were immunoprecipitated with Neutravidin, and immunocomplexes were subjected to SDS-PAGE and Western blot for PVRL4. Glyceraldehyde 3-phosphate (GAPDH) was used as a loading control.

Susceptible but not Non-susceptible Cell Lines Express PVRL4 (Nectin 4) on Their Cell Surface Flow cytometry was used to determine whether epithelial or adenocarcinoma cells that are susceptible for wtMV infection expressed PVRL4 on their surfaces. Cells susceptible for wtMV infection bound fluorescent antibodies specific for PVRL4 (FIG. 4A). Non-susceptible cells, on the other hand, exhibited no difference in fluorescence when compared to the isotype control antibody (FIG. 4B). NCI-H358, NCI-H125, MGH24, and Calu-3 lung adenocarcinoma cells expressed PVRL4 while A549 adenocarcinoma, squamous cell (NCI-H157), small cell (SBC-3), and large cell (NCI-H460) lung carcinomas did not. MCF7, MDA-MB-468, and T47D breast adenocarcinomas were PVRL4 positive, while the non-susceptible MDA-MB-231 cells were not. Of the colon tumor cell lines, HT29, T84, and DLD-1 cells were positive for PVRL4, while HCT116 cells were negative. Other adenocarcinomas of the liver (HepG2), cervix (HeLa), and kidney epithelial cell lines were negative for PVRL4 on their surfaces. Interestingly, SAEC treated with FCS for 24 h exhibited an increased level of PVRL4 on their surface (SAEC+FCS), whereas the SAEC cultured in the absence of serum did not. Since we and others have shown that SAEC grown in the presence of serum acquire the ability to become infected with wtMV, these data suggest that PVRL4 is an authentic epithelial cell receptor for MV. MDCK cells, which were originally derived from dog kidneys, also express PVRL4 on their surface. However, they are not susceptible to wtMV infections, suggesting that differences in the protein sequence of canine PVRL4 may reduce its ability to serve as a receptor for wtMV. In all epithelia derived cell lines that were tested, the presence of cell surface PVRL4 correlates with their ability to be infected with wtMV.

Example 6

The Epithelial Cell Receptor is Expressed on the Apical and Basolateral Surfaces of Polarized Adenocarcinoma Cells Many of the epithelial cell lines susceptible to wtMV have previously been shown to be polarized. In order to determine whether the putative epithelial receptor was situated on either the apical or basal surface of the cellular monolayer, cells were cultivated on polyester Transwell filter supports (0.4 μm pore size, 24 mm diameter). Cells were ascertained to be polarized by measuring their transepitheilal electrical resistance (TEER). In uninfected cells the TEER maximized at 1200 Ω-cm$^2$ at 4 days and remained constant for 10 days from the time of initial culture. Confluent cell monolayers were infected from either the apical or basolateral side with IC323-EGFP wtMV and visualized by fluorescence microscopy. TEER remained constant over the 96 hr experiment. The virus preferentially infected both MCF7 and NCI-H358 cells via the apical route, although basolateral infection was seen at later times post infection (FIGS. 5A and 5B). To control for the ability of the virus to traverse through the membrane pores, CHO cells stably expressing PVRL4 were inoculated with wtMV from either the apical or basolateral side of the transwell filter (FIG. 5C). These non-polarized cells express PVRL4 on both their apical and basolateral surfaces. A lag in MV replication revealed by EGFP expression was observed in the basolateral infections compared to the apical infections. These data suggest that the Transwell membrane may play a role in hindering the ability of MV to infect cells via the basolateral surface. To increase the efficiency of basolateral infections, we prolonged viral adsorption times to 4 hr and decreased the stringency of washing non-adsorbed virus from the cells, but this had no effect. We concluded that wtMV could infected polarized MCF7 and NCI-H358 cells via either the apical or basolateral route, suggesting that PVRL4 is expressed on both cell surfaces.

To investigate the expression pattern of PVRL4 on adenocarcinoma cell lines, susceptible (MCF7 and NCI-H358 cells) and non-susceptible (MDA-MB-231 and A549) cells were stained with PVRL4 antibodies (FIGS. 6A and 6B). PVRL4 expression was localized to the junctions between cells in susceptible cells only. Upon further examination, PVRL4 appeared to be expressed on both the apical and basolateral side of MCF7 and NCI-H358 cells (FIGS. 6C & 6D). Surface biotinylation of MCF7 cells also confirmed that PVRL4 was expressed on both the apical and basal surfaces (FIG. 6D). Membrane proteins were biotinylated on either the apical or basolateral sides of the cell, precipitated with Neutravidin, resolved by SDS-PAGE, and PVRL4 was detected on immunoblots with specific antibodies. The data confirmed that PVRL4 was expressed on both the apical and basolateral surfaces of adenocarcinoma cell, although the band intensities did not appear to be quantitative. Apical labeling of PVRL4 did not appear to be as efficient as that of the basolateral protein. This may be due to cell surface factors such as mucous formation or glycocalyx, and this observation will require further investigation. However, the biotin labeling studies do confirm qualitatively that PVRL4 is situated on the apical surface of the cell.

PVRL4 is also localized to the cellular junctions of normal and cancerous tissues. The protein is abundantly expressed in most lung adenocarcinomas, some lung squamous carcinomas, an NIC-H358 xenograft from mice, and placenta microvilli. Reactive pneumocytes derived from normal lungs and tonsils exhibited lower levels of expression (FIG. 16). Recent reports from The Human Protein Atlas Project (see the worldwide web at: proteinatlas.org) have shown that PVRL4 is expressed abundantly in placental trophoblasts, glandular cells of the stomach, and adenocarcinomas of the lung, breast, and ovary. According to this study, moderate amounts of this protein are expressed in the epithelium of tonsils, oral mucosa, esophagus, and the respiratory cells of the nasopharynx. Smaller amounts are expressed in the lung macrophages and neuronal cells of the cerebral cortex.

Example 7 siRNA Directed Against PVRL4 Blocks Infections by MV

To investigate whether PVRL4 was a bona fide receptor for wtMV, siRNA against PVRL4 was used in the susceptible MCF7 and NCI-H358 cell lines. A pool of siRNA specific for PVRL4 or a scrambled siRNA control were transfected into MCF7 or NCI-H358 cells for 72 hrs. FACS analysis demonstrated that PVRL4 surface expression was effectively reduced following siRNA knockdown (FIG. 7A). The cells were subsequently infected with IC323-EGFP wtMV and fluorescence was monitored after further 48 hrs incubation, at which point virus was harvested. Scrambled siRNA did not inhibit MV infections (FIGS. 7B, 7C) while PVRL4 siRNA treatment clearly blocked the fluorescence produced by MV. Virus released from siRNA-treated MCF7 and NCI-H358 cells was subsequently quantified on Vero/SLAM cells. A decrease in approximately 1-2 logs was consistently seen when PVRL4 expression was knocked down prior to MV infection. The siRNA inhibition experiments conclusively demonstrated that unrestricted PVRL4 surface expression was essential for wtMV infection.

Example 8

Antibodies Specific for Human PVRL4 Inhibit MV Infection in MCF7 Cells

MCF7 cells grown on glass coverslips were incubated with 10 μg/ml non-immune goat IgG (FIGS. 8A and 8B) or goat anti-PVRL4 (FIGS. 8C and 8D) for 30 min prior to, and during 1 hr adsorption with IC323-EGFP MV via the apical surface. Fluorescence and syncytia formation due to viral infection at 48 hrs was inhibited by the PVRL4 antibody treatment. To determine whether antibodies directed against PVRL4 also blocked infection by the basolateral route, MCF7 cells were grown on Transwell permeable filter supports as described in FIG. 5. Cells were incubated with 25 μg/ml goat IgG on the apical (FIGS. 8E, 8F, 8G, and 8H) or basal (FIGS. 8I, 8J, 8K, and 8L) surfaces with antibodies directed against human PVRL4 or non-immune antibodies for 30 min and subsequently inoculated with IC323-EGFP MV (m.o.i. 10) for 4 hrs also in the presence of antibody. Infections proceeded for 72 hrs and cells were viewed by fluorescence and bright field microscopy. Interaction of goat polyclonal antibodies with PVRL4 blocked MV infection of MCF7 cells when applied via either the apical or basal routes. This inhibition indicated that MV can infect adenocarcinoma cells in a PVRL4-dependent manner by either the apical or basolateral route. The antibody inhibition provided further corroboration of RNA interference studies directed against PVRL4.

Example 9

PVRL4 Acts as an Attachment Receptor for MV

Figure 8:
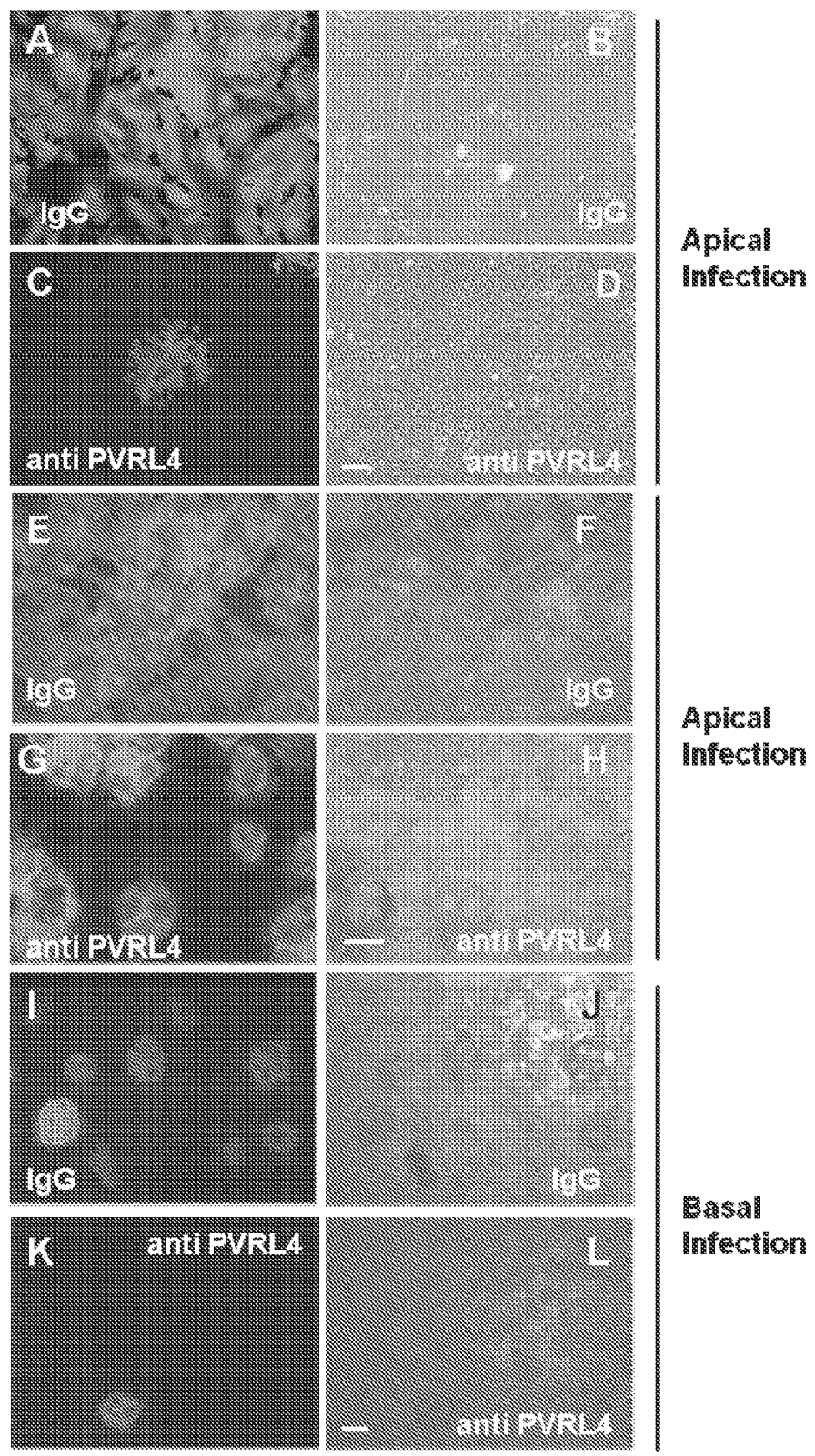
FIG. 8. Antibodies specific for human PVRL4 inhibit wtMV infection in MCF7 cells. MCF7 cells grown on glass coverslips were incubated with 10 µg/ml goat IgG (A,B) or goat anti-PVRL4 (C,D) for 30 min prior to, and during 1 hr adsorption with IC323-EGFP MV via the apical surface. Fluorescence and syncytia formation due to viral infection at 48 hrs was inhibited by the PVRL4 antibody treatment. To determine whether PVRL4 antibodies would also inhibit MV infections via the basolateral route, MCF7 cells were grown on Transwell permeable filter supports as described in FIG. 5. Cells were incubated with 25 µg/ml goat IgG on the apical (E,F,G,H) or basal (I,J,K,L) surface with antibodies specific for human PVRL4 or non-immune antibodies (IgG) for 30 min. Cells were subsequently inoculated with IC323-EGFP MV (m.o.i. 10) for 4 hrs, also in the presence of antibody. Infections were allowed to proceed for 72 hrs and cells were viewed by fluorescence and bright field microscopy. The interaction of goat polyclonal antibodies with PVRL4 blocked MV infection of MCF7 cells via either the apical or basal routes. Scale bar=100 µm.

To assess the ability of MV to bind PVRL4, CHOpgsA745 cells, which lack heparan and chondroitin sulfate on their surface, were designed to stably express PVRL4 (CHO-PVRL4). Flow cytometry with a monoclonal antibody specific for human PVRL4 indicated extensive surface expression of this protein on the CHO-PVRL4 cells (FIG. 8A, inset). CHO and CHO-PVRL4 cells were incubated with wtMV in the presence of blocking antibodies to PVRL4 (gPVRL4) or an isotype control (gIgG). Interestingly, background wtMV binding was consistently ~15-30% in CHO cells irrespective of whether the blocking antibody to PVRL4 was present (FIG. 4A, CHO; FIG. 4B). In CHO-PVRL4 expressing cells, however, there was a shift in the histogram peak in the gIgG+ wtMV treatment, indicating that wtMV had bound to these cells. When blocking antibodies to PVRL4 were present, the MV binding decreased to background levels seen in the CHO cells (FIG. 4B, compare CHO-huPVRL4 gIgG Ab to gPVRL4 Ab) irrespective of the MOI used. These data suggest that PVRL4 is an attachment receptor for wtMV. The CHO-PVRL4 cells were subsequently infected with various multiplicities of infection (MOI) of IC323-EGFP wtMV for 48 h (FIG. 8C). An increase in the level of wtMV replication was detected with increasing amounts of MV in the CHO-PVRL4 cells, but only background infections were seen in the CHO cells lacking PVRL4. These results clearly establish PVRL4 as an attachment receptor for MV.

Example 10

Figure 9:
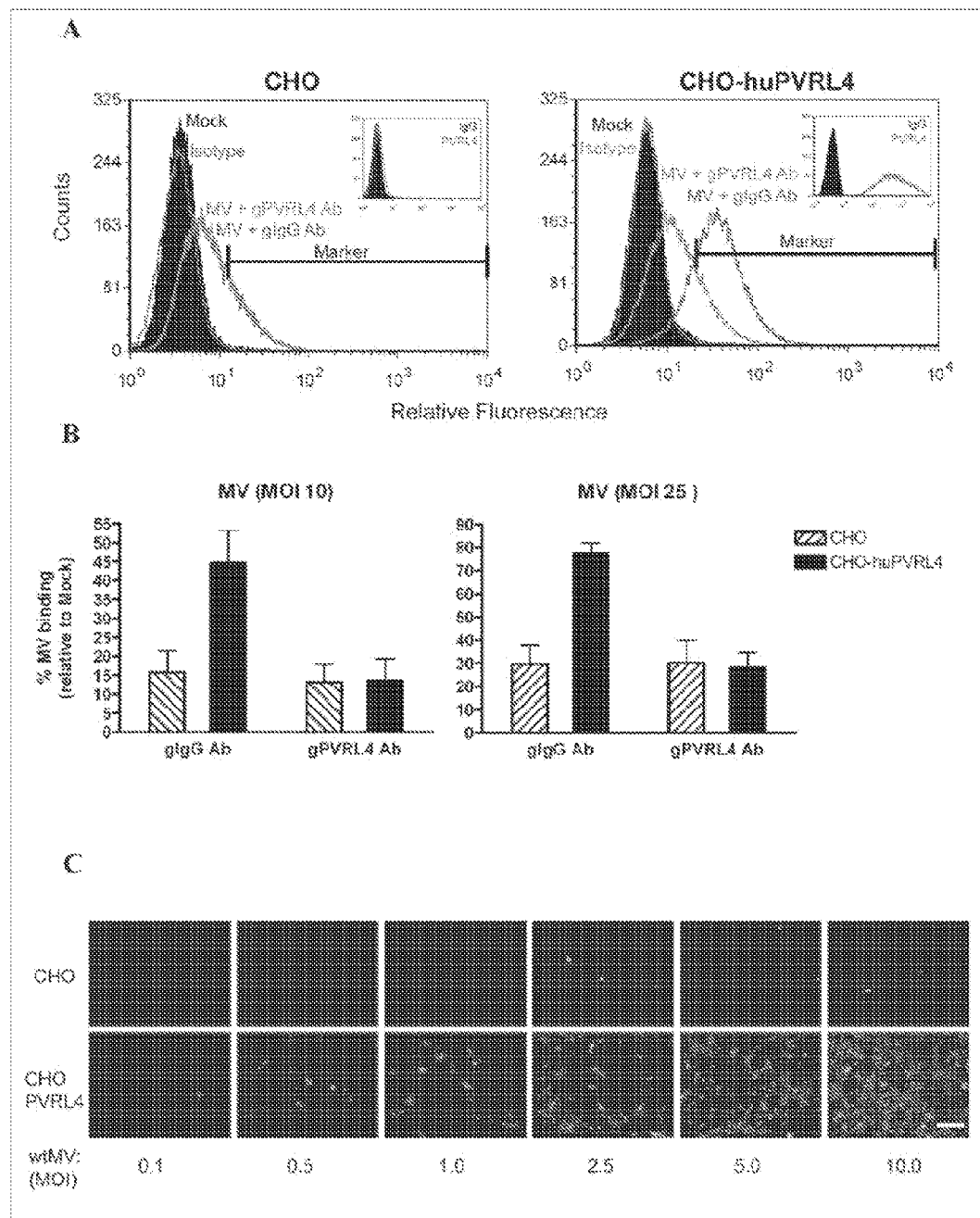
FIG. 9. IC323 wtMV binds to cells that stably express human PVRL4. CHO or CHO stably expressing human PVRL4 (CHO-huPVRL4) were incubated with either 10 or 25 PFU/cell of IC323-EGFP wtMV in the presence of isotype (gIgG Ab) or blocking antibodies against PVRL4 (gPVRL4 Ab) for 1.5 h. Cells were incubated with a MV anti-H primary antibody followed by a anti-mouse alexa fluor 488 conjugated secondary antibody to detect MV-bound cells. (A) Binding of IC323 wtMV to cells stably expressing PVRL4 was detected by FACS. CHO and CHO-huPVRL4 cells were inoculated with MV in the presence of blocking antibody against PVRL4 (gPVRL4, middle line in far right panel) or an isotype control (gIgG, far right line in far right panel), washed, and incubated with anti-MV hemagglutinin antibody or an isotype matched control antibody (green line). Cells incubated in the absence of virus (Mock, filled histogram) were stained with anti-MV hemagglutinin antibody. Bound MV-specific primary antibody was detected with alexa fluor 488-conjugated goat anti-mouse secondary antibody. The relative fluorescence intensity was measured on a Cyan ADP Flow Cytometer. Inset: Receptor expression was detected with a PE-conjugated PVRL4 antibody (unfilled line histogram) or isotype control (filled histogram). (B) Quantification of MV binding to CHO cells expressing huPVRL4 in the presence of blocking antibody to PVRL4 (gPVRL4 Ab). The percentage of MV-bound cells compared to mock cells was determined using FCS express (De Novo software). Data are expressed as the mean from three independent experiments, with error bars showing the SEM. (C) Infection of CHO and CHO-huPVRL4 cells with varying multiplicities of infection using IC323-EGFP wtMV. Images were captured 48 h post infection. Scale bar=500 µm.

Mouse PVRL4 Functions Less Efficiently as a Receptor for MV than the Human Homologue Mouse PVRL4 shares 92% amino acid sequence identity with the human homologue (FIG. 17). Expression vectors containing the cDNA sequences for the Myc-DDK tagged versions of human and mouse PVRL4 were transfected into COS-1 cells. These cells were infected with IC323-EGFP wtMV and viewed by fluorescence microscopy at 48 hrs post-infection (FIG. 9A). COS-1 cells expressing mouse PVRL4 were less susceptible to infection by IC323-EGFP wtMV and produced smaller and fewer syncytia than cells transfected with the human homologue (FIG. 9A). Virus released from the infected cells was compared using quantitative plaque assays. As expected, COS-1 cells transfected with mouse PVRL4 produced less MV than cells transfected with the human PVRL4 homologue (FIG. 9B). These results were consistent over the course of 4 separate experiments. Expression levels of mouse PVRL4 were compared to human PVRL4 by immunoblot analysis with antibodies specific for the Myc-DDK tags and were found to be similar. Surface expression of mouse and human forms of PVRL4 were also comparable (FIG. 9C). Finally, MV proteins were synthesized in the infected cells as shown by a Western immunoblot using antibodies directed against the matrix (M) protein (FIG. 9D).

Example 11

Other MV Strains can Also Use PVRL4 (Nectin 4) as a Receptor

Figure 18:
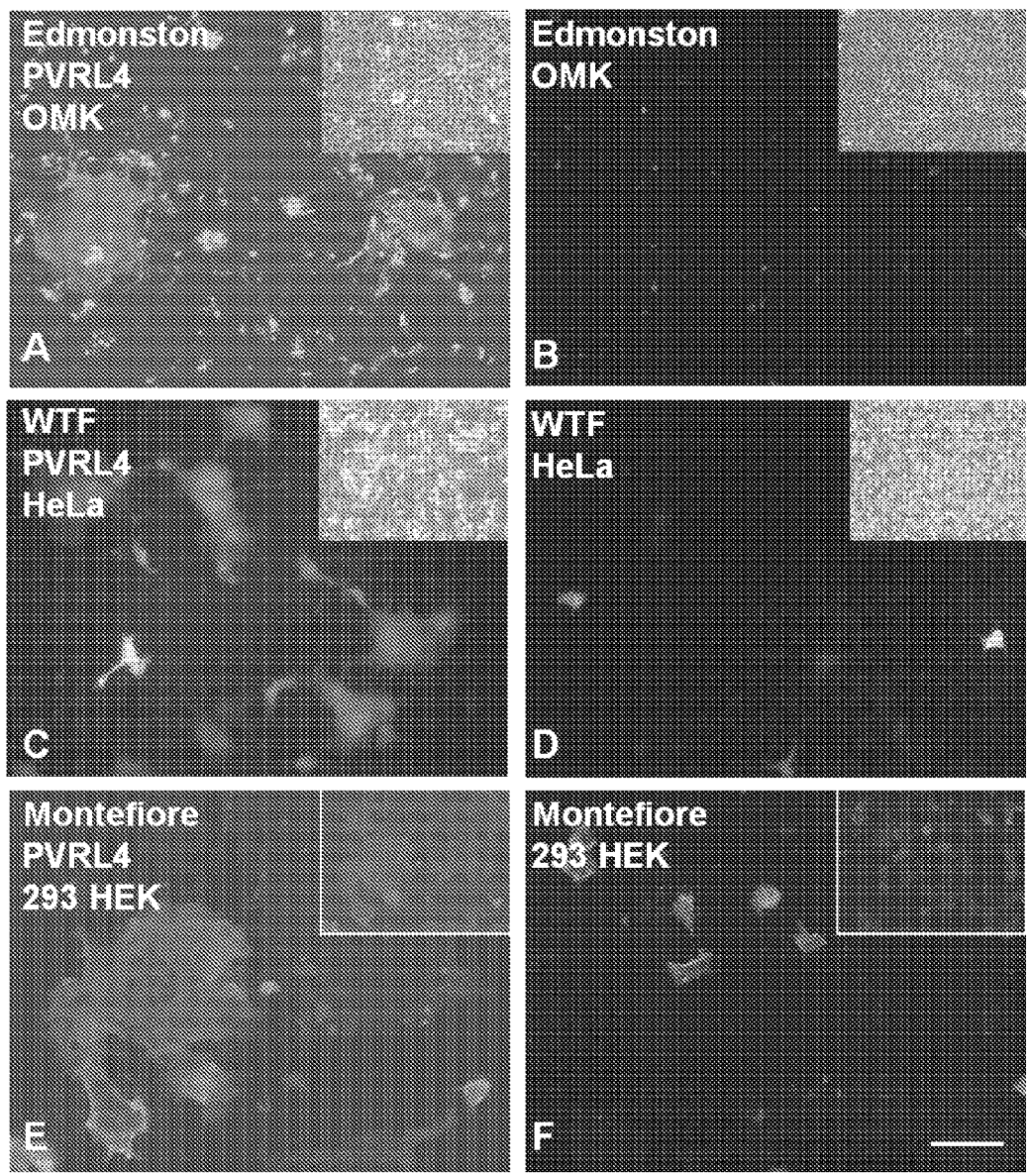
FIG. 18. Other wild type strains of MV (Montefiore 89 and WTF) and the Edmonston vaccine strain of MV can also use PVRL4 as a receptor. (A,B) Following transfection of the PVRL4 expression vector, OMK (owl monkey kidney) cells which lack a complete CD46 receptor, became susceptible to Edmonston vaccine MV. (C,D) HeLa cells transfected with the PVRL4 expression plasmid became susceptible to WTFH-EGFP MV infection. (E,F) HEK (293) cells transfected with PVRL4 become permissive to Montefiore 89 wtMV infections. In this case cells were fixed with paraformaldehyde, permeabilized with 0.1% TX-100 detergent, and stained with measles (H, M) antibodies and detected with Alexa Fluor 488 conjugated goat anti-mouse secondary antibodies. Nuclei were stained with Hoechst stain. Scale bar=100 μm. See also FIGS. 2, 12, and 13.

Other strains of MV were tested for their ability to use PVRL4 as a cellular receptor. The Edmonston-EGFP vaccine strain, WTF-EGFP wtMV, and Montefiore 89 wtMV, were inoculated onto cells transfected with the human PVRL4 expression vector. In the case of Edmonston-EGFP MV, we chose to use owl monkey kidney (OMK) cells, which are known to be deleted for the critical SCR1 domain of CD46, and are normally resistant to infection by vaccine strains of MV [53]. The WTF-EGFP wtMV and Montefiore 89 wtMV cannot use CD46 as a receptor, and were inoculated onto HeLa and 293 HEK cells, respectively, that expressed PVRL4. In both experiments, expression of PVRL4 converted the non-susceptible OMK and COS-1 cells to a MV susceptible phenotype. Cells infected with Montefiore 89 wtMV were fixed with paraformaldehyde and incubated with antibodies specific for MV proteins (H, M). Infections were detected by EGFP fluorescence or anti-measles H, M immune fluorescence microscopy (FIG. 18).

Example 12

Figure 10:
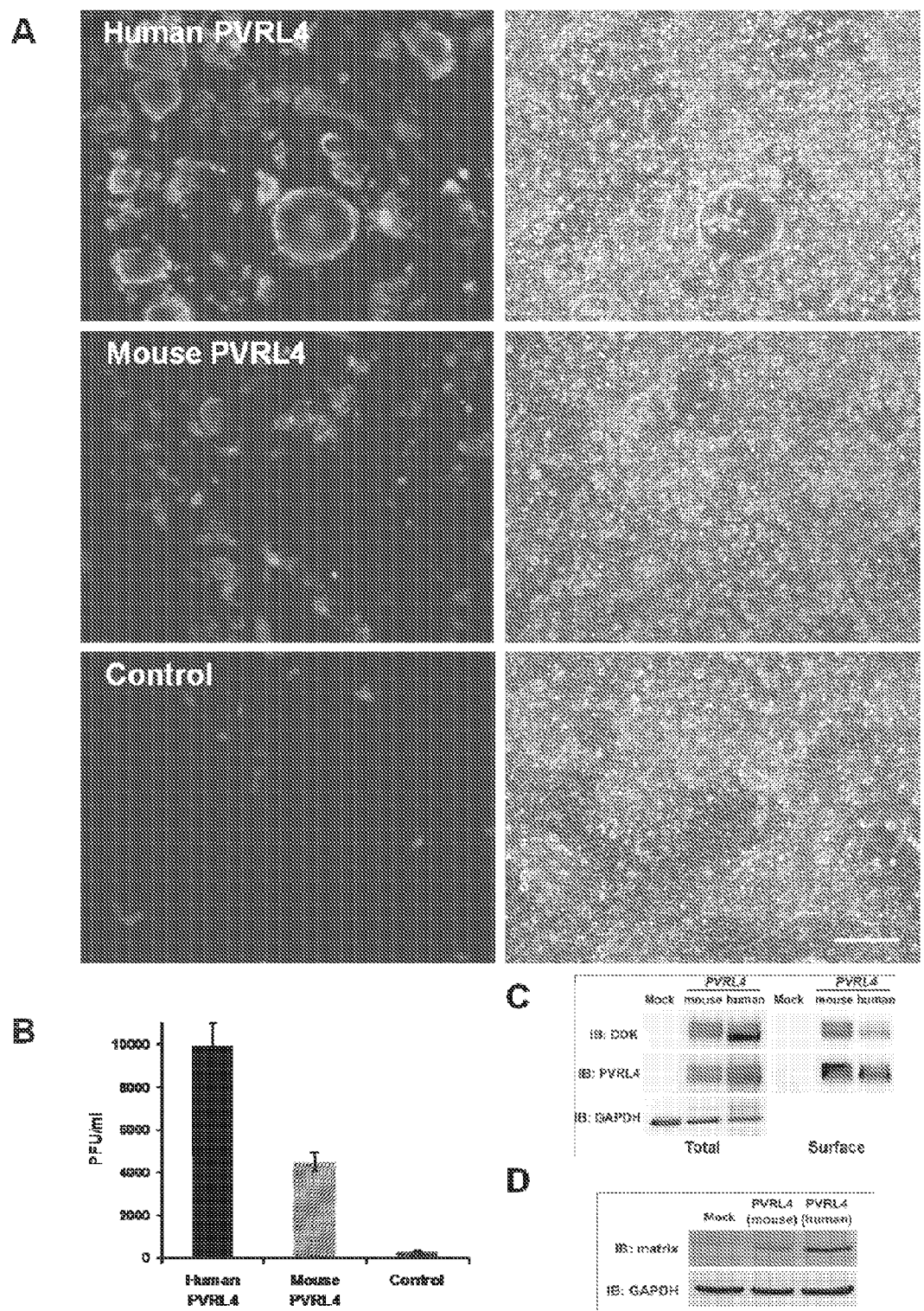
FIG. 10. Mouse PVRL4 functions less efficiently as a MV receptor than the human homologue. COS-1 cells were transfected with expression vectors encoding DDK-tagged human and mouse homologues of PVRL4. Control cells were transfected with empty plasmid. After 36 hrs, the transfected cells were infected with IC323-EGFP wtMV and incubated a further 48 hrs. (A) Cells were viewed by fluorescence and phase contrast microscopy. Scale bar=200 µm. (B) Virus released from the infected cells was quantified by plaque assay. Data are expressed as the mean from four independent experiments, with error bars showing the SEM. (C) Total and cell surface expression was evaluated by Western immunoblots using antibodies directed against the DDK(Flag) tag or PVRL4. Surface expression was evaluated following biotinylation of plasma membrane proteins. (D) Viral proteins were synthesized in PVRL4 transfect cells following MV infection as shown by Western immunoblot using an antibody specific for the viral matrix (M) protein.
Figure 11:
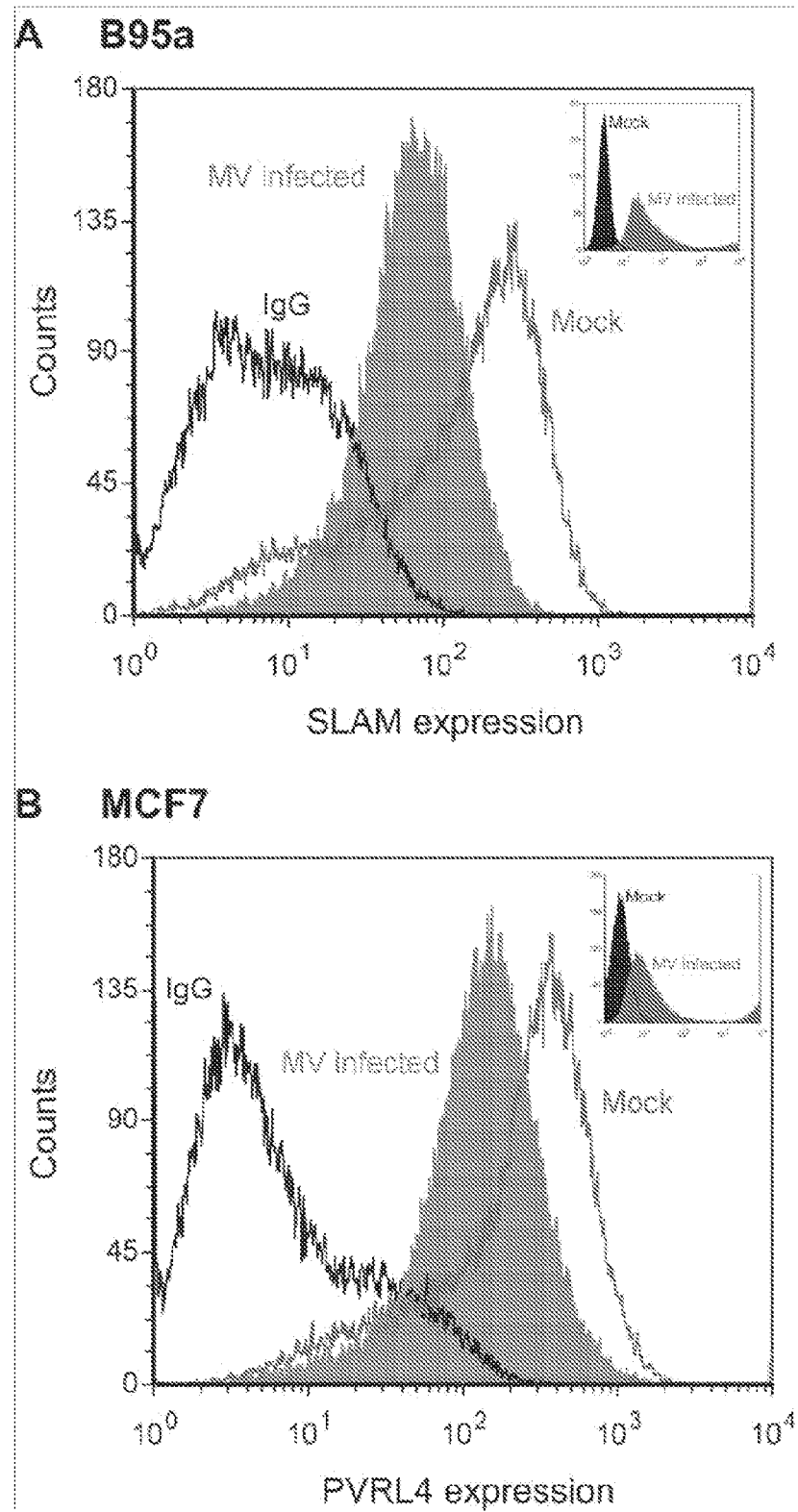
FIG. 11. Surface PVRL4 expression is down regulated following wtMV infection. A activated marmoset B-cell line B95a or B MCF7 cells were infected with IC323-EGFP wtMV. The fusion inhibitory peptide (FIP) was added after the initial virus infection to prevent syncytia formation. At 48 h post-infection SLAM and PVRL4 surface expression was analyzed by FACS. Far right lines, mock-infected cells stained with alexa anti-SLAM antibody (A) or anti-PVRL4 antibody (B); far left lines, mock infected cells stained with the anti-mouse IgG2B isotype control antibody; filled middle histogram, cells infected with IC323-EGFP wtMV (MOI 10) and stained with anti-SLAM (A) or anti-PVRL4 (B) antibodies, respectively. Alexa fluor conjugated 647 secondary antibodies were used to detect SLAM and PVRL4 surface expression. Insets, level of eGFP positive cells following a 48 h infection with IC323-EGFP wtMV. The filled right histogram represents wtMV-infected cells; black left side lines represent mock-infected cells.

PVRL4 Surface Expression is Down Regulated in MCF7 Cells Following wtMV Infection An important aspect of MV infection is the down regulation of CD46 and SLAM from the cell surface following MV-H expression [56,57,58,59,60] To determine whether PVRL4 expression was down regulated in a similar manner, FACS analysis of PVRL4 surface expression was performed at 48 h post infection. Infection by IC323-EGFP wtMV (FIG. 10B) in the presence of the fusion inhibitory peptide caused a decrease in the level of PVRL4 surface expression. Similar results were seen in B95a cells when SLAM surface expression was examined following wtMV infection (FIG. 10A). The level of MV replication was assayed by the presence of GFP positive cells (FIG. 10, inset). At 48 h post infection more GFP positive cells were seen in the MV-infected B95a cells compared to the MV-infected MCF7 cells. Taken together, these data suggest that like SLAM (CD150), PVRL4 is also down regulated following wtMV infection.

Example 13

MDA-MB-468 Tumour Xenograft Model

NU/NU (Charles River Laboratories strain code 088) nude mice were anesthetized and injected subcutaneously with 2.0×106 MDA-MB-468 breast cancer cells diluted in 50% matrigel (BD Biosciences #356231) in the right hind flank. Forty six days (~6.5 weeks) post injection of tumour cells, measurable tumours were palpable in 2 of 3 mice injected (volume of tumours averaged ~400 rnm2).

Figure 19:
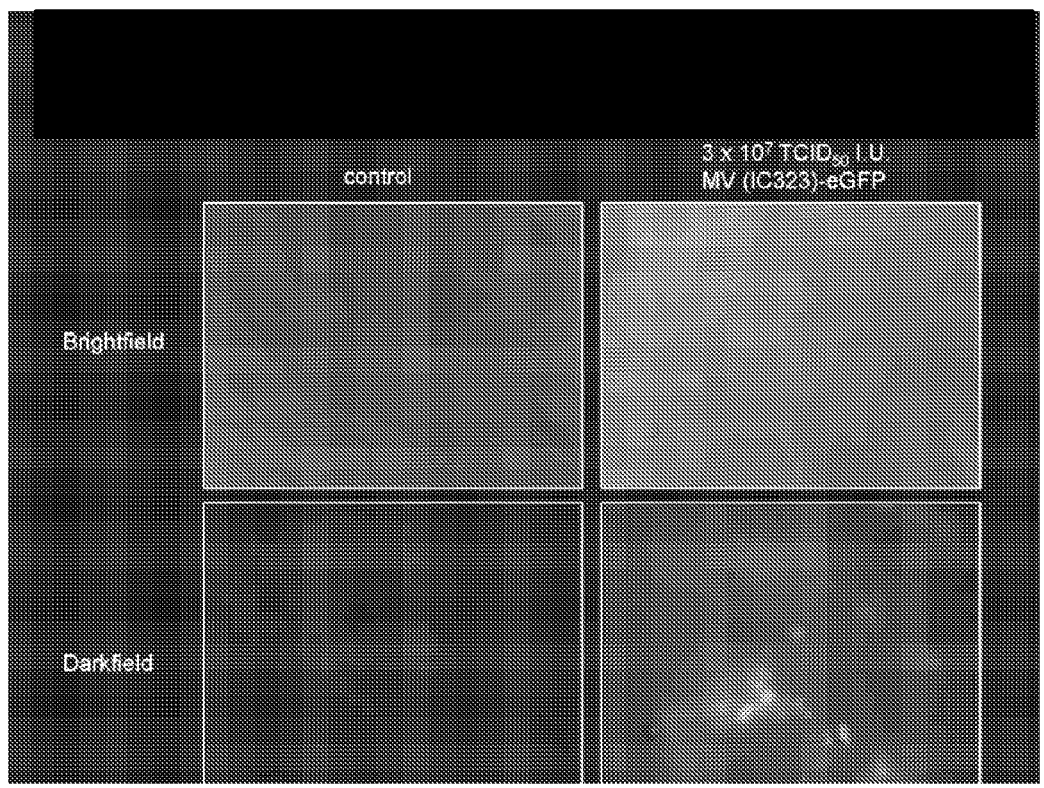
FIG. 19. Measles virus infects and replicates in human MDA-MB-468 breast cancer tumors grown in vivo in nude mice.

Fifty microliters (2-25 ul injections) of rMV-IC323-eGFP was injected intratumorally (3.0×10$^7$ TCID50 per mouse) at two sites. The mice were euthanized 6d post infection with rMV and the tumours were removed. Images of whole tumours were captured on a Leica DMI4000B (FIG. 19) to visualize MV replication (as indicated by GFP signal; See lower right panel). FIG. 19 shows that measles virus infects and replicates in human MDA-MB-468 breast cancer tumors grown in vivo in nude mice.

Example 14

DLD1 Tumour Xenograft Model in NIH III and NOD/SCID Mice

Two different strains of immunodeficient mice were used in this next set of experiments. NIH III nude mice (Charles River Laboratories strain code 201) and NOD/SCID mice (Charles River Laboratories strain code 394) were anesthetized and injected subcutaneously with 4.0×10$^6$ DLD1 colon carcinoma cells diluted in 50% matrigel (BD Biosciences #356231) in the right hind flank. Eighteen days (~2.5 weeks) post tumour cell injection measurable tumours were palpable in all of the mice injected (volume of tumours in NIH III nude mice averaged 250 mm2; volume of tumours in NOD/SCID mice averaged 450 mm2).

Fifty microliters (2-25 ul injections) of rMV-IC323-eGFP was injected intratumorally (3.0×107 TCID50 per mouse) at two sites. The mice were euthanized 8 d post infection with rMV and the tumours were removed. Tumours were fixed in 4% paraformaldehyde at 4° C. for 48 h, followed by a 24 h incubation in 30% sucrose solution at 4° C. for 24 h. The tumours were mounted in optimal cutting temperature (OCT) media, and frozen at −20° C. Tumour cryosections were prepared at a thickness of 5-10 um, mounted onto coated glass slides and allowed to dry for ~24 h at RT in the dark. The slides were rehydrated in phosphate buffered saline (PBS) for 10 minutes, followed by a 15-minute incubation in Hoescht 33258 (0.2 ug/ml) to counterstain nuclei. Slides were washed in PBS and glass coverslips were applied using Prolong Gold antifade mounting media. The coverslips were subsequently sealed with clear nail polish.

Figure 20:
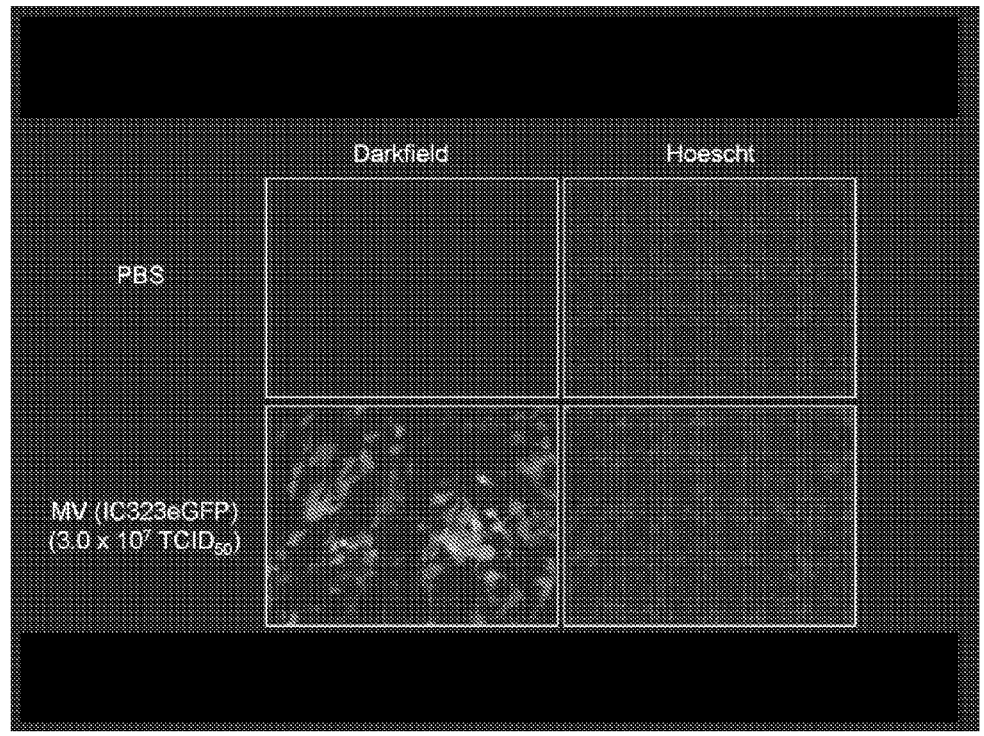
FIG. 20. Measles virus infects and replicates in human DLD-1 colon cancer tumors grown in vivo in NIH III nude mice.
Figure 21:
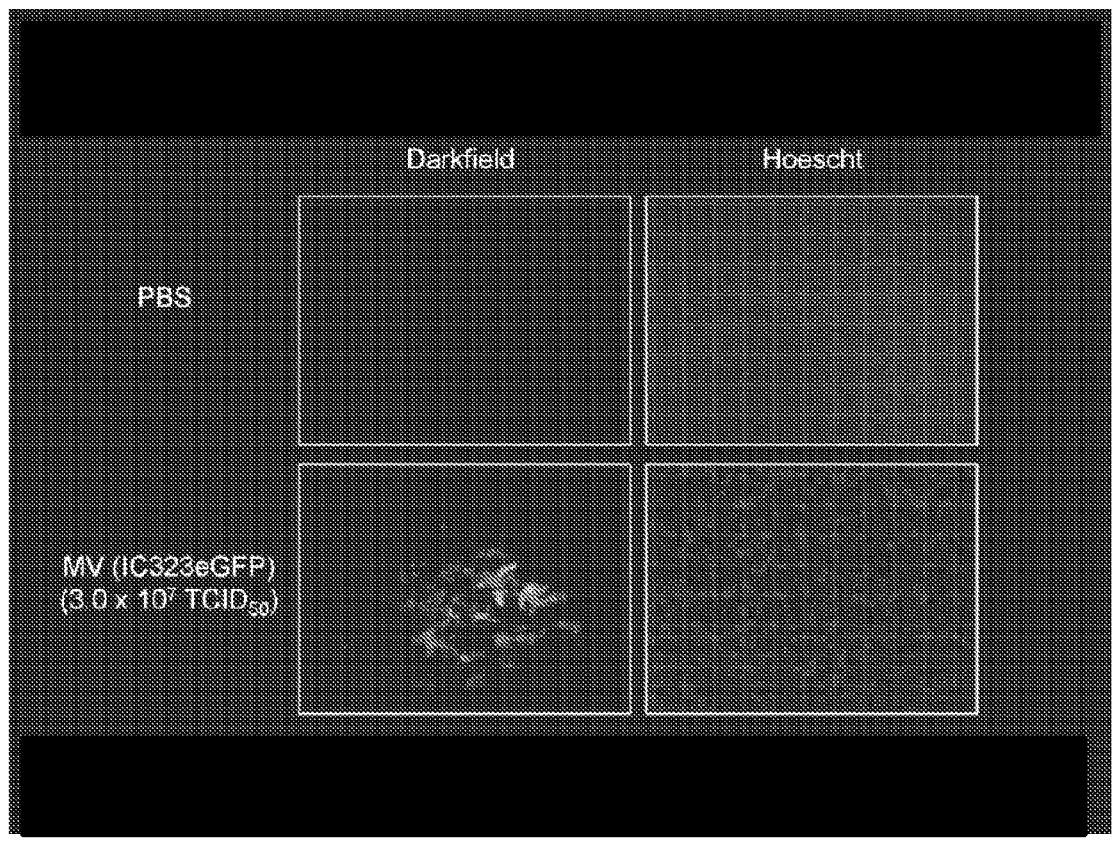
FIG. 21. Measles virus infects and replicates in human DLD-1 colon cancer tumors grown in vivo in NOD/SCID mice.

Images were acquired on a Leica DM4000B epifluorescence microscope to detect nuclei (Hoescht stain) and rMV replication (GFP signal) (FIGS. 20-21). FIG. 20 shows that measles virus infects and replicates in human DLD-1 colon cancer tumors grown in vivo in NIH III nude mice. FIG. 21 shows that measles virus infects and replicates in human DLD-1 colon cancer tumors grown in vivo in NOD/SCID mice. Thus, various human tumors are susceptible to measles virus infection in vivo and are efficiently infected throughout the tumor as evidenced by extensive spread of MV-eGFP reporter fluorescence throughout the tumors.

Therefore, PVRL4 (Nectin 4) was demonstrated to be the elusive epithelial receptor for MV. PVRL4 is expressed at low levels in normal tissues but is highly up-regulated on the surfaces of adenocarcinoma cells.

Example 15

Treatment of a Human with Virus

A human subject is treated with a virus (e.g., a measles virus) to treat a condition such as cancer (e.g., an adenocarcinoma). In some instances, one or more additional agents or viruses are co-administered. A subject in need of treatment is selected or identified based on PVRL4 expression on one or more cells of interest. The identification of the subject can occur in a clinical setting, or elsewhere, e.g., in the subject's home through the subject's own use of a self-testing kit or by a third party. At time zero, a suitable first dose of virus is administered to the subject. The virus is formulated as described herein. After a period of time following the first dose, e.g., 7 days, 14 days, and 21 days, the subject's condition is evaluated. This measurement can be accompanied by a measurement of MV infection (e.g., cfu) in said subject, and/or the products of the successful infection. Other relevant criteria can also be measured. The number and strength of doses are adjusted according to the subject's needs.

Example 16

Treatment of a Subject with a PVRL4-binding Agent

A subject (e.g., a human) is treated with a PVRL4-binding agent (e.g., an antibody or siRNA specific for PVRL4) to treat a condition such as a virus infection (e.g., a measles virus infection). In some instances, one or more additional agents are co-administered. A subject in need of treatment can be selected or identified based on PVRL4 expression on one or more cells of interest, e.g., an epithelial cell capable of being infected by virus. The identification of the subject can occur in a clinical setting, or elsewhere, e.g., in the subject's home through the subject's own use of a self-testing kit or by a third party. At time zero, a suitable first dose of agent is administered to the subject. The agent is formulated as described herein. After a period of time following the first dose, e.g., 7 days, 14 days, and 21 days, the subject's condition is evaluated. This measurement can be accompanied by a measurement of MV infection (e.g., cfu) in said subject. Other relevant criteria can also be measured. The number and strength of doses are adjusted according to the subject's needs.

While the invention has been particularly shown and described with reference to a preferred aspect and various alternate aspects, it will be understood by persons skilled in the the relevant art that various changes in form and details can be made therein without departing from the spirit and scope of the invention.

All references, issued patents and patent applications cited within the instant specification are hereby incorporated by reference in their entirety, for all purposes.

REFERENCES

1. Enders J F, Katz S L, Holloway A (1962) Development of attenuated measles-virus vaccines. A summary of recent-investigation. Am J Dis Child 103: 335-340.
2. Moss W J (2009) Measles control and the prospect of eradication. Curr Top Microbiol Immunol 330: 173-189.
3. Blake F G, Trask J D (1921) Studies on Measles: I. Susceptibility of Monkeys to the Virus of Measles. J Exp Med 33: 385-412.
4. de Swart R L (2009) Measles studies in the macaque model. Curr Top Microbiol Immunol 330: 55-72.
5. Kobune F, Takahashi H, Terao K, Ohkawa T, Ami Y, et al. (1996) Nonhuman primate models of measles. Lab Anim Sci 46: 315-320.
6. McChesney M B, Miller C J, Rota P A, Zhu Y D, Antipa L, et al. (1997) Experimental measles. I. Pathogenesis in the normal and the immunized host. Virology 233: 74-84.
7. Zhu Y D, Heath J, Collins J, Greene T, Antipa L, et al. (1997) Experimental measles. II. Infection and immunity in the rhesus macaque. Virology 233: 85-92.
8. Burnstein T, Jensen J H, Waksman B H (1964) The Development of a Neurotropic Strain of Measles Virus in Hamsters and Mice. J Infect Dis 114: 265-272.
9. Griffin D E, Mullinix J, Narayan O, Johnson R T (1974) Age dependence of viral expression: comparative pathogenesis of two rodent-adapted strains of measles virus in mice. Infect Immun 9: 690-695.
10. Liebert U G, Finke D (1995) Measles virus infections in rodents. Curr Top Microbiol Immunol 191: 149-166.
11. Blechacz B, Russell S J (2008) Measles virus as an oncolytic vector platform. Curr Gene Ther 8: 162-175.
12. Russell S J, Peng K W (2009) Measles virus for cancer therapy. Curr Top Microbiol Immunol 330: 213-241.
13. Griffin D E (2006) Measles Virus. In: Knipe D. M., editor in chief. Fields' Virology. pp 1551-1585. New York: Lippincott, Williams, and Wilkins.
14. Navaratnarajah C K, Leonard V H, Cattaneo R (2009) Measles virus glycoprotein complex assembly, receptor attachment, and cell entry. Curr Top Microbiol Immunol 329: 59-76.
15. Hashiguchi T, Ose T, Kubota M, Maita N, Kamishikiryo J, et al. (2011) Structure of the measles virus hemagglutinin bound to its cellular receptor SLAM. Nat Struct Mol Biol. 18: 135-141.
16. Navaratnarajah C K, Oezguen N, Rupp L, Kay L, Leonard V H, et al. (2011) The heads of the measles virus attachment protein move to transmit the fusion-triggering signal. Nat Struct Mol Biol. 18: 128-134.
17. Yanagi Y, Takeda M, Ohno S, Hashiguchi T (2009) Measles virus receptors. Curr Top Microbiol Immunol 329: 13-30.
18. Dorig R E, Marcil A, Chopra A, Richardson C D (1993) The human CD46 molecule is a receptor for measles virus (Edmonston strain). Cell 75: 295-305.
19. Naniche D, Varior-Krishnan G, Cervoni F, Wild T F, Rossi B, et al. (1993) Human membrane cofactor protein (CD46) acts as a cellular receptor for measles virus. J Virol 67: 6025-6032.
20. Kemper C, Atkinson J P (2009) Measles virus and CD46. Curr Top Microbiol Immunol 329: 31-57.
21. Lecouturier V, Fayolle J, Caballero M, Carabana J, Celma M L, et al. (1996) Identification of two amino acids in the hemagglutinin glycoprotein of measles virus (MV) that govern hemadsorption, HeLa cell fusion, and CD46 down-regulation: phenotypic markers that differentiate vaccine and wild-type MV strains. J Virol 70: 4200-4204.
22. Hsu E C, Sarangi F, Iorio C, Sidhu M S, Udem S A, et al. (1998) A single amino acid change in the hemagglutinin protein of measles virus determines its ability to bind CD46 and reveals another receptor on marmoset B cells. J Virol 72: 2905-2916.
23. Tahara M, Takeda M, Seki F, Hashiguchi T, Yanagi Y (2007) Multiple amino acid substitutions in hemagglutinin are necessary for wild-type measles virus to acquire the ability to use receptor CD46 efficiently. J Virol 81: 2564-2572.
24. Kobune F, Sakata H, Sugiura A (1990) Marmoset lymphoblastoid cells as a sensitive host for isolation of measles virus. J Virol 64: 700-705.
25. Shibahara K, Hotta H, Katayama Y, Homma M (1994) Increased binding activity of measles virus to monkey red blood cells after long-term passage in Vero cell cultures. J Gen Virol 75 (Pt 12): 3511-3516.
26. Bartz R, Firsching R, Rima B, ter Meulen V, Schneider-Schaulies J (1998) Differential receptor usage by measles virus strains. J Gen Virol 79 (Pt 5): 1015-1025.
27. Buckland R, Wild T F (1997) Is CD46 the cellular receptor for measles virus? Virus Res 48: 1-9.
28. Tatsuo H, Ono N, Tanaka K, Yanagi Y (2000) SLAM (CDw150) is a cellular receptor for measles virus. Nature 406: 893-897.
29. Hsu E C, Iorio C, Sarangi F, Khine A A, Richardson C D (2001) CDw150(SLAM) is a receptor for a lymphotropic strain of measles virus and may account for the immunosuppressive properties of this virus. Virology 279: 9-21.
30. Erlenhoefer C, Wurzer W J, Loffler S, Schneider-Schaulies S, ter Meulen V, et al. (2001) CD150 (SLAM) is a receptor for measles virus but is not involved in viral contact-mediated proliferation inhibition. J Virol 75: 4499-4505.
31. Schwartzberg P L, Mueller K L, Qi H, Cannons J L (2009) SLAM receptors and SAP influence lymphocyte interactions, development and function. Nat Rev Immunol 9: 39-46.
32. de Swart R L, Ludlow M, de Witte L, Yanagi Y, van Amerongen G, et al. (2007) Predominant infection of CD150+ lymphocytes and dendritic cells during measles virus infection of macaques. PLoS Pathog 3: e178.
33. Leonard V H, Sinn P L, Hodge G, Miest T, Devaux P, et al. (2008) Measles virus blind to its epithelial cell receptor remains virulent in rhesus monkeys but cannot cross the airway epithelium and is not shed. J Clin Invest 118: 2448-2458.
34. Ludlow M, Rennick L J, Sarlang S, Skibinski G, McQuaid S, et al. (2010) Wild-type measles virus infection of primary epithelial cells occurs via the basolateral surface without syncytium formation or release of infectious virus. J Gen Virol. 91: 971-979.
35. Lemon K, de Vries R D, Mesman A W, McQuaid S, van Amerongen G, et al. (2011) Early target cells of measles virus after aerosol infection of non-human primates. PLoS Pathog 7: e1001263.
36. Craighead J E (2000) Pathology and pathogenesis of human viral disease. In: Craighead J E, editor. Rubeola (Measles). Philadelphia: Elsevier Inc. pp. 397-410.

37. Sakaguchi M, Yoshikawa Y, Yamanouchi K, Sata T, Nagashima K, et al. (1986) Growth of measles virus in epithelial and lymphoid tissues of cynomolgus monkeys. Microbiol Immunol 30: 1067-1073.
38. Griffin D E (2001) Measles Virus. In: Knipe D. M., editor in chief. Fields' Virology. New York: Lippincott, Williams, and Wilkins. pp. 1401-1442.
39. Takeuchi K, Miyajima N, Nagata N, Takeda M, Tashiro M (2003) Wild-type measles virus induces large syncytium formation in primary human small airway epithelial cells by a SLAM(CD150)-independent mechanism. Virus Res 94: 11-16.
40. Sinn P L, Williams G, Vongpunsawad S, Cattaneo R, McCray P B, Jr. (2002) Measles virus preferentially transduces the basolateral surface of well-differentiated human airway epithelia. J Virol 76: 2403-2409.
41. Tahara M, Takeda M, Shirogane Y, Hashiguchi T, Ohno S, et al. (2008) Measles virus infects both polarized epithelial and immune cells by using distinctive receptor-binding sites on its hemagglutinin. J Virol 82: 4630-4637.
42. Takeda M (2008) Measles virus breaks through epithelial cell barriers to achieve transmission. J Clin Invest 118: 2386-2389.
43. Maisner A, Klenk H, Herrler G (1998) Polarized budding of measles virus is not determined by viral surface glycoproteins. J Virol 72: 5276-5278.
44. Hashimoto K, Ono N, Tatsuo H, Minagawa H, Takeda M, et al. (2002) SLAM (CD150)-independent measles virus entry as revealed by recombinant virus expressing green fluorescent protein. J Virol 76: 6743-6749.
45. Shirogane Y, Takeda M, Tahara M, Ikegame S, Nakamura T, et al. (2010) Epithelial-mesenchymal transition abolishes the susceptibility of polarized epithelial cell lines to measles virus. J Biol Chem 285: 20882-20890.
46. Takeda M, Tahara M, Hashiguchi T, Sato T A, Jinnouchi F, et al. (2007) A human lung carcinoma cell line supports efficient measles virus growth and syncytium formation via a SLAM- and CD46-independent mechanism. J Virol 81: 12091-12096.
47. Barton E S, Forrest J C, Connolly J L, Chappell J D, Liu Y, et al. (2001) Junction adhesion molecule is a receptor for reovirus. Cell 104: 441-451.
48. Geraghty R J, Krummenacher C, Cohen G H, Eisenberg R J, Spear P G (1998) Entry of alphaherpesviruses mediated by poliovirus receptor-related protein 1 and poliovirus receptor. Science 280: 1618-1620.
49. Coyne C B, Shen L, Turner J R, Bergelson J M (2007) Coxsackievirus entry across epithelial tight junctions requires occludin and the small GTPases Rab34 and Rab5. Cell Host Microbe 2: 181-192.
50. Ploss A, Evans M J, Gaysinskaya V A, Panis M, You H, et al. (2009) Human occludin is a hepatitis C virus entry factor required for infection of mouse cells. Nature 457: 882-886.
51. Hsu E C, Sabatinos S, Hoedemaeker F J, Rose D R, Richardson C D (1999) Use of site-specific mutagenesis and monoclonal antibodies to map regions of CD46 that interact with measles virus H protein. Virology 258: 314-326.
52. Vongpunsawad S, Oezgun N, Braun W, Cattaneo R (2004) Selectively receptor-blind measles viruses: Identification of residues necessary for SLAM- or CD46-induced fusion and their localization on a new hemagglutinin structural model. J Virol 78: 302-313
53. Hsu E C, Dorig R E, Sarangi F, Marcil A, Iorio C, et al. (1997) Artificial mutations and natural variations in the CD46 molecules from human and monkey cells define regions important for measles virus binding. J Virol 71: 6144-6154.
54. Riley R C, Tannenbaum P L, Abbott D H, Atkinson J P (2002) Cutting edge: inhibiting measles virus infection but promoting reproduction: an explanation for splicing and tissue-specific expression of CD46. J Immunol 169: 5405-5409.
55. Bonaparte M I, Dimitrov A S, Bossart K N, Crameri G, Mungall B A, et al. (2005) Ephrin-B2 ligand is a functional receptor for Hendra virus and Nipah virus. Proc Natl Acad Sci USA 102: 10652-10657.
56. Naniche D, Wild T F, Rabourdin-Combe C, Gerlier D (1993) Measles virus haemagglutinin induces down-regulation of gp57/67, a molecule involved in virus binding. J Gen Virol 74 (Pt 6): 1073-1079.
57. Schneider-Schaulies J, Dunster L M, Kobune F, Rima B, ter Meulen V (1995) Differential downregulation of CD46 by measles virus strains. J Virol 69: 7257-7259.
58. Bartz R, Brinckmann U, Dunster L M, Rima B, Ter Meulen V, et al. (1996) Mapping amino acids of the measles virus hemagglutinin responsible for receptor (CD46) downregulation. Virology 224: 334-337.
59. Tanaka K, Minagawa H, Xie M F, Yanagi Y (2002) The measles virus hemagglutinin downregulates the cellular receptor SLAM (CD150). Arch Virol 147: 195-203.
60. Welstead G G, Hsu E C, Iorio C, Bolotin S, Richardson C D (2004) Mechanism of CD150 (SLAM) down regulation from the host cell surface by measles virus hemagglutinin protein. J Virol 78: 9666-9674.
61. Reymond N, Fabre S, Lecocq E, Adelaide J, Dubreuil P, et al. (2001) Nectin4/PRR4, a new afadin-associated member of the nectin family that trans-interacts with nectin1/PRR1 through V domain interaction. J Biol Chem 276: 43205-43215.
62. Derycke M S, Pambuccian S E, Gilks C B, Kalloger S E, Ghidouche A, et al. (2010) Nectin 4 overexpression in ovarian cancer tissues and serum: potential role as a serum biomarker. Am J Clin Pathol 134: 835-845.
63. Takano A, Ishikawa N, Nishino R, Masuda K, Yasui W, et al. (2009) Identification of nectin-4 oncoprotein as a diagnostic and therapeutic target for lung cancer. Cancer Res 69: 6694-6703.
64. Fabre-Lafay S, Gamido-Urbani S, Reymond N, Goncalves A, Dubreuil P, et al. (2005) Nectin-4, a new serological breast cancer marker, is a substrate for tumor necrosis factor-alpha-converting enzyme (TACE)/ADAM-17. J Biol Chem 280: 19543-19550.
65. Meng W, Takeichi M (2009) Adherens junction: molecular architecture and regulation. Cold Spring Harb Perspect Biol 1: a002899.
66. Mendelsohn C L, Wimmer E, Racaniello V R (1989) Cellular receptor for poliovirus: molecular cloning, nucleotide sequence, and expression of a new member of the immunoglobulin superfamily. Cell 56: 855-865.
67. Lopez M, Cocchi F, Menotti L, Avitabile E, Dubreuil P, et al. (2000) Nectin2alpha (PRR2alpha or HveB) and nectin2delta are low-efficiency mediators for entry of herpes simplex virus mutants carrying the Leu25Pro substitution in glycoprotein D. J Virol 74: 1267-1274.
68. Taylor J M, Lin E, Susmarski N, Yoon M, Zago A, et al. (2007) Alternative entry receptors for herpes simplex virus and their roles in disease. Cell Host Microbe 2: 19-28.
69. Yu Z, Adusumilli P S, Eisenberg D P, Darr E, Ghossein R A, et al. (2007) Nectin-1 expression by squamous cell carcinoma is a predictor of herpes oncolytic sensitivity. Mol Ther 15: 103-113.

70. von Messling V, Milosevic D, Cattaneo R (2004) Tropism illuminated: lymphocyte-based pathways blazed by lethal *morbillivirus* through the host immune system. Proc Natl Acad Sci USA 101: 14216-14221.
71. Fabre-Lafay S, Monville F, Gamido-Urbani S, Berruyer-Pouyet C, Ginestier C, et al. (2007) Nectin-4 is a new histological and serological tumor associated marker for breast cancer. BMC Cancer 7: 73.
72. Bluming A Z, Ziegler J L (1971) Regression of Burkitt's lymphoma in association with measles infection. Lancet 2: 105-106.
73. Mota H C (1973) Infantile Hodgkin's disease: remission after measles. Br Med J 2: 421.
74. Taqi A M, Abdurrahman M B, Yakubu A M, Fleming A F (1981) Regression of Hodgkin's disease after measles. Lancet 1: 1112.
75. Zygiert Z (1971) Hodgkin's disease: remissions after measles. Lancet 1: 593.
76. Richardson C D, Scheid A, Choppin P W (1980) Specific inhibition of paramyxovirus and myxovirus replication by oligopeptides with amino acid sequences similar to those at the N-termini of the F1 or HA2 viral polypeptides. Virology 105: 205-222.

TABLES

TABLE 1

Adenocarcinoma cell lines tested for susceptibility to wt MV-EGFP infection. See also FIG. 12.

| Tissue Type | Cell Line | Tumour Type | % Infection Efficiency |
|---|---|---|---|
| Lung | MGH24 | adenocarcinoma | +++++ |
| | NCI-H358 | adenocarcinoma | +++++ |
| | NCI-H125 | adenocarcinoma | ++++ |
| | Calu-3 | adenocarcinoma | ++++ |
| | RVH6847 | adenocarcinoma | + |
| | A549 | adenocarcinoma | − |
| | SBC-3 | small cell carcinoma | − |
| | MGH7 | squamous cell carcinoma | − |
| | NCI-H157 | squamous cell carcinoma | − |
| | NCI-H460 | large cell carcinoma | − |
| | NCI-H661 | large cell carcinoma | − |
| | NCI-H520 | squamous cell carcinoma | − |
| | NCI-H226 | squamous cell carcinoma | − |
| Breast | MCF7 | adenocarcinoma | +++++ |
| | MDA-MB-468 | adenocarcinoma | +++++ |
| | T47D | adenocarcinoma | ++++ |
| | MDA-MB-231 | adenocarcinoma | − |
| Colon | DLD-1 | adenocarcinoma | +++++ |
| | LoVo | adenocarcinoma | +++++ |
| | T84 | adenocarcinoma | ++++ |
| | HT29 | adenocarcinoma | ++++ |
| | HCT116 | adenocarcinoma | − |
| Liver | Huh7 | adenocarcinoma | + |
| | Hep3B | adenocarcinoma | + |
| Pancreas | HS766T | adenocarcinoma | − |
| Cervix | HeLa | adenocarcinoma | − |
| Kidney | MDCK (dog) | n.a. | +/− |
| | Vero (green monkey) | n.a. | +/− |
| | HEK 293 (human) | n.a. | +/− |
| | COS-1 (green monkey) | n.a. | +/− |
| | OMK (owl monkey) | n.a. | − |
| | NZP60 (marmoset) | n.a. | − |
| | BHK21 (hamster) | n.a. | +/− |
| Ovary | CHO (hamster) | n.a. | − |

+++++ 100% cells infected;
++++ 80% cells infected;
+++ 60% cells infected;
++ 40% cell infected;
+ 20% cells infected;
+/− 5% cells infected;
− 0% cells infected

TABLE 2

Gene products upregulated in permissive breast, lung, and SAEC cell lines compared to non-permissive cells

| Common Genes Up-regulated in Breast & Lung Cells | % Gene Up-Regulation in Breast Cells | % Gene Up-Regulation in Lung Cells | Common Genes Up-regulated in Breast, Lung, SAEC | % Gene Up-Regulation in SAEC's |
|---|---|---|---|---|
| SLC6A14* | 173.1415 | 61.90872 | SLC6A14** | 46.87437 |
| RAB25* | 161.964 | 188.6348 | | |
| CDH1* | 131.1153 | 45.16778 | | |
| GPC4* | 103.9329 | 129.3733 | | |
| STEAP4* | 100.7787 | 109.9432 | STEAP4** | 64.64598 |
| TMPRSS11E* | 96.91898 | 118.1558 | TMPRSS11E** | 46.68319 |
| NCAM2* | 94.40557 | 43.07266 | | |
| CDH3* | 93.77679 | 123.3686 | | |
| FXYD3 | 86.12615 | 41.92274 | | |
| MUC1* | 75.34311 | 49.158 | MUC1** | 32.83022 |
| MME | 73.32612 | 82.94319 | | |
| ERBB3* | 72.10978 | 45.78744 | ERBB3** | 23.24152 |
| PCDHB8* | 70.45194 | 89.7596 | | |
| ST14* | 68.33217 | 106.8741 | | |
| GABRA3 | 65.42129 | 50.05689 | | |
| PRSS8 | 58.427 | 52.65615 | | |
| PCDHB4* | 57.51795 | 53.33358 | | |
| SLC16A14* | 55.81763 | 38.13178 | | |
| ANK3 | 51.61145 | 44.22223 | | |
| PVRL4 | 50.68993 | 38.80007 | PVRL4** | 27.6538 |
| MUC15* | 47.35872 | 60.32913 | MUC15** | 23.22254 |
| SYK | 47.19083 | 68.0141 | | |
| SCNN1A* | 47.04117 | 64.89888 | | |

TABLE 2-continued

Gene products upregulated in permissive breast, lung, and SAEC cell lines compared to non-permissive cells

| Common Genes Up-regulated in Breast & Lung Cells | % Gene Up-Regulation in Breast Cells | % Gene Up-Regulation in Lung Cells | Common Genes Up-regulated in Breast, Lung, SAEC | % Gene Up-Regulation in SAEC's |
|---|---|---|---|---|
| PCDH1* | 41.70316 | 41.02153 | PCDH1** | 22.85412 |
| FAP | 40.45849 | 38.08091 | | |
| OR8G5 | 40.37826 | 51.7274 | | |
| ANO1 | 38.69293 | 45.62884 | ANO1 | 40.30204 |
| MUC20* | 37.97506 | 45.12805 | MUC20** | 44.45975 |
| PROM2* | 37.844 | 50.14194 | | |
| SUSD4* | 37.46031 | 27.36689 | | |
| EPCAM* | 37.39759 | 116.3044 | | |
| FGFBP1* | 36.91295 | 38.48566 | | |
| EPHA1* | 35.75165 | 50.02149 | | |
| EPCAM* | 35.06523 | 95.96663 | | |
| ENPEP | 34.85825 | 77.82285 | | |
| IGSF9 | 34.23295 | 35.2908 | | |
| CHRM3 | 32.84461 | 47.77368 | | |
| PCDHB15 | 30.85493 | 45.72636 | CLDN7** | 26.90155 |
| CLDN7* | 29.9608 | 84.29241 | | |
| RAB19 | 28.47934 | 39.00469 | | |
| DSC2 | 27.83151 | 45.32287 | | |
| MMP16 | 27.7552 | 27.27076 | | |
| PSD4 | 26.42839 | 37.93089 | | |
| MAL2* | 25.88348 | 184.0902 | | |
| GJB5 | 25.58353 | 43.39558 | | |
| GPR81 | 25.39142 | 115.9613 | | |
| ADAP1 | 25.17025 | 43.49649 | | |
| VEPH1 | 24.12028 | 35.18223 | | |
| PCDHB13 | 23.84833 | 85.86242 | | |

*Primary screening of candidate receptors with cDNA expression vectors following comparison of lung and breast cancer cell lines
**Secondary screening of candidate receptors with cDNA expression vectors following comparison of lung, breast, and SAEC cell lines

The invention claimed is:

1. A method for reducing the size of a tumor in a mammal having a tumor expressing the poliovirus receptor-related 4 (PVRL4), comprising administering a wild-type measles virus via injection to the mammal such that the wild-type measles virus binds to PVRL4 and reduces the size of the tumor expressing PVRL4.

2. The method of claim 1, wherein the wild-type measles virus is injected directly into the tumor, wherein the mammal is a human, and wherein the tumor is an adenocarcinoma.

3. The method of claim 1, wherein the wild-type measles virus is injected directly into the tumor or wherein the wild-type measles virus is administered systemically to the mammal or wherein the wild-type measles virus is administered intravenously.

4. The method of claim 1, wherein the wild-type measles virus is provided in a formulation that comprises an excipient.

5. The method of claim 1, wherein the wild-type measles virus is administered at a dose greater than about $10^3$ plaque forming units (pfus), about $10^5$ pfus, about $10^6$ pfus, about $10^7$ pfus, or about $10^8$ pfus.

6. The method of claim 1, wherein the wild-type measles virus is a morbillivirus.

7. The method of claim 1, wherein the wild-type measles virus comprises protein H.

8. The method of claim 1, wherein the wild-type measles virus causes cell death through syncytia and/or apoptosis.

9. The method of claim 1, wherein the wild-type measles virus induces an immune response against the tumor.

10. The method of claim 1, wherein the wild-type measles virus induces an immune response against the tumor, and wherein the immune response is directed against one or more virus antigens.

11. The method of claim 1, wherein the administration of the wild-type measles virus reduces the number of tumor cells in the mammal.

12. The method of claim 1, further comprising monitoring a reduction of the size of the tumor.

13. A method of infecting a cell expressing PVRL4 with a wild-type measles virus, comprising injecting the cell with the wild-type measles virus.

14. The method of claim 13, wherein the cell has been predetermined to express PVRL4.

15. The method of claim 14, wherein PVRL4 expression is determined by a nucleotide-based assay or an antibody-based assay.

16. The method of claim 1, wherein the tumor is an adenocarcinoma selected from breast, lung, colon, or liver adenocarcinomas.

* * * * *

SEQUENCE LISTING

<160> NUMBER OF SEQ ID NOS: 8

<210> SEQ ID NO 1
<211> LENGTH: 517
<212> TYPE: PRT
<213> ORGANISM: Homo sapiens

<400> SEQUENCE: 1

Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
    50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
            165                 170                 175

Gly Lys Pro Pro Ser Val Val Ser Trp Glu Thr Arg Leu Lys Gly Glu
        180                 185                 190

Ala Glu Tyr Gln Glu Ile Arg Asn Pro Asn Gly Thr Val Thr Val Ile
    195                 200                 205

Ser Arg Tyr Arg Leu Val Pro Ser Arg Glu Ala His Gln Gln Ser Leu
210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
            245                 250                 255

Asn Trp Tyr Leu Gln Arg Met Asp Val Lys Leu Thr Cys Lys Ala Asp
        260                 265                 270

Ala Asn Pro Pro Ala Thr Glu Tyr His Trp Thr Thr Leu Asn Gly Ser
    275                 280                 285

Leu Pro Lys Gly Val Glu Ala Gln Asn Arg Thr Leu Phe Phe Lys Gly
290                 295                 300

Pro Ile Asn Tyr Ser Leu Ala Gly Thr Tyr Ile Cys Glu Ala Thr Asn
305                 310                 315                 320

Pro Ile Gly Thr Arg Ser Gly Gln Val Glu Val Asn Ile Thr Glu Phe
            325                 330                 335

Pro Tyr Thr Pro Ser Pro Pro Glu His Gly Arg Arg Ala Gly Pro Val
        340                 345                 350

Pro Thr Ala Ile Ile Gly Gly Val Ala Gly Ser Ile Leu Leu Val Leu
    355                 360                 365

Ile Val Val Gly Gly Ile Val Val Ala Leu Arg Arg Arg His Thr
370                 375                 380

Phe Lys Gly Asp Tyr Ser Thr Lys Lys His Val Tyr Gly Asn Gly Tyr
385                 390                 395                 400

Ser Lys Ala Gly Ile Pro Gln His His Pro Pro Met Ala Gln Asn Leu
            405                 410                 415

Gln Tyr Pro Asp Asp Ser Asp Asp Glu Lys Lys Ala Gly Pro Leu Gly
        420                 425                 430

Gly Ser Ser Tyr Glu Glu Glu Glu Glu Glu Glu Gly Gly Gly Gly Gly
    435                 440                 445

Gly Glu Arg Lys Val Gly Gly Pro His Pro Lys Tyr Asp Glu Asp Ala
450                 455                 460

Lys Arg Pro Tyr Phe Thr Val Asp Glu Ala Glu Ala Arg Gln Asp Gly
465                 470                 475                 480

Tyr Gly Asp Arg Thr Leu Gly Tyr Gln Tyr Asp Pro Glu Gln Leu Asp
            485                 490                 495

Leu Ala Glu Asn Met Val Ser Gln Asn Asp Gly Ser Phe Ile Ser Lys
        500                 505                 510

Lys Glu Trp Tyr Val
    515

<210> SEQ ID NO 2
<211> LENGTH: 538
<212> TYPE: PRT
<213> ORGANISM: Homo sapiens

<400> SEQUENCE: 2

```
Met Ala Arg Ala Ala Ala Leu Leu Pro Ser Arg Ser Pro Thr Pro
1               5                   10                  15

Leu Leu Trp Pro Leu Leu Leu Leu Leu Glu Thr Gly Ala Gln
            20                  25                  30

Asp Val Arg Val Gln Val Leu Pro Glu Val Arg Gly Gln Leu Gly Gly
        35                  40                  45

Thr Val Glu Leu Pro Cys His Leu Leu Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
                100                 105                 110

Gly Gln Asp Thr Glu Ala Glu Leu Gln Asp Ala Thr Leu Ala Leu His
            115                 120                 125

Gly Leu Thr Val Glu Asp Glu Gly Asn Tyr Thr Cys Glu Phe Ala Thr
130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
                180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
210                 215                 220

Leu Val Pro Ser Gly Arg Ala Asp Gly Val Thr Val Thr Cys Lys Val
225                 230                 235                 240

Glu His Glu Ser Phe Glu Glu Pro Ala Leu Ile Pro Val Thr Leu Ser
                245                 250                 255

Val Arg Tyr Pro Pro Glu Val Ser Ile Ser Gly Tyr Asp Asp Asn Trp
                260                 265                 270

Tyr Leu Gly Arg Thr Asp Ala Thr Leu Ser Cys Asp Val Arg Ser Asn
        275                 280                 285

Pro Glu Pro Thr Gly Tyr Asp Trp Ser Thr Thr Ser Gly Thr Phe Pro
            290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
                355                 360                 365

Ile Ile Ala Thr Ala Val Ala Ala Thr Gly Ile Leu Ile Cys Arg Gln
            370                 375                 380

Gln Arg Lys Glu Gln Thr Leu Gln Gly Ala Glu Glu Asp Glu Asp Leu
385                 390                 395                 400

Glu Gly Pro Pro Ser Tyr Lys Pro Pro Thr Pro Lys Ala Lys Leu Glu
                405                 410                 415
```

```
Ala Gln Glu Met Pro Ser Gln Leu Phe Thr Leu Gly Ala Ser Glu His
            420                 425                 430

Ser Pro Leu Lys Thr Pro Tyr Phe Asp Ala Gly Ala Ser Cys Thr Glu
        435                 440                 445

Gln Glu Met Pro Arg Tyr His Glu Leu Pro Thr Leu Glu Glu Arg Ser
    450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Tyr Leu Asp Lys Ile Asn Pro Ile
                500                 505                 510

Tyr Asp Ala Leu Ser Tyr Ser Ser Pro Ser Asp Ser Tyr Gln Gly Lys
                515                 520                 525

Gly Phe Val Met Ser Arg Ala Met Tyr Val
        530                 535

<210> SEQ ID NO 3
<211> LENGTH: 549
<212> TYPE: PRT
<213> ORGANISM: Homo sapiens

<400> SEQUENCE: 3

Met Ala Arg Thr Leu Arg Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
                20                  25                  30

Pro Pro Thr Pro Pro Leu Leu Leu Leu Leu Phe Pro Leu Leu Leu
            35                  40                  45

Phe Ser Arg Leu Cys Gly Ala Leu Ala Gly Pro Ile Ile Val Glu Pro
        50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
                100                 105                 110

Val Gln Gly Glu Tyr Gln Gly Arg Val Leu Phe Lys Asn Tyr Ser Leu
            115                 120                 125

Asn Asp Ala Thr Ile Thr Leu His Asn Ile Gly Phe Ser Asp Ser Gly
        130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
                180                 185                 190

Cys Ile Ala Ala Thr Gly Lys Pro Val Ala His Ile Asp Trp Glu Gly
        195                 200                 205

Asp Leu Gly Glu Met Glu Ser Thr Thr Ser Phe Pro Asn Glu Thr
        210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255
```

Ile Arg Tyr Ser Phe Ile Leu Asp Ile Gln Tyr Ala Pro Glu Val Ser
            260                 265                 270

Val Thr Gly Tyr Asp Gly Asn Trp Phe Val Gly Arg Lys Gly Val Asn
        275                 280                 285

Leu Lys Cys Asn Ala Asp Ala Asn Pro Pro Phe Lys Ser Val Trp
290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                325                 330                 335

Ile Cys Lys Val Thr Asn Ser Leu Gly Gln Arg Ser Asp Gln Lys Val
            340                 345                 350

Ile Tyr Ile Ser Asp Pro Pro Thr Thr Thr Leu Gln Pro Thr Ile
        355                 360                 365

Gln Trp His Pro Ser Thr Ala Asp Ile Glu Asp Leu Ala Thr Glu Pro
370                 375                 380

Lys Lys Leu Pro Phe Pro Leu Ser Thr Leu Ala Thr Ile Lys Asp Asp
385                 390                 395                 400

Thr Ile Ala Thr Ile Ile Ala Ser Val Val Gly Gly Ala Leu Phe Ile
                405                 410                 415

Val Leu Val Ser Val Leu Ala Gly Ile Phe Cys Tyr Arg Arg Arg
            420                 425                 430

Thr Phe Arg Gly Asp Tyr Phe Ala Lys Asn Tyr Ile Pro Pro Ser Asp
        435                 440                 445

Met Gln Lys Glu Ser Gln Ile Asp Val Leu Gln Gln Asp Glu Leu Asp
    450                 455                 460

Ser Tyr Pro Asp Ser Val Lys Lys Glu Asn Lys Asn Pro Val Asn Asn
465                 470                 475                 480

Leu Ile Arg Lys Asp Tyr Leu Glu Glu Pro Glu Lys Thr Gln Trp Asn
                485                 490                 495

Asn Val Glu Asn Leu Asn Arg Phe Glu Arg Pro Met Asp Tyr Tyr Glu
            500                 505                 510

Asp Leu Lys Met Gly Met Lys Phe Val Ser Asp Glu His Tyr Asp Glu
        515                 520                 525

Asn Glu Asp Asp Leu Val Ser His Val Asp Gly Ser Val Ile Ser Arg
530                 535                 540

Arg Glu Trp Tyr Val
545

<210> SEQ ID NO 4
<211> LENGTH: 510
<212> TYPE: PRT
<213> ORGANISM: Homo sapiens

<400> SEQUENCE: 4

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala

```
                65                  70                  75                  80
Leu Leu His Ser Lys Tyr Gly Leu His Val Ser Pro Ala Tyr Glu Gly
                    85                  90                  95
Arg Val Glu Gln Pro Pro Pro Arg Asn Pro Leu Asp Gly Ser Val
                100                 105                 110
Leu Leu Arg Asn Ala Val Gln Ala Asp Glu Gly Glu Tyr Glu Cys Arg
                115                 120                 125
Val Ser Thr Phe Pro Ala Gly Ser Phe Gln Ala Arg Leu Arg Leu Arg
                130                 135                 140
Val Leu Val Pro Pro Leu Pro Ser Leu Asn Pro Gly Pro Ala Leu Glu
145                 150                 155                 160
Glu Gly Gln Gly Leu Thr Leu Ala Ala Ser Cys Thr Ala Glu Gly Ser
                    165                 170                 175
Pro Ala Pro Ser Val Thr Trp Asp Thr Glu Val Lys Gly Thr Thr Ser
                180                 185                 190
Ser Arg Ser Phe Lys His Ser Arg Ser Ala Ala Val Thr Ser Glu Phe
                195                 200                 205
His Leu Val Pro Ser Arg Ser Met Asn Gly Gln Pro Leu Thr Cys Val
                210                 215                 220
Val Ser His Pro Gly Leu Leu Gln Asp Gln Arg Ile Thr His Ile Leu
225                 230                 235                 240
His Val Ser Phe Leu Ala Glu Ala Ser Val Arg Gly Leu Glu Asp Gln
                    245                 250                 255
Asn Leu Trp His Ile Gly Arg Glu Gly Ala Met Leu Lys Cys Leu Ser
                260                 265                 270
Glu Gly Gln Pro Pro Pro Ser Tyr Asn Trp Thr Arg Leu Asp Gly Pro
                275                 280                 285
Leu Pro Ser Gly Val Arg Val Asp Gly Asp Thr Leu Gly Phe Pro Pro
                290                 295                 300
Leu Thr Thr Glu His Ser Gly Ile Tyr Val Cys His Val Ser Asn Glu
305                 310                 315                 320
Phe Ser Ser Arg Asp Ser Gln Val Thr Val Asp Val Leu Asp Pro Gln
                    325                 330                 335
Glu Asp Ser Gly Lys Gln Val Asp Leu Val Ser Ala Ser Val Val Val
                340                 345                 350
Val Gly Val Ile Ala Ala Leu Leu Phe Cys Leu Leu Val Val Val Val
                355                 360                 365
Val Leu Met Ser Arg Tyr His Arg Arg Lys Ala Gln Gln Met Thr Gln
370                 375                 380
Lys Tyr Glu Glu Glu Leu Thr Leu Thr Arg Glu Asn Ser Ile Arg Arg
385                 390                 395                 400
Leu His Ser His His Thr Asp Pro Arg Ser Gln Pro Glu Glu Ser Val
                    405                 410                 415
Gly Leu Arg Ala Glu Gly His Pro Asp Ser Leu Lys Asp Asn Ser Ser
                420                 425                 430
Cys Ser Val Met Ser Glu Glu Pro Glu Gly Arg Ser Tyr Ser Thr Leu
                435                 440                 445
Thr Thr Val Arg Glu Ile Glu Thr Gln Thr Glu Leu Leu Ser Pro Gly
                450                 455                 460
Ser Gly Arg Ala Glu Glu Glu Asp Gln Asp Glu Gly Ile Lys Gln
465                 470                 475                 480
Ala Met Asn His Phe Val Gln Glu Asn Gly Thr Leu Arg Ala Lys Pro
                    485                 490                 495
```

Thr Gly Asn Gly Ile Tyr Ile Asn Gly Arg Gly His Leu Val
            500                 505                 510

<210> SEQ ID NO 5
<211> LENGTH: 509
<212> TYPE: PRT
<213> ORGANISM: Pongo abelii

<400> SEQUENCE: 5

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Arg Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Val Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Gln Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val

```
                355                 360                 365
Val Leu Met Ser Arg Tyr His Arg Arg Lys Ala Gln Gln Met Thr Gln
        370                 375                 380

Lys Tyr Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                        405                 410                 415

Gly Leu Arg Ala Glu Gly His Pro Asp Ser Leu Lys Asp Asn Ser Ser
                420                 425                 430

Cys Ser Val Met Ser Glu Glu Pro Glu Gly Arg Ser Tyr Ser Thr Leu
            435                 440                 445

Thr Thr Val Arg Glu Ile Glu Thr Gln Thr Glu Leu Leu Ser Pro Gly
        450                 455                 460

Ser Gly Arg Ala Glu Glu Glu Asp Gln Asp Gly Ile Lys Gln Ala
465                 470                 475                 480

Met Asn His Phe Val Gln Glu Asn Gly Thr Leu Arg Ala Lys Pro Thr
                    485                 490                 495

Gly Asn Gly Ile Tyr Ile Asn Gly Arg Gly His Leu Val
                500                 505

<210> SEQ ID NO 6
<211> LENGTH: 509
<212> TYPE: PRT
<213> ORGANISM: Canis lupus
<220> FEATURE:
<223> OTHER INFORMATION: Canis lupus familiaris

<400> SEQUENCE: 6

Met Pro Leu Ser Leu Gly Ala Glu Met Trp Gly Pro Glu Val Leu Leu
1               5                   10                  15

Leu Leu Leu Leu Leu Ala Ser Phe Thr Gly Arg Cys Arg Pro Gly Glu
                20                  25                  30

Leu Glu Thr Ser Asp Leu Val Thr Val Val Leu Gly Gln Asp Ala Lys
            35                  40                  45

Leu Pro Cys Phe Tyr Arg Gly Asp Pro Gly Glu Gln Val Gly Gln Val
50                  55                  60

Ala Trp Ala Arg Val Asp Ala Gly Glu Gly Ala Arg Glu Leu Ala Leu
65                  70                  75                  80

Leu His Ser Lys Tyr Gly Leu His Val Ser Ala Ala Tyr Glu Gly Arg
                85                  90                  95

Val Glu Gln Pro Pro Pro Arg Ser Pro Leu Asp Gly Ala Val Leu
                    100                 105                 110

Leu Arg Asn Ala Val Gln Ala Asp Glu Gly Glu Tyr Glu Cys Arg Val
            115                 120                 125

Ser Thr Phe Pro Ala Gly Ser Phe Gln Ala Arg Leu Arg Leu Arg Val
        130                 135                 140

Leu Val Pro Pro Leu Pro Ser Leu Asn Pro Gly Pro Ala Leu Glu Glu
145                 150                 155                 160

Gly Gln Gly Leu Thr Leu Ala Ala Ser Cys Thr Ala Glu Gly Ser Pro
                165                 170                 175

Ala Pro Ser Val Thr Trp Asp Thr Glu Val Lys Gly Thr Ala Ser Ser
                    180                 185                 190

Arg Ser Phe Lys His Ser Arg Ser Ala Ala Val Thr Ser Glu Phe His
            195                 200                 205

Leu Val Pro Ser Arg Ser Met Asn Gly Gln Pro Leu Thr Cys Val Val
```

```
                210                 215                 220
Ser His Pro Gly Leu Leu Gln Asp Gln Arg Ile Thr His Val Leu Gln
225                 230                 235                 240

Val Ala Phe Leu Ala Glu Ala Ser Val Arg Gly Leu Glu Asp Gln Lys
                245                 250                 255

Leu Trp Gln Val Gly Arg Glu Gly Ala Thr Leu Lys Cys Leu Ser Glu
                260                 265                 270

Gly His Pro Pro Pro Ser Tyr Asn Trp Thr Arg Leu Asp Gly Pro Leu
                275                 280                 285

Pro Ser Gly Val Arg Val Gln Gly Asp Thr Leu Gly Phe Pro Pro Leu
            290                 295                 300

Thr Ala Glu His Ser Gly Thr Tyr Val Cys His Val Ser Asn Glu Leu
305                 310                 315                 320

Ser Ser Arg Asp Ser Gln Val Thr Val Asp Val Leu Asp Pro Glu Glu
                325                 330                 335

Ala Pro Gly Lys Gln Val Asp Leu Val Ser Ala Ser Val Val Val Val
                340                 345                 350

Gly Val Ile Ala Ala Leu Leu Phe Cys Leu Val Val Val Val Val Val
                355                 360                 365

Leu Met Ser Arg Tyr His Arg Arg Lys Ala Gln Gln Met Thr Gln Lys
370                 375                 380

Tyr Glu Glu Leu Thr Leu Thr Arg Glu Asn Ser Ile Arg Arg Leu
385                 390                 395                 400

His Ser His His Ser Asp Pro Arg Ser Gln Pro Glu Glu Ser Val Gly
                405                 410                 415

Leu Arg Ala Glu Gly His Pro Asp Ser Leu Lys Asp Asn Ser Ser Cys
            420                 425                 430

Ser Val Met Ser Glu Glu Pro Glu Gly Arg Ser Tyr Ser Thr Leu Thr
                435                 440                 445

Thr Val Arg Glu Ile Glu Thr Gln Thr Glu Leu Leu Ser Pro Gly Ser
            450                 455                 460

Gly Arg Ala Glu Glu Glu Asp Arg Asp Glu Gly Ile Lys Gln Ala
465                 470                 475                 480

Met Asn His Phe Val Gln Glu Asn Gly Thr Leu Arg Ala Lys Pro Thr
                485                 490                 495

Gly Asn Gly Ile Tyr Ile Asn Gly Arg Gly His Leu Val
            500                 505

<210> SEQ ID NO 7
<211> LENGTH: 508
<212> TYPE: PRT
<213> ORGANISM: Rattus norvegicus

<400> SEQUENCE: 7

Met Pro Leu Ser Leu Gly Ala Glu Met Trp Gly Pro Glu Ala Trp Leu
1               5                   10                  15

Leu Leu Leu Phe Leu Ala Ser Phe Thr Gly Arg Tyr Ser Ala Gly Glu
                20                  25                  30

Leu Glu Thr Ser Asp Leu Val Thr Val Leu Gly Gln Asp Ala Lys
            35                  40                  45

Leu Pro Cys Phe Tyr Arg Gly Asp Pro Asp Glu Gln Val Gly Gln Val
        50                  55                  60

Ala Trp Ala Arg Val Asp Pro Asn Glu Gly Thr Arg Glu Leu Ala Leu
65                  70                  75                  80
```

```
Leu His Ser Lys Tyr Gly Leu His Val Ser Pro Ala Tyr Glu Asp Arg
                85                  90                  95
Val Glu Gln Pro Pro Pro Arg Asp Pro Leu Asp Gly Ser Ile Leu
            100                 105                 110
Leu Arg Asn Ala Val Gln Ala Asp Glu Gly Glu Tyr Glu Cys Arg Val
            115                 120                 125
Ser Thr Phe Pro Ala Gly Ser Phe Gln Ala Arg Met Arg Leu Arg Val
            130                 135                 140
Leu Val Pro Pro Leu Pro Ser Leu Asn Pro Gly Pro Pro Leu Glu Glu
145                 150                 155                 160
Gly Gln Gly Leu Thr Leu Ala Ala Ser Cys Thr Ala Glu Gly Ser Pro
                165                 170                 175
Ala Pro Ser Val Thr Trp Asp Thr Glu Val Lys Gly Thr Gln Ser Ser
            180                 185                 190
Arg Ser Phe Lys His Ser Arg Ser Ala Ala Val Thr Ser Glu Phe His
            195                 200                 205
Leu Val Pro Ser Arg Ser Met Asn Gly Gln Pro Leu Thr Cys Val Val
            210                 215                 220
Ser His Pro Gly Leu Leu Gln Asp Gln Arg Ile Thr His Thr Leu Gln
225                 230                 235                 240
Val Ala Phe Leu Ala Glu Ala Ser Val Arg Gly Leu Glu Asp Gln Asn
                245                 250                 255
Leu Trp His Val Gly Arg Glu Gly Ala Thr Leu Lys Cys Leu Ser Glu
            260                 265                 270
Gly Gln Pro Pro Lys Tyr Asn Trp Thr Arg Leu Asp Gly Pro Leu
            275                 280                 285
Pro Ser Gly Val Arg Val Lys Gly Asp Thr Leu Gly Phe Pro Pro Leu
            290                 295                 300
Thr Thr Glu His Ser Gly Val Tyr Val Cys His Val Ser Asn Glu Leu
305                 310                 315                 320
Ser Ser Arg Ala Ser Gln Val Thr Val Glu Val Leu Asp Pro Glu Asp
                325                 330                 335
Pro Gly Lys Gln Val Asp Leu Val Ser Ala Ser Val Val Val Val Gly
            340                 345                 350
Val Ile Ala Ala Leu Leu Phe Cys Leu Leu Val Val Val Val Val Leu
            355                 360                 365
Met Ser Arg Tyr His Arg Arg Lys Ala Gln Gln Met Thr Gln Lys Tyr
            370                 375                 380
Glu Glu Glu Leu Thr Leu Thr Arg Glu Asn Ser Ile Arg Arg Leu His
385                 390                 395                 400
Ser His His Thr Asp Pro Arg Ser Gln Pro Glu Glu Ser Val Gly Leu
                405                 410                 415
Arg Ala Glu Gly His Pro Asp Ser Leu Lys Asp Asn Ser Ser Cys Ser
            420                 425                 430
Val Met Ser Glu Glu Pro Glu Gly Arg Ser Tyr Ser Thr Leu Thr Thr
            435                 440                 445
Val Arg Glu Ile Glu Thr Gln Thr Glu Leu Leu Ser Pro Gly Ser Gly
            450                 455                 460
Arg Thr Glu Glu Glu Asp Gln Asp Glu Gly Ile Lys Gln Ala Met
465                 470                 475                 480
Asn His Phe Val Gln Glu Asn Gly Thr Leu Arg Ala Lys Pro Thr Gly
                485                 490                 495
Asn Gly Ile Tyr Ile Asn Gly Arg Gly His Leu Val
```

<210> SEQ ID NO 8
<211> LENGTH: 508
<212> TYPE: PRT
<213> ORGANISM: Mus musculus

<400> SEQUENCE: 8

Met Pro Leu Ser Leu Gly Ala Glu Met Trp Gly Pro Glu Ala Trp Leu
1               5                   10                  15

Arg Leu Leu Phe Leu Ala Ser Phe Thr Gly Gln Tyr Ser Ala Gly Glu
            20                  25                  30

Leu Glu Thr Ser Asp Val Val Thr Val Leu Gly Gln Asp Ala Lys
        35                  40                  45

Leu Pro Cys Phe Tyr Arg Gly Asp Pro Asp Glu Gln Val Gly Gln Val
    50                  55                  60

Ala Trp Ala Arg Val Asp Pro Asn Glu Gly Ile Arg Glu Leu Ala Leu
65                  70                  75                  80

Leu His Ser Lys Tyr Gly Leu His Val Asn Pro Ala Tyr Glu Asp Arg
                85                  90                  95

Val Glu Gln Pro Pro Pro Arg Asp Pro Leu Asp Gly Ser Val Leu
            100                 105                 110

Leu Arg Asn Ala Val Gln Ala Asp Glu Gly Glu Tyr Glu Cys Arg Val
        115                 120                 125

Ser Thr Phe Pro Ala Gly Ser Phe Gln Ala Arg Met Arg Leu Arg Val
    130                 135                 140

Leu Val Pro Pro Leu Pro Ser Leu Asn Pro Gly Pro Pro Leu Glu Glu
145                 150                 155                 160

Gly Gln Gly Leu Thr Leu Ala Ala Ser Cys Thr Ala Glu Gly Ser Pro
                165                 170                 175

Ala Pro Ser Val Thr Trp Asp Thr Glu Val Lys Gly Thr Gln Ser Ser
            180                 185                 190

Arg Ser Phe Thr His Pro Arg Ser Ala Ala Val Thr Ser Glu Phe His
        195                 200                 205

Leu Val Pro Ser Arg Ser Met Asn Gly Gln Pro Leu Thr Cys Val Val
    210                 215                 220

Ser His Pro Gly Leu Leu Gln Asp Arg Arg Ile Thr His Thr Leu Gln
225                 230                 235                 240

Val Ala Phe Leu Ala Glu Ala Ser Val Arg Gly Leu Glu Asp Gln Asn
                245                 250                 255

Leu Trp Gln Val Gly Arg Glu Gly Ala Thr Leu Lys Cys Leu Ser Glu
            260                 265                 270

Gly Gln Pro Pro Pro Lys Tyr Asn Trp Thr Arg Leu Asp Gly Pro Leu
        275                 280                 285

Pro Ser Gly Val Arg Val Lys Gly Asp Thr Leu Gly Phe Pro Pro Leu
    290                 295                 300

Thr Thr Glu His Ser Gly Val Tyr Val Cys His Val Ser Asn Glu Leu
305                 310                 315                 320

Ser Ser Arg Asp Ser Gln Val Thr Val Glu Val Leu Asp Pro Glu Asp
                325                 330                 335

Pro Gly Lys Gln Val Asp Leu Val Ser Ala Ser Val Ile Ile Val Gly
            340                 345                 350

Val Ile Ala Ala Leu Leu Phe Cys Leu Leu Val Val Val Val Val Leu
        355                 360                 365

-continued

```
Met Ser Arg Tyr His Arg Arg Lys Ala Gln Gln Met Thr Gln Lys Tyr
    370             375             380

Glu Glu Glu Leu Thr Leu Thr Arg Glu Asn Ser Ile Arg Arg Leu His
385             390             395             400

Ser His His Ser Asp Pro Arg Ser Gln Pro Glu Glu Ser Val Gly Leu
            405             410             415

Arg Ala Glu Gly His Pro Asp Ser Leu Lys Asp Asn Ser Ser Cys Ser
            420             425             430

Val Met Ser Glu Glu Pro Glu Gly Arg Ser Tyr Ser Thr Leu Thr Thr
        435             440             445

Val Arg Glu Ile Glu Thr Gln Thr Glu Leu Leu Ser Pro Gly Ser Gly
    450             455             460

Arg Thr Glu Glu Asp Asp Asp Gln Asp Glu Gly Ile Lys Gln Ala Met
465             470             475             480

Asn His Phe Val Gln Glu Asn Gly Thr Leu Arg Ala Lys Pro Thr Gly
            485             490             495

Asn Gly Ile Tyr Ile Asn Gly Arg Gly His Leu Val
            500             505
```